US012247197B2

United States Patent
Talebpour et al.

(10) Patent No.: US 12,247,197 B2
(45) Date of Patent: Mar. 11, 2025

(54) SYSTEMS AND METHODS FOR CLASSIFICATION OF MICROBIAL CELLS GROWN IN MICROCOLONIES

(71) Applicant: QVELLA CORPORATION, Richmond Hill (CA)

(72) Inventors: Samad Talebpour, Richmond Hill (CA); Anna Khimchenko, Thornhill (CA); Maryam Asadishekari, Vaughan (CA); Stephen Wesley Leonard, Markham (CA)

(*) Notice: Subject to any disclaimer, the term of this patent is extended or adjusted under 35 U.S.C. 154(b) by 13 days.

(21) Appl. No.: 18/012,433

(22) PCT Filed: Jun. 25, 2021

(86) PCT No.: PCT/CA2021/050884
§ 371 (c)(1),
(2) Date: Dec. 22, 2022

(87) PCT Pub. No.: WO2021/258223
PCT Pub. Date: Dec. 30, 2021

(65) Prior Publication Data
US 2023/0235274 A1 Jul. 27, 2023

Related U.S. Application Data

(60) Provisional application No. 63/044,292, filed on Jun. 25, 2020.

(51) Int. Cl.
*G06K 9/62* (2022.01)
*C12N 1/20* (2006.01)
(Continued)

(52) U.S. Cl.
CPC ............ *C12N 1/20* (2013.01); *G02B 21/367* (2013.01); *G06T 5/50* (2013.01); *G06T 5/70* (2024.01);
(Continued)

(58) Field of Classification Search
CPC ...... C12N 1/20; G02B 21/367; G02B 21/125; G06T 5/50; G06T 5/70;
(Continued)

(56) References Cited

U.S. PATENT DOCUMENTS 6,472,166 B1 * 10/2002 Wardlaw .................. C12Q 1/18
435/32
7,582,415 B2 9/2009 Strais
(Continued)

FOREIGN PATENT DOCUMENTS

WO 2010077304 A2 7/2010

OTHER PUBLICATIONS

Kearns, Daniel B. "A field guide to bacterial swarming motility." Nature Reviews Microbiology 8.9 (2010): 634-644.
(Continued)

*Primary Examiner* — Howard D Brown, Jr.
(74) *Attorney, Agent, or Firm* — HILL & SCHUMACHER

(57) ABSTRACT

Systems and methods are provided for classifying microbial cells according to morphological features of microcolonies. A dark-field objective is employed to acquire a dark-field image of a microcolony during a microcolony growth phase that is characterized by phenotypic expression of microcolony morphological features which evolve with time and are differentiated among classes of microbial cell types. The dark-field image is processed to classify the microcolony according to two or more microbial cell types, such as Gram status and/or speciation. The dark-field objective may have a numerical aperture selected to facilitate the imaging of microcolony morphological features, residing, for example, between 0.15 and 0.35. A set of dark-field images of a microcolony may be collected during the microcolony growth phase and processed to classify the microcolony.
(Continued)

Classification may be performed according to a temporal ordering of the dark-field images, for example, using a recurrent neural network.

47 Claims, 31 Drawing Sheets

(51) Int. Cl.
*G02B 21/36* (2006.01)
*G06T 5/50* (2006.01)
*G06T 5/70* (2024.01)
*G06V 10/147* (2022.01)
*G06V 10/774* (2022.01)
*G06V 10/82* (2022.01)
*G06V 20/69* (2022.01)

(52) U.S. Cl.
CPC .......... *G06V 10/147* (2022.01); *G06V 10/774* (2022.01); *G06V 10/82* (2022.01); *G06V 20/693* (2022.01); *G06V 20/698* (2022.01); *G06T 2207/10056* (2013.01); *G06T 2207/20081* (2013.01); *G06T 2207/20084* (2013.01); *G06T 2207/20212* (2013.01); *G06T 2207/30024* (2013.01)

(58) Field of Classification Search
CPC . G06T 2207/10056; G06T 2207/20081; G06T 2207/20084; G06T 2207/20212; G06T 2207/30024; G06V 10/147; G06V 10/774; G06V 10/82; G06V 20/693; G06V 20/698; C12M 41/36
See application file for complete search history.

(56) References Cited

U.S. PATENT DOCUMENTS

| | | | |
|---|---|---|---|
| 8,748,122 | B2 | 6/2014 | Hyman et al. |
| 9,619,881 | B2 | 4/2017 | Maddah et al. |
| 2015/0275262 | A1 | 10/2015 | Ratushny et al. |
| 2018/0129864 | A1 | 5/2018 | Robinson et al. |
| 2018/0285624 | A1* | 10/2018 | Robinson ............ G06V 20/698 |
| 2022/0088583 | A1* | 3/2022 | Kleinemolen ... G01N 33/54366 |
| 2022/0180515 | A1* | 6/2022 | Zhou .................... G06T 7/0012 |
| 2022/0383986 | A1* | 12/2022 | Popescu ................ G16H 30/40 |

OTHER PUBLICATIONS

Wang, Qingfeng, et al. "Sensing wetness: a new role for the bacterial flagellum." The EMBO journal 24.11 (2005): 2034-2042.
Mitchell, A. J., and J. W. T. Wimpenny. "The effects of agar concentration on the growth and morphology of submerged colonies of motile and non-motile bacteria." Journal of applied microbiology 83.1 (1997): 76-84.
Verstraeten, Natalie, et al. "Living on a surface: swarming and biofilm formation." Trends in microbiology 16.10 (2008): 496-506.
Dell'Arciprete, Dario, et al. "A growing bacterial colony in two dimensions as an active nematic." Nature communications 9.1 (2018): 4190, 9 pages.
Morales-Solo, N. et al., "Preparation, Imaging, and Quantification of Bacterial Surface Motility Assays", J. Vis. Exper. 98, 52338, 2015, doi:10.3791/52338, 10 pages.
Sun, Evelyn, Sijie Liu, and Robert EW Hancock. "Surfing motility: a conserved yet diverse adaptation among motile bacteria." Journal of Bacteriology 200.23 (2018): 10-1128, 13 pages.
Patsekin, Valery, et al. "Classification of Arcobacter species using variational autoencoders." Sensing for Agriculture and Food Quality and Safety XI. vol. 11016. SPIE, 2019, 9 pages.
Yan, Jing, et al. "Extracellular-matrix-mediated osmotic pressure drives Vibrio cholerae biofilm expansion and cheater exclusion." Nature communications 8.1 (2017): 327, 11 pages.
Kim, Huisung, et al. "Reflected scatterometry for noninvasive interrogation of bacterial colonies." Journal of Biomedical Optics 21.10 (2016): 107004-107004, 10 pages.
Castillo-Secilla, José Maria, et al. "Autofocus method for automated microscopy using embedded GPUs." Biomedical Optics Express 8.3 (2017): 1731-1740.
Bueno-Ibarra, Mario A., et al. "Fast autofocus algorithm for automated microscopes." Optical Engineering 44.6 (2005): 063601-063601, 9 pages.
Herrmann, Charles, et al. "Learning to autofocus." Proceedings of the IEEE/CVF Conference on Computer Vision and Pattern Recognition. 2020, 2230-2239.
Priest, Lee, Jack S. Peters, and Philipp Kukura. "Scattering-based light microscopy: from metal nanoparticles to single proteins." Chemical Reviews 121.19 (2021): 11937-11970.
London, Roanna, et al. "An automated system for rapid non-destructive enumeration of growing microbes." PloS one 5.1 (2010): e8609, 16 pages.
Singh, A. et al., "Comparison of objective lenses for multiphoton microscopy in turbid samples", Biomed. Opt. Exp. 6, 3113, 2015, 15 pages.
Xiong, Liyang, et al. "Flower-like patterns in multi-species bacterial colonies." Elife 9 (2020): e48885, 27 pages.
Puchkov, Evgeny. "Image analysis in microbiology: a review." Journal of Computer and Communications 4.15 (2016): 8, 26 pages.
Gopakumar, G. P. et al., "Convolutional neural network-based malaria diagnosis from focus stack of blood smear images acquired using custom-built slide scanner", J. Biophotonics. 2018;11:e201700003, 18 pages.
Manescu, P. et al., "Expert-level automated malaria diagnosis on routine blood films with deep neural networks", Am J Hematol. 2020;95:883-891.
Wei, L., Roberts, E., "Neural network control of focal position during time-lapse microscopy of cells", Sci Rep 8, 7313 (2018). DOI: 10.1038/s41598-018-25458-w, 11 pages.
Wei, L., Roberts, E., "Convolutional neural network-based malaria diagnosis from focus stack of blood smear images acquired using custom-built slide scanner", Sci Rep 8, 7313 (2018). DOI: 10.1038/s41598-018-25458-w.
Lebel, P., et al., "Label-free imaging and classication of live P. falciparum", bioRxiv, 2020, DOI:10.1101/2020.09.08.285346, 37 pages.
International Search Report for PCT/CA2021/050884 dated Sep. 28, 2021, 5 pages.
Wilson et al.:, Automated bacterial identification by angle Biomedical Optics Express, Aug. 20, 2013, vol. 7085, 10 pages.
Maeda et al., "Colony fingerprint for discrimination of microbial imaging of microcolonies", PLOS One, Apr. 3, 2017, 15 pages.
Miyata et al., "Gliding mutants of Mycoplasma mobile: relationships between motility and cell morphology, cell adhesion and microcolony formation", Microbiology, Jun. 1, 2000, vol. 146, pp. 1311-1320, ISSN 1976-3794.
Silvio D. Brugger et al: "Automated Counting of Bacterial Colony Forming Units on Agar Plates", PLoS One, vol. 7, No. 3, Mar. 20, 2012 (Mar. 20, 2012), p. e33695,XP055258738, DOI: 10.1371/journal.pone.0033695.
Bosoon Park et al: "Hyperspectral microscope imaging methods to classify gram-positive and gram-negative foodborne pathogenic bacteria", Transactions of the American Society of Agricultural Engineers, American Society of Agricultural Engineers. St.Joseph, MI, US, vol. 58, No. 1, Jan. 1, 2015 (Jan. 1, 2015), pp. 5-16, XP008182213, ISSN: 0001-2351, DOI: 10.13031/TRANS.58.10832.

\* cited by examiner

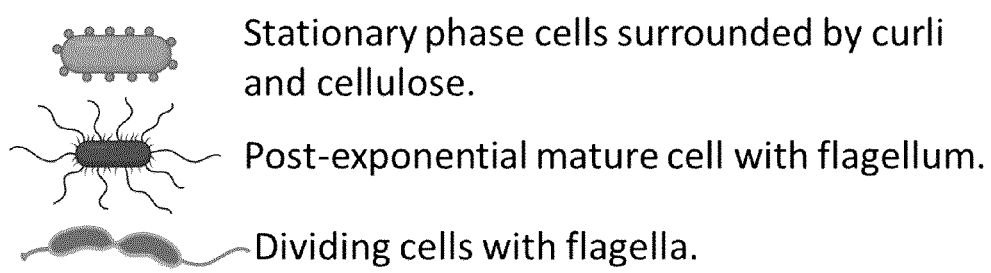
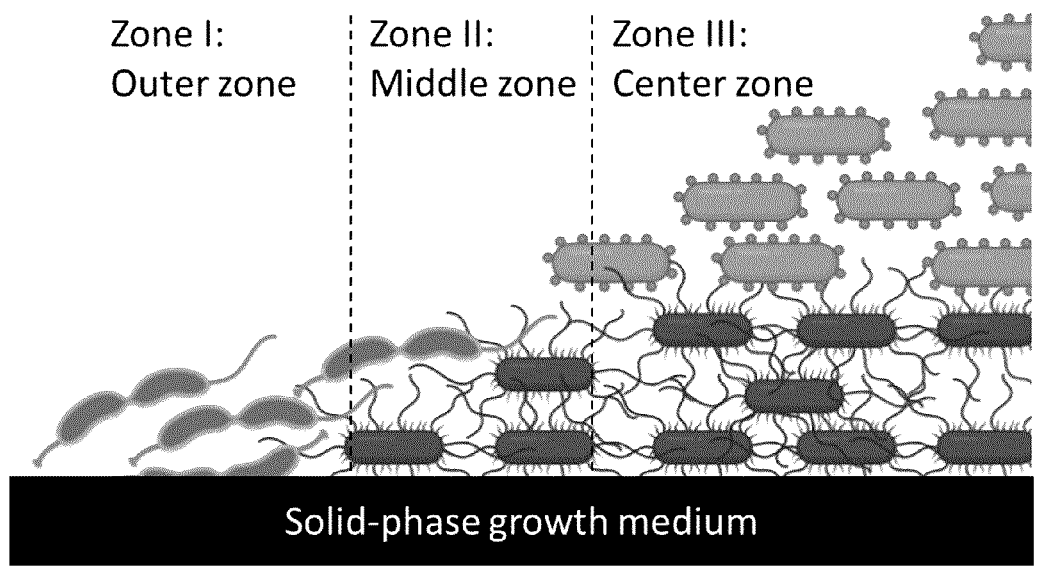
FIG. 2

| Gram Designation | Organisms | Strain ID ATCC | Number of positive microcolonies at a given incubation time h | | | | | | | | | | Earliest detection | TTP (h) |
|---|---|---|---|---|---|---|---|---|---|---|---|---|---|---|
| | | | 1 | 1.5 | 2 | 2.5 | 3 | 3.5 | 4 | 4.5 | 5 | 24 | | |
| Gram-Positive | Enterococcus faecalis | 29212 | 0 | 2 | 26 | 71 | 77 | 76 | | | | | 1.5 | 2.5 |
| | Enterococcus faecium | 35667 | 3 | 5 | 21 | 46 | 46 | 46 | 49 | | | 46 | 1 | 2.5 |
| | Staphylococcus aureus | 25923 | 94 | 71 | 152 | 197 | 193 | 196 | 200 | | | >111 | 1 | 2.5 |
| | Staphylococcus epidermidis | 12228 | | | | | 65 | 91 | 94 | 98 | | | 3 | 3.5 |
| | Staphylococcus haemolyticus | 29970 | 0 | 0 | 134 | 144 | 150 | 144 | 165 | | | | 2 | 2.5 |
| | Streptococcus pyogenes | 12344 | 0 | 4 | 15 | 18 | 22 | 23 | | 23 | | | 1.5 | 3 |
| Gram-Negative | Acinetobacter baumannii | 19606 | 0 | 0 | 19 | 5 | 20 | 43 | 55 | | | 63 | 2 | 4 |
| | Enterobacter cloacaecomplex | 13047 | 0 | 11 | 31 | 57 | 65 | 66 | | | | 60 | 1.5 | 2.5 |
| | Enterobacter aerogenes | 13048 | 0 | 2 | 14 | 24 | 30 | 30 | 31 | | | 39 | 1.5 | 3 |
| | Escherichia coli | 35218 | 19 | 31 | 45 | 62 | 66 | 65 | 70 | | | ci. 100 | 1 | 2.5 |
| | Klebsiella pneumoniae | 700603 | 14 | 12 | 29 | 55 | 63 | 68 | 68 | | | 54 | 1 | 2.5 |
| | Pseudomonas aeruginosa | 35554 | 0 | 0 | 0 | 0 | 2 | 8 | 18 | 24 | 30 | 29 | 3 | 5 |
| | Serratia marcescens | 13880 | 0 | 0 | 7 | 11 | 16 | 17 | 20 | 20 | 19 | | 2 | 4 |
| | Proteus mirabilis | 12453 | 0 | 0 | 0 | 9 | 10 | 10 | 10 | 10 | | | 2.5 | 2.5 |

FIG. 10

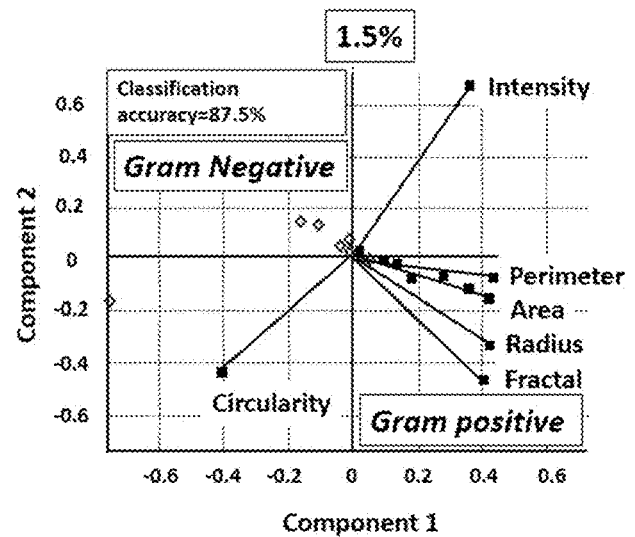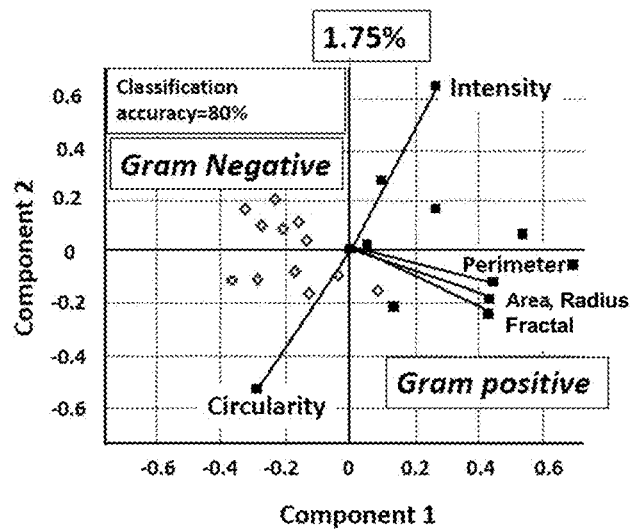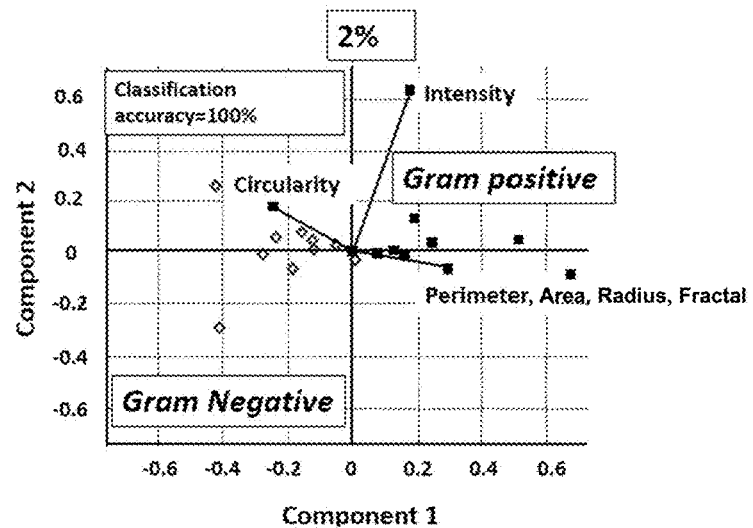
FIG. 11C

| Organism | Strain ID ATTC | Strain ID MSH |
|---|---|---|
| Enterococcus faecium | 35667 | 180412-17 |
| Staphylococcus aureus | 25923 | 180322-1 |
| Staphylococcus epidermidis | 12228 | 180412-15 |
| Strepococcus agalactiae | 27956 | 180411-14 |
| Staphylococcus heamolyticus | 29970 | 180411-12 |
| Enterococcus faecalis | 29212 | 180412-16 |
| Streptococcus pyogenes | 12344 | 180614-42 |
| Streptococcus pneumoniae | 49136 | 180323-3 |

| Organism | Strain ID | Strain ID |
|---|---|---|
| | ATTC | MSH |
| Klebsiella pneumoniae | 700603 | 180328-7 |
| Acinetobacter baumannii | 19606 | 180413-18 |
| Enterobacter aerogenes | 35029 | 180329-10 |
| Klebsiella oxytoca | 49131 | 180328-8 |
| Pseudomonas aeruginosa | 35554 | 180327-6 |
| Serratia marcescens | 13880 | 180328-9 |
| Enterobacter cloacae complex | 13047 | 180329-11 |
| Escherichia Coli | 35218 | 180322-2 |
| Proteus Mirabilis | 12335 | 181213-71 |

FIG. 15C

| Organism | Strain ID | Strain ID |
|---|---|---|
| | ATTC | MSH |
| Candida albicans | 90028 | 180323-4 |

FIG. 15D

Focus Height [μm]

SYSTEMS AND METHODS FOR CLASSIFICATION OF MICROBIAL CELLS GROWN IN MICROCOLONIES

This application is a National Phase application claiming the benefit of the international PCT Patent Application No. PCT/CA2021/050884, filed on Jun. 25, 2021, in English, which claims priority to U.S. Provisional Application No. 63/044,292, titled "SYSTEMS AND METHODS FOR CLASSIFICATION OF MICROBIAL CELLS GROWN IN MICROCOLONIES" and filed on Jun. 25, 2020, the entire contents of which are incorporated herein by reference.

BACKGROUND

The present disclosure relates to the growth, detection and characterization of microbial cells. More particularly, the present disclosure relates to microcolony cell classification.

Time-efficient detection, identification, and antimicrobial susceptibility testing of pathogenic microbial or fungal cells in biological samples are the main goals of diagnostic routine in a clinical microbiology laboratory. According to conventional methods, antimicrobial susceptibility testing proceeds after having performed pathogen classification that is based on at least a Gram stain and microscopic morphological analysis, which together enable the selection of a suitable panel of antimicrobial candidates for phenotypic testing. Pathogen identification with a higher specificity is also performed, often using matrix-assisted laser desorption/ionization, which facilitates, in combination with the minimum inhibitory concentration from antimicrobial susceptibility testing, the determination of a susceptibility profile of the pathogen according to a pathogen-specific breakpoint.

SUMMARY

Systems and methods are provided for classifying microbial cells according to morphological features of microcolonies. A dark-field objective is employed to acquire a dark-field image of a microcolony during a microcolony growth phase that is characterized by phenotypic expression of microcolony morphological features which evolve with time and are differentiated among classes of microbial cell types. The dark-field image is processed to classify the microcolony according to two or more microbial cell types, such as Gram status and/or speciation. The dark-field objective may have a numerical aperture selected to facilitate the imaging of microcolony morphological features, residing, for example, between 0.15 and 0.35. A set of dark-field images of a microcolony may be collected during the microcolony growth phase and processed to classify the microcolony. Classification may be performed according to a temporal ordering of the dark-field images, for example, using a recurrent neural network.

Accordingly, in one aspect, there is provided a method of performing classification of a microcolony, the method comprising:
employing a dark-field objective having a numerical aperture between 0.15 and 0.35 to acquire a dark-field image of the microcolony, the microcolony residing on a solid-phase growth medium; and
processing the dark-field image to classify the microcolony among to two or more microbial cell type classes based on morphological features of the microcolony.

In some example implementations of the method, the dark-field image is acquired during a microcolony growth phase characterized by time-dependent changes in dark-field morphology of the microcolony.

In some example implementations of the method, the numerical aperture of the dark-field objective is between 0.18 and 0.32.

In some example implementations of the method, the numerical aperture of the dark-field objective is between 0.16 and 0.28.

In some example implementations of the method, the dark-field image is acquired prior to the microcolony having an effective diameter of 200 microns.

In some example implementations of the method, the microcolony is prepared by: seeding a microbial cell onto the solid-phase growth medium; and incubating the solid-phase growth medium under conditions suitable for promoting growth of the microbial cell and the generation of the microcolony. The solid-phase growth medium may include agar having a concentration, for example, between 1 and 2.5% w/v, or between 1.5 and 2.25% w/v, or between 1.35 and 2% w/v.

The microbial cell may be seeded onto the solid-phase growth medium by contacting a suspension with the solid-phase growth medium, the suspension comprising the microbial cell. The suspension may be derived from a whole blood sample in the absence of an intervening growth step.

In some example implementations of the method, the microcolony is a first microcolony, the microbial cell is a first microbial cell, the solid-phase growth medium is a first solid-phase growth medium having a first composition, the dark-field image is a first dark-field image, and wherein the microbial cell is seeded onto the first solid-phase growth medium by contacting a first aliquot of a suspension with the solid-phase growth medium, the first aliquot of the suspension comprising the first microbial cell, the method further comprising:
  contacting a second aliquot of the suspension with a second solid-phase growth medium, the second aliquot of the suspension comprising a second microbial cell, the second solid-phase growth medium having a second composition that differs from the first composition;
  incubating the solid-phase growth medium under conditions suitable for promoting growth of the second microbial cell and the generation of a second microcolony; and
  acquiring a second dark-field image, the second dark-field image characterizing a dark-field morphology of the second microcolony;
  wherein the first dark-field image and the second dark-field image are processed to classify of the microcolony.

In some example implementations of the method, the dark-field image of the microcolony is obtained within 3 to 5 hours from a time at which the microbial cell was seeded onto the solid-phase growth medium.

In some example implementations of the method, the solid-phase growth medium is incubated while maintaining a relative humidity between 30% and 70%.

In some example implementations of the method, the solid-phase growth medium is incubated while maintaining a relative humidity between 30% and 99%.

In some example implementations, the method further comprises detecting a presence and a location of the microcolony; and employing the location of the microcolony to position the dark-field objective for acquiring the dark-field image.

In some example implementations of the method, the microcolony is detected by processing bright-field images of the solid-phase growth medium.

In some example implementations of the method, separate bright-field objective is employed to acquire the bright-field images. The dark-field objective may be a dual-mode objective that is reconfigurable for dark-field and bright-field imaging, and wherein the dual-mode objective is configured for bright-field imaging during collection of the bright-field images.

In some example implementations of the method, detecting the presence of the microcolony comprises:
- intermittently performing a bright-field colony detection scan by scanning the solid-phase growth medium with a bright-field objective and collecting, for each bright-field colony detection scan, a set of bright-field colony detection images, each bright-field colony detection image corresponding to a different surface region of the solid-phase growth medium;
- during or after each bright-field colony detection scanning step, processing the acquired bright-field colony detection images according to microcolony detection criteria; and
- detecting a microcolony when the microcolony detection criteria is satisfied.

In some example implementations, the method further comprises, prior to performing the bright-field colony detection scans, performing at least one bright-field reference scan of the solid-phase growth medium with the bright-field objective to obtain a set of bright-field reference images, each bright-field reference image characterizing one of the surface regions; and prior to processing the bright-field colony detection images, applying a corresponding bright-field reference image to each bright field colony detection image to remove or reduce a presence of background noise in the bright-field colony detection images. A plurality of bright-field reference scans may be performed prior to performing the bright-field colony detection scans, and wherein the bright-field reference scans are performed until reference criterion associated with a stability of spatial features in the bright-field reference images is satisfied. An initial bright field reference scan may be performed after a background stabilization time delay. The background stabilization time delay may be at least 30 minutes.

In some example implementations of the method, the dark-field image is a final dark-field image that is obtained by: with the dark-field objective positioned proximal to the microcolony, collecting a plurality of initial dark-field images, each initial dark-field image being acquired at a different axial offset of the dark-field objective relative to the solid-phase growth medium; processing the plurality of initial dark-field images to determine a focal location suitable for obtaining a focused dark-field image of surface features residing on a surface of the solid-phase growth medium; and employing the focal location when positioning the dark-field objective to obtain the final dark-field image.

The dark-field objective may be spatially offset from the focal location when acquiring the final dark-field image, thereby accommodating a finite height of the microcolony. The final dark-field image may be obtained by acquiring, at a plurality of additional locations that reside proximal to the focal location, a z-stack of secondary dark-field images; and processing the z-stack of secondary dark-field images to obtain the dark-field image for classification of the microcolony. The final dark-field image may be a composite image generated by focus-stacking two or more of the z-stack of secondary dark-field images. Processing the z-stack of secondary dark-field images may include determining, from the z-stack of secondary dark-field images, a focused dark-field image having a focusing measure exceeding a remainder of the z-stack of secondary dark-field images.

In some example implementations of the method, the surface features comprise residual debris particles originating from a sample matrix. The surface features may comprise inherent surface features of the solid-phase growth medium. The surface features may comprise extrinsic particles adsorbed onto the surface of the solid-phase growth medium, the extrinsic particles having been previously contacted with the solid-phase growth medium.

In some example implementations of the method, the dark-field image is obtained by: acquiring a z-stack of initial dark-field images; and processing the z-stack of initial dark-field images to obtain the dark-field image employed for classification of the microcolony. Processing the z-stack of initial dark-field images comprises generating a composite image by focus-stacking two or more of the z-stack of initial dark-field images. Processing the z-stack of initial dark-field images comprises determining, from the z-stack of initial dark-field images, a focused dark-field image having a focusing measure exceeding a remainder of the z-stack of initial dark-field images.

In some example implementations of the method, the dark-field objective is employed to acquire one or more additional dark-field images of the microcolony, each additional dark-field image being acquired at a different time during growth of the microcolony, the dark-field image and the one or more additional dark-field images forming a set of dark-field images of the microcolony, and wherein the set of dark-field images are processed to classify the microcolony.

Processing the set of dark-field images to classify the microcolony may comprise employing a machine learning algorithm to process the set of dark-field images to classify the microcolony. The machine learning algorithm may be trained based on labeled reference image data comprising, for each of a plurality of types of microbial cells, a set of reference dark-field images corresponding to different phases of microcolony growth.

The machine learning algorithm may be configured to process the set of dark-field images in the absence of employing a temporal ordering of the set of dark-field images. The machine learning algorithm may be configured to generate, for each dark-field image of the set of dark-field images, a set of classification measures, each classification measure providing a probability of the microcolony belonging to a respective microbial cell type class, and wherein the classification is determined by selecting the microbial cell type class having the highest associated classification measure among each of the dark-field images of the set of dark-field images.

The machine learning algorithm may be configured to generate, for each dark-field image of the set of dark-field images, a set of classification measures, each classification measure providing a probability of the microcolony belonging to a respective microbial cell type class, and wherein the classification is determined by processing the classification measures to determine an aggregate classification measure.

In some example implementations of the method, the machine learning algorithm is employed to process the set of dark-field images according to a temporal ordering of the set of dark-field images. The machine learning algorithm may have been trained based on reference image data comprising, for each of a plurality of types of microbial cells, a set of temporally-ordered reference dark-field images corresponding to different phases of microcolony growth. The machine learning algorithm may comprises a recurrent neural network. The machine learning algorithm may comprise a long short term memory network.

In some example implementations of the method, the microbial cell type classes comprise Gram-positive and Gram-negative.

In some example implementations of the method, the microbial cell type classes comprise at least one bacterial species.

In another aspect, there is provided a method of obtaining high-contrast images of microcolony morphology, the method comprising employing a dark-field objective having a numerical aperture residing between 0.15 and 0.35 to acquire a dark-field image of the microcolony, the dark-field image comprising a multi-ring morphology, the dark-field image being acquired during a microcolony growth phase characterized by time-dependent changes in dark-field microcolony morphology.

In some example implementations of the method, the numerical aperture of the dark-field objective is between 0.18 and 0.32, or is between 0.16 and 0.28.

In another aspect, there is provided a method of performing classification of a microcolony, the method comprising: acquiring a temporally ordered set of images of the microcolony during growth of the microcolony on a solid-phase growth medium; and processing the temporally ordered set of images to classify the microcolony among to two or more microbial cell type classes based on morphological features of the microcolony.

In some example implementations of the method, the temporally ordered set of images are processed and classified according to a machine learning algorithm comprising a recurrent neural network.

In some example implementations of the method, the temporally ordered set of images are processed and classified according to a machine learning algorithm comprising a long short term memory neural network.

In some example implementations of the method, the temporally ordered set of images are dark-field microscopy images. The dark-field microscopy images may be collected with a dark-field objective having a numerical aperture between 0.15 and 0.35.

In some example implementations of the method, the temporally ordered set of images comprise at least one bright field microscopy images.

In another aspect, there is provided a method of performing microcolony-based classification, the method comprising:
  seeding a microbial cell onto a solid-phase growth medium;
  incubating the solid-phase growth medium under conditions suitable for promoting growth of the microbial cell and the generation of a microcolony;
  detecting the microcolony;
  employing a dark-field objective to acquire a set of dark-field images of the microcolony, each image being acquired at a different time during growth of the microcolony; and
  processing the set of dark-field images to classify the microcolony among to two or more microbial cell type classes based on morphological features of the microcolony.

In some example implementations of the method, processing the set of dark-field images to classify the microcolony comprises employing a machine learning algorithm to process the set of dark-field images to classify the microcolony. The machine learning algorithm may have been trained with labeled reference image data, the labeled reference image data comprising, for at least one type of microbial cell, a set of reference dark-field images corresponding to different phases of microcolony growth.

In some example implementations of the method, the machine learning algorithm is employed to process the set of dark-field images according to a temporal ordering of the set of dark-field images. The machine learning algorithm may have been trained with reference image data comprising, for each of a plurality of types of microbial cells, a set of temporally-ordered training dark-field images corresponding to different phases of microcolony growth. The machine learning algorithm may comprise a recurrent neural network. The machine learning algorithm may comprise a long short term memory network. The machine learning algorithm may comprise a Siamese neural network.

In some example implementations of the method, at least one dark-field image of the set of dark-field images comprises a multi-ring microcolony morphology.

In some example implementations of the method, the set of dark-field images are collected with a dark-field objective having a numerical aperture between 0.15 and 0.35.

In another aspect, there is provided a system for performing classification of a microcolony, the system comprising:
  a dark-field objective having a numerical aperture between 0.15 and 0.35;
  an imaging camera operatively coupled to the dark-field objective; and
  processing and control circuitry operatively coupled to the imaging camera, the processing and control circuitry comprising at least one processor and associated memory, the memory comprising instructions executable by the at least one processor for performing operations comprising:
    obtaining, from the imaging camera, a dark-field microcolony image characterizing the microcolony; and
    processing the dark-field microcolony image to classify the microcolony among to two or more microbial cell type classes based on morphological features of the microcolony.

In another aspect, there is provided a system for performing classification of a microcolony, the system comprising:
  a dark-field objective;
  an incubator for incubating a solid-phase growth medium to promote growth of a microcolony from a microbial cell seeded onto the solid-phase growth medium;
  an imaging camera operatively coupled to the dark-field objective; and
  processing and control circuitry operatively coupled to the imaging camera, the processing and control circuitry comprising at least one processor and associated memory, the memory comprising instructions executable by the at least one processor for performing operations comprising:
    controlling the imaging camera to acquire a set of dark-field microcolony images characterizing a growth phase of the microcolony; and
    processing the set of dark-field microcolony images to classify the microcolony among to two or more microbial cell type classes based on morphological features of the microcolony.

In some example implementations of the system, the processing and control circuitry system is configured such that a machine learning algorithm is employed to process the set of dark-field images to classify the microcolony. The processing and control circuitry may be configured such that the machine learning algorithm processes the set of dark-field images in the absence of employing a temporal ordering of the set of dark-field images.

In some example implementations of the system, the processing and control circuitry is configured such that the machine learning algorithm processes the set of dark-field images according to a temporal ordering of the set of dark-field images. The processing and control circuitry may be configured such that the machine learning algorithm comprises a recurrent neural network. The processing and control circuitry may be configured such that the machine learning algorithm comprises a long short term memory network. The processing and control circuitry may be configured such that the machine learning algorithm comprises a Siamese neural network.

BRIEF DESCRIPTION OF THE DRAWINGS

Embodiments will now be described, by way of example only, with reference to the drawings, in which:

FIG. 2 schematically illustrates a model of *Escherichia coli* colony grown on the solid-phase growth medium.

*Pneumoniae* KP CRE MSH 1705, *Proteus Mirabilis* PM ATTC 12453) bacteria, as imaged by an upright reflected-illumination dark-field microscope with 10× objective.

Figure 5A:
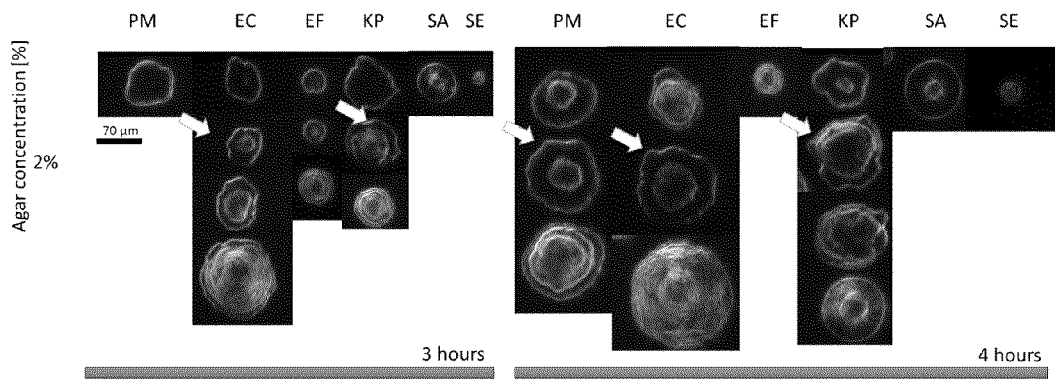
FIG. 5A presents typical dark-field images of the microcolonies of the seeded American Type Culture Collection (ATCC) strains and hospital clinical isolates (MSH) of Gram-positive (*Staphylococcus Aureus* SA ATTC 25923, *Enterococcus Faecalis* EF ATTC 51299, *Staphylococcus Epidermidis* SE ATTC 12228) and Gram-negative (*Escherichia coli* EC ATTC 35218, *Klebsiella Pneumoniae* KP CRE MSH 1705, *Proteus Mirabilis* PM ATTC 12453) bacteria after 3 and 4 hours of incubation at 37° C., as imaged by an upright reflected-illumination dark-field microscope with 10× objective. Typical microcolonies from the imaging dataset are shown with white arrow.
Figure 5B:
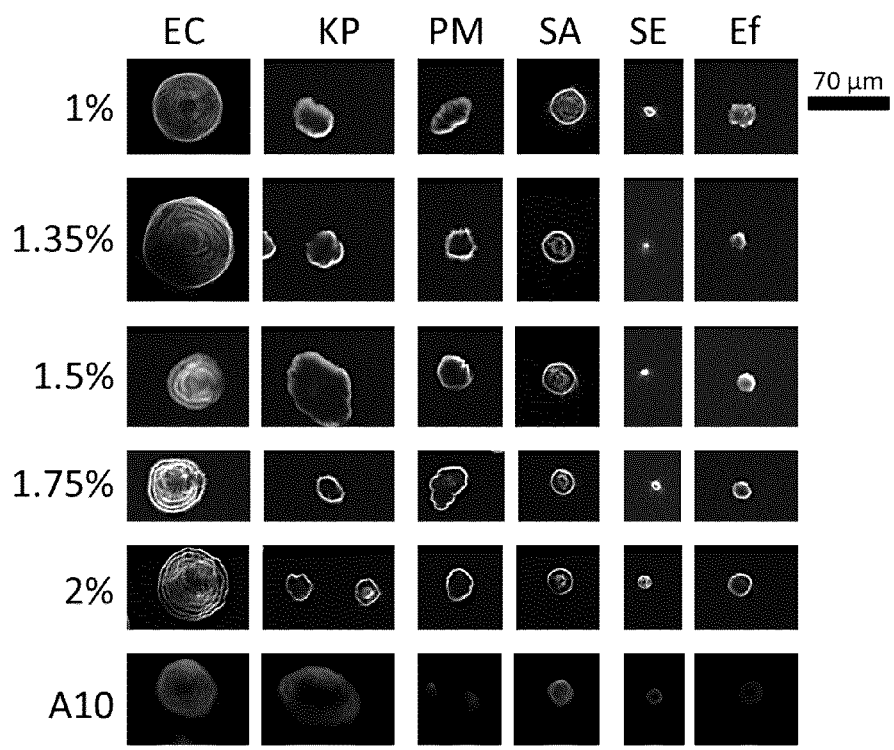
FIG. 5B presents a qualitative comparison of the microcolonies grown on the selected solid-phase growth media with respective agar concentrations of 1% w/v, 1.35% w/v, 1.5% w/v, 1.75% w/v, 2% w/v, and commercially available A10 Blood Agar Plate (Hardy Diagnostics) after 2.5 hours of incubation at 37° C. The images are presenting Dark-field images of the seeded American Type Culture Collection (ATCC) strains and hospital clinical isolates (MSH) of Gram-positive (*Staphylococcus Aureus* SA ATTC 25923, *Enterococcus Faecalis* EF ATTC 51299, *Staphylococcus Epidermidis* SE ATTC 12228) and Gram-negative (*Escherichia coli* EC ATTC 35218, *Klebsiella Pneumoniae* KP CRE MSH 1705, *Proteus Mirabilis* PM ATTC 12453) bacteria, as imaged by an upright reflected-illumination bright-field (BF) & dark-field (DF) microscope with 10× objective.
Figure 5C:
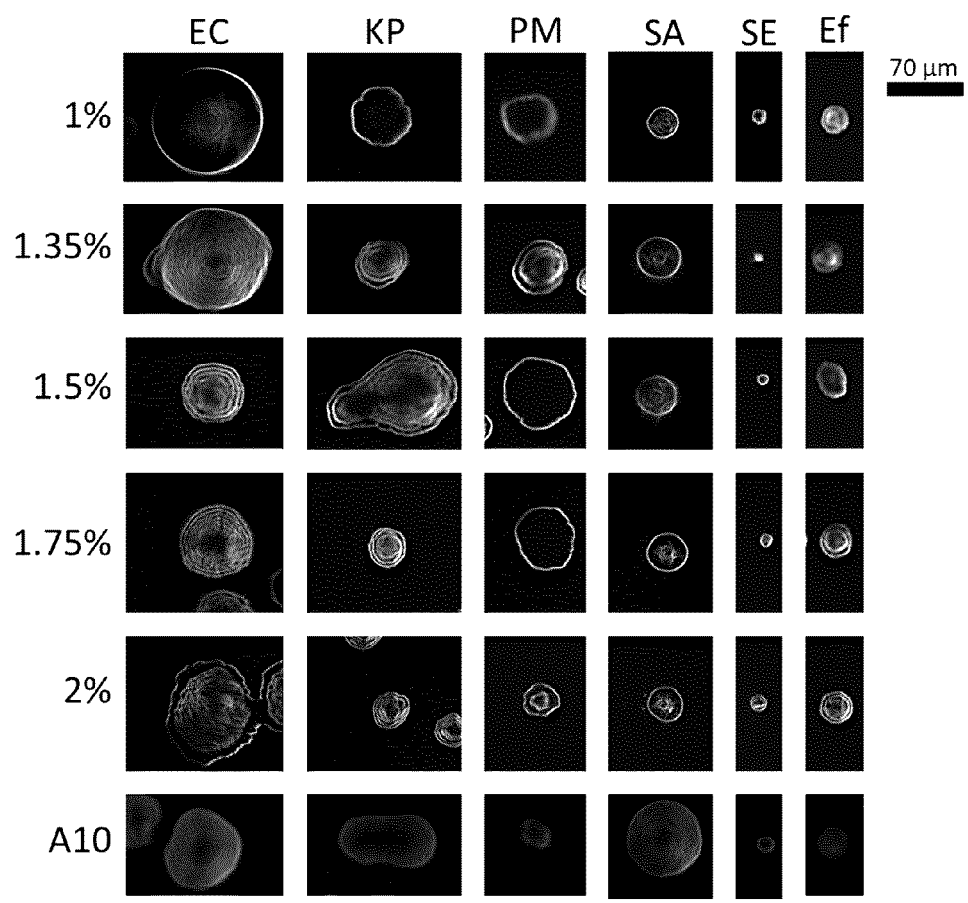
FIG. 5C presents a qualitative comparison of the microcolonies grown on the selected freshly prepared solid-phase growth media with respective agar concentrations of 1% w/v, 1.35% w/v, 1.5% w/v, 1.75% w/v, 2% w/v, and commercially available A10 Blood Agar Plate (Hardy Diagnostics) after 3.5 hours of incubation at 37° C. The images are presenting dark-field images of the seeded American Type Culture Collection (ATCC) strains and hospital clinical isolates (MSH) of Gram-positive (*Staphylococcus Aureus* SA ATTC 25923, *Enterococcus Faecalis* EF ATTC 51299, *Staphylococcus Epidermidis* SE ATTC 12228) and Gram-negative (*Escherichia coli* EC ATTC 35218, *Klebsiella*
Figure 5D:
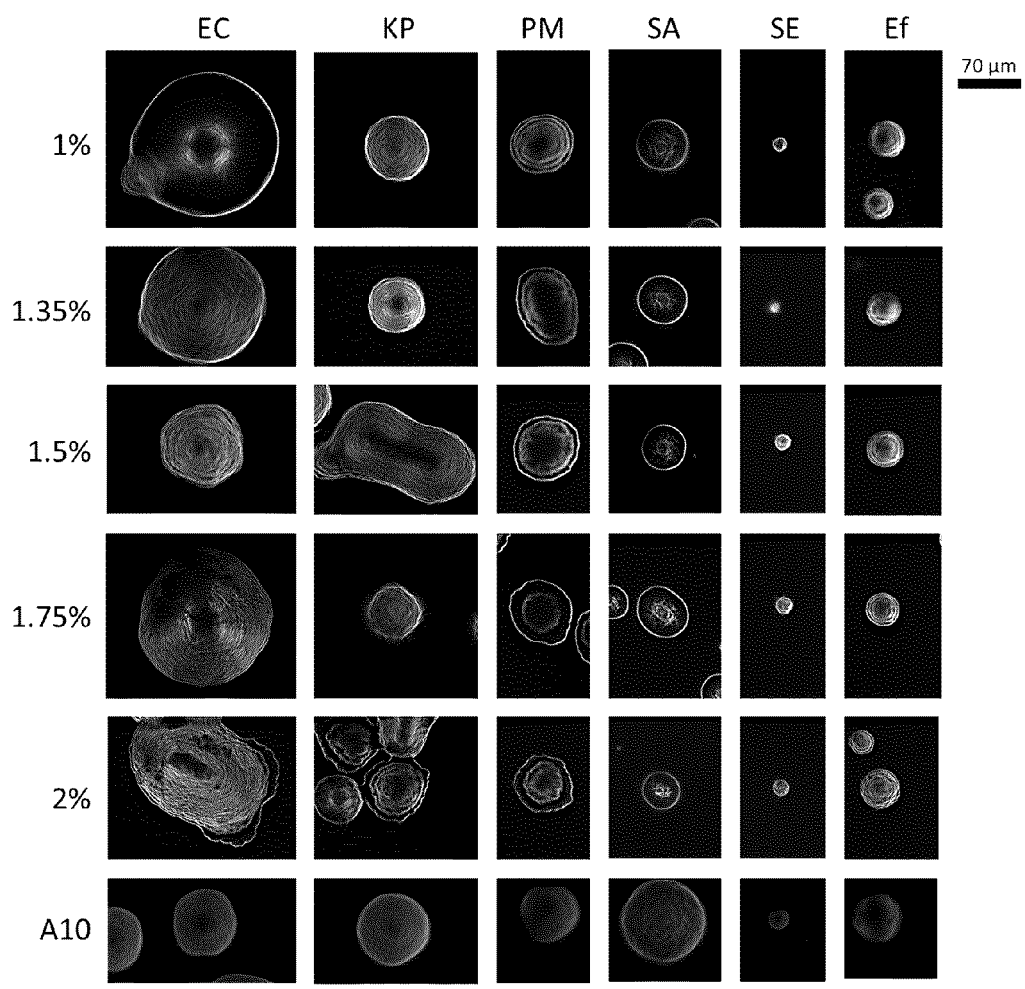

FIG. 5D presents a comparison of the microcolonies grown on solid-phase growth media with respective agar concentrations of 1% w/v, 1.35% w/v, 1.5% w/v, 1.75% w/v, 2% w/v, and commercially available A10 Blood Agar Plate (Hardy Diagnostics) after 4.5 hours of incubation at 37° C. The images are presenting dark-field images of the seeded American Type Culture Collection (ATCC) strains and hospital clinical isolates (MSH) of Gram-positive (*Staphylococcus Aureus* SA ATTC 25923, *Enterococcus Faecalis* EF ATTC 51299, *Staphylococcus Epidermidis* SE ATTC 12228) and Gram-negative (*Escherichia coli* EC ATTC 35218, *Klebsiella Pneumoniae* KP CRE MSH 1705, *Proteus Mirabilis* PM ATTC 12453) bacteria, as imaged by an upright reflected-illumination dark-field microscope with 10× objective.

Figure 5E:
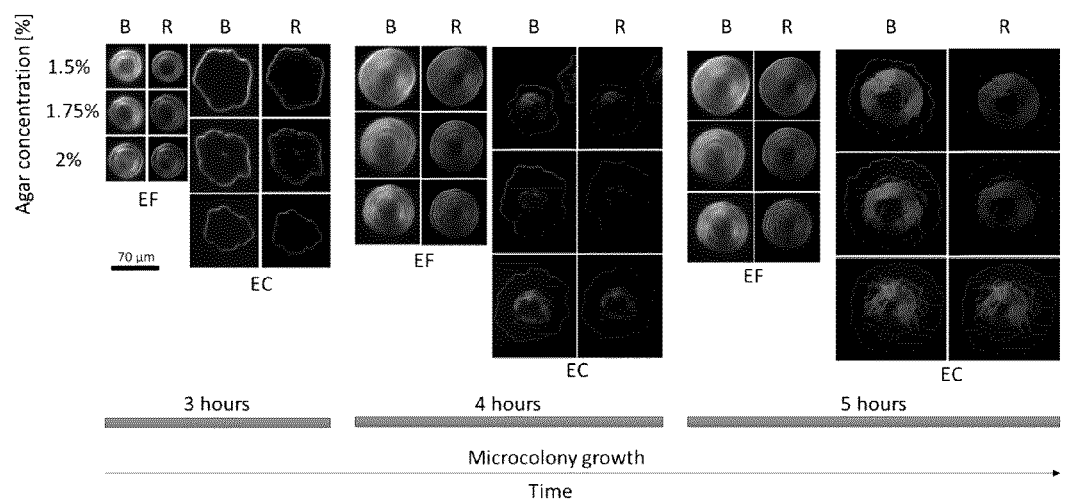

FIG. 5E presents a comparison of the microcolonies grown on solid-phase growth media with the respective agar concentrations of 1.5% w/v, 1.75% w/v, and 2% w/v. The images are presenting the dark-field images of Gram-negative bacteria *Enterococcus Faecalis* and Gram-positive bacteria *Escherichia coli*, as imaged by an upright reflected-illumination dark-field microscope with 10× objective. The microscope is epi-illuminated by a blue LED light (B) and red LED light (R).

Figure 6A:
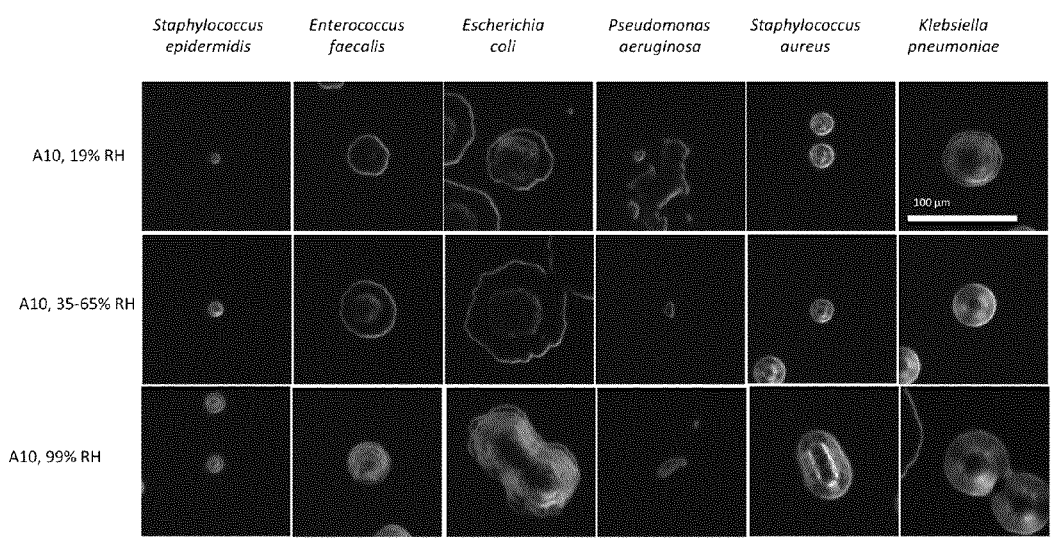

FIG. 6A shows dark-field images of *Staphylococcus epidermidis* SE ATTC 12228, *Enterococcus faecalis* EF ATTC 35667, *Escherichia coli* EC ATTC 35218, *Pseudomonas aeruginosa* PA ATTC 35554, *Staphylococcus aureus* SA ATTC 25923, *Klebsiella pneumoniae* KP ATTC 700603 microcolonies formed on a commercially available solid-phase growth medium A10 Blood Agar Plate (Hardy Diagnostics) and imaged by an upright reflected-illumination dark-field microscope with 7.5× objective after 3 hours of incubation at 35° C. and three selected relative humidity settings (RH 19%, RH 35-65%, RH 99%).

Figure 6B:
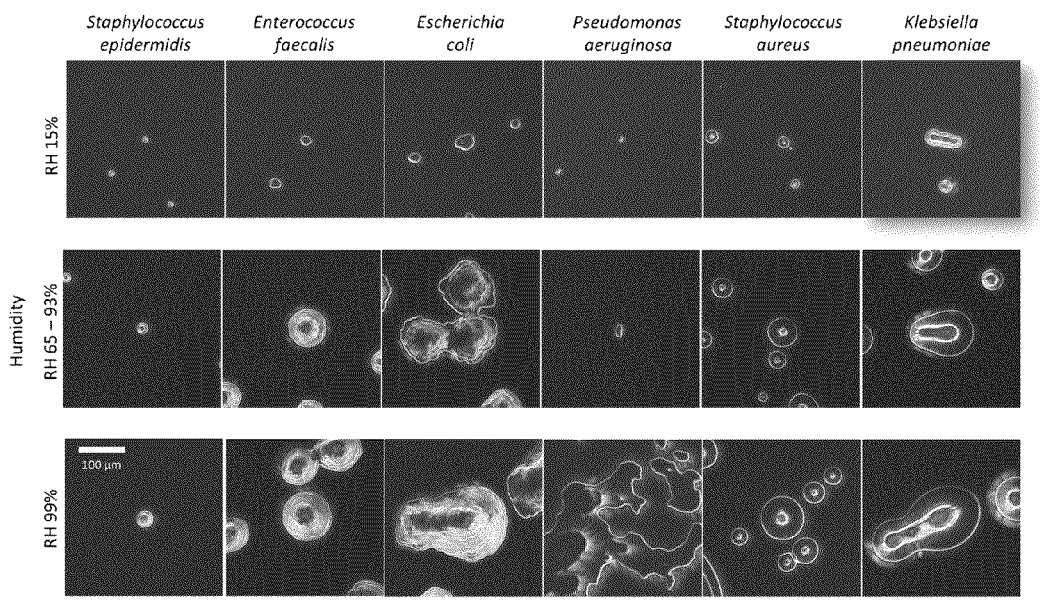

FIG. 6B shows dark-field images of *Staphylococcus epidermidis* SE ATTC 12228, *Enterococcus faecalis* EF ATTC 35667, *Escherichia coli* EC ATTC 35218, *Pseudomonas aeruginosa* PA ATTC 35554, *Staphylococcus aureus* SA ATTC 25923, *Klebsiella pneumoniae* KP ATTC 700603 microcolonies formed on a solid-phase growth medium with 1.75% agar concentration and imaged by an upright reflected-illumination dark-field microscope with 7.5× objective after 3.5 hours of incubation at 35° C. and three selected relative humidity settings (RH 15%, RH 65-93%, RH 99%).

Figure 7A:
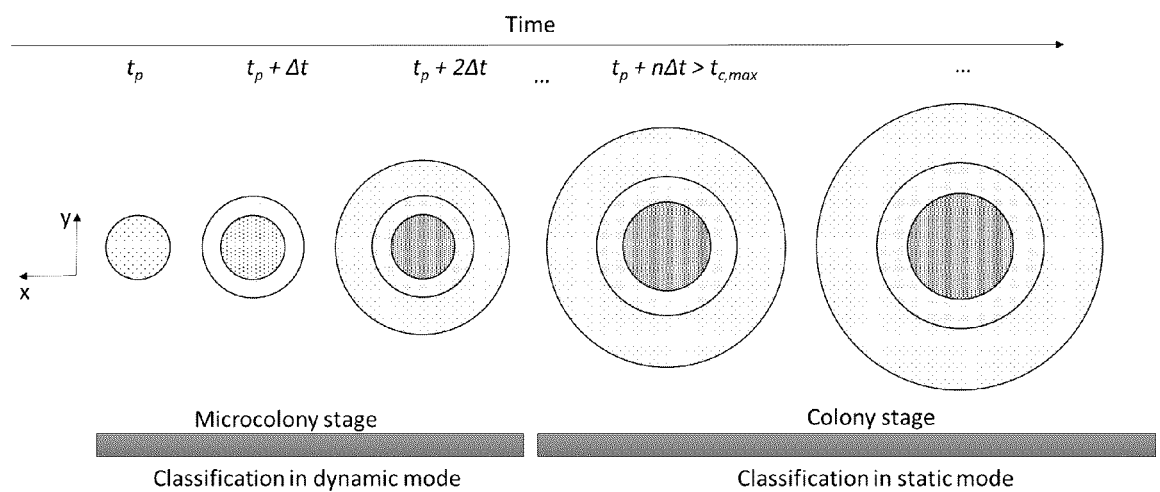

FIG. 7A schematically represents the evolution of microbial colony from the microcolony stage to mature colony stage (labelled Colony stage).

Figure 7B:
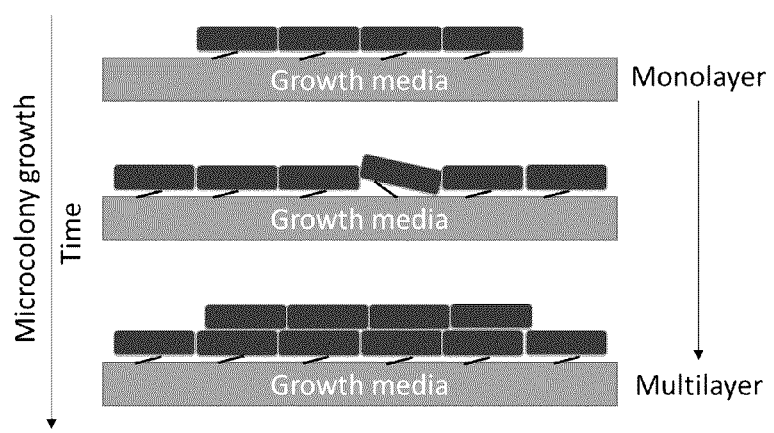

FIG. 7B schematically represents model of the transition from the monolayer microcolony to the (semi)multilayer microcolony via local pressure from the neighboring cells.

Figure 7C:
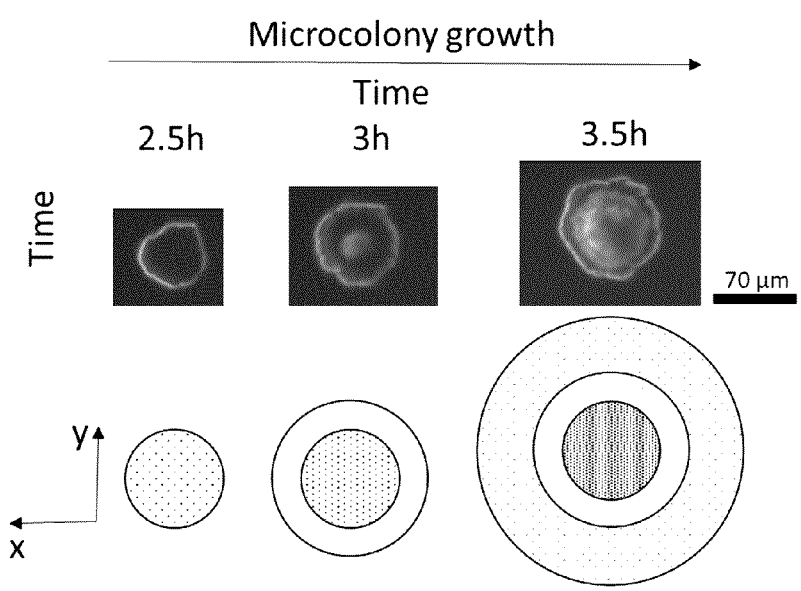

FIG. 7C schematically represents architecture of the microcolony that contains a series of concentric rings.

Figure 8A:
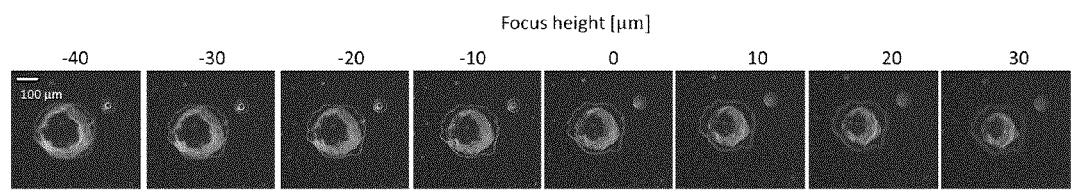

FIG. 8A shows dark-field images of *Escherichia coli* (EC) and *Staphylococcus aureus* (SA) microcolonies formed on a solid-phase growth medium with 1.75% agar concentration, grown from a treated whole blood sample, and imaged by an upright reflected-illumination dark-field microscope with 7.5× objective after 3 hours of incubation at 35° C. and 43% relative humidity. The image sequence from left to right are taken at progressively higher distance from the optimal focus based on the autofocusing routine by an amount of 10 um: −40 µm, −30 µm, −20 µm, −10 µm, 0 µm (optimal focus based on the autofocusing routine), 10 µm, 20 µm, 30 µm.

Figure 8B:
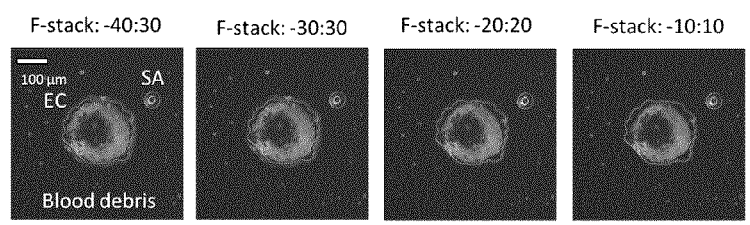

FIG. 8B presents post-processed images with F-stack: −40:40 image combines 8 individual images within the given range, F-stack: −30:30 image combines 7 individual images, F-stack −20:20 image combines 5 individual images, and F-stack −10:10 image combines 3 individual images.

Figure 8C:
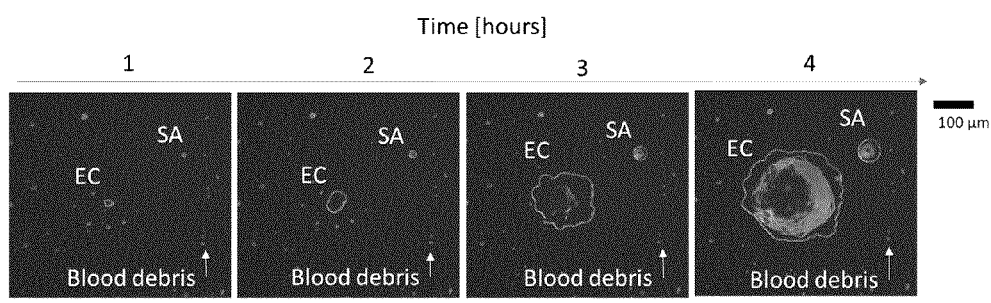

FIG. 8C shows the F-stack joined images corresponding to the images presented in FIG. 8B at 4 different incubation times.

Figure 9A:
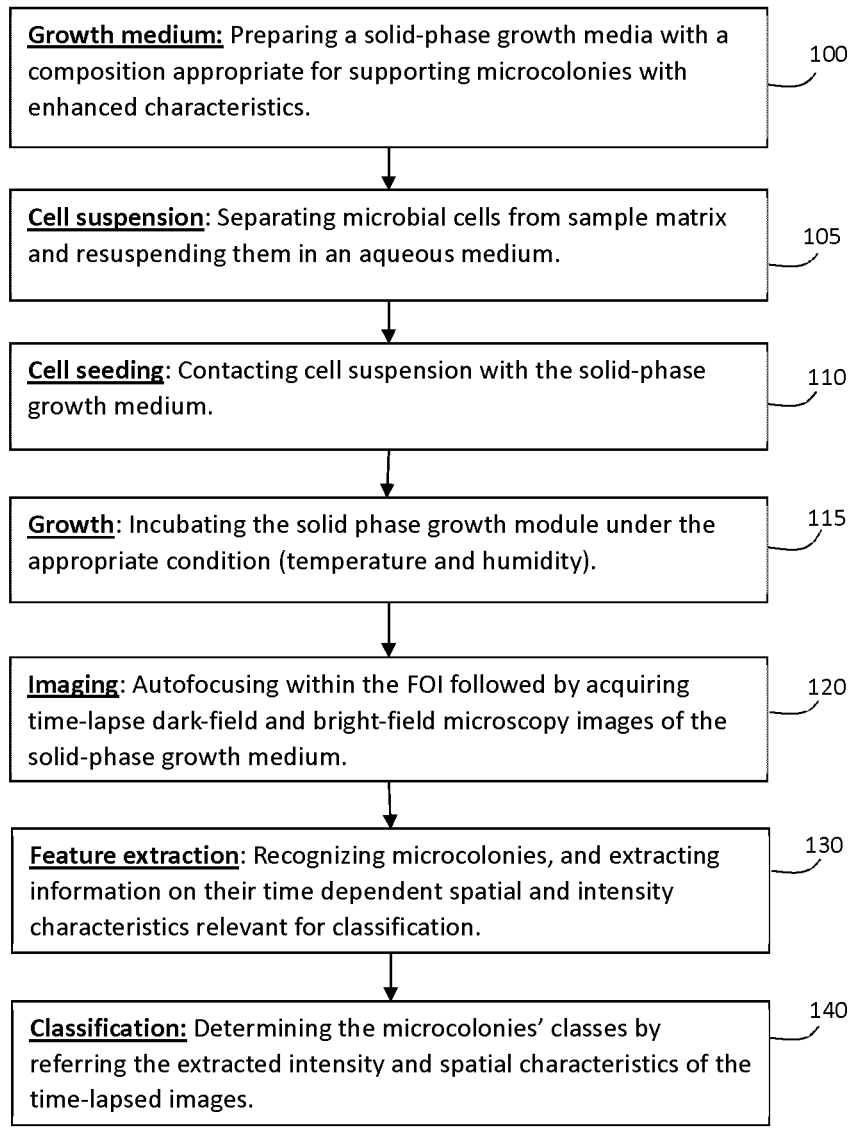

FIG. 9A is a flowchart representing the steps for performing classification on the microbial content of a biological sample.

Figure 9B:
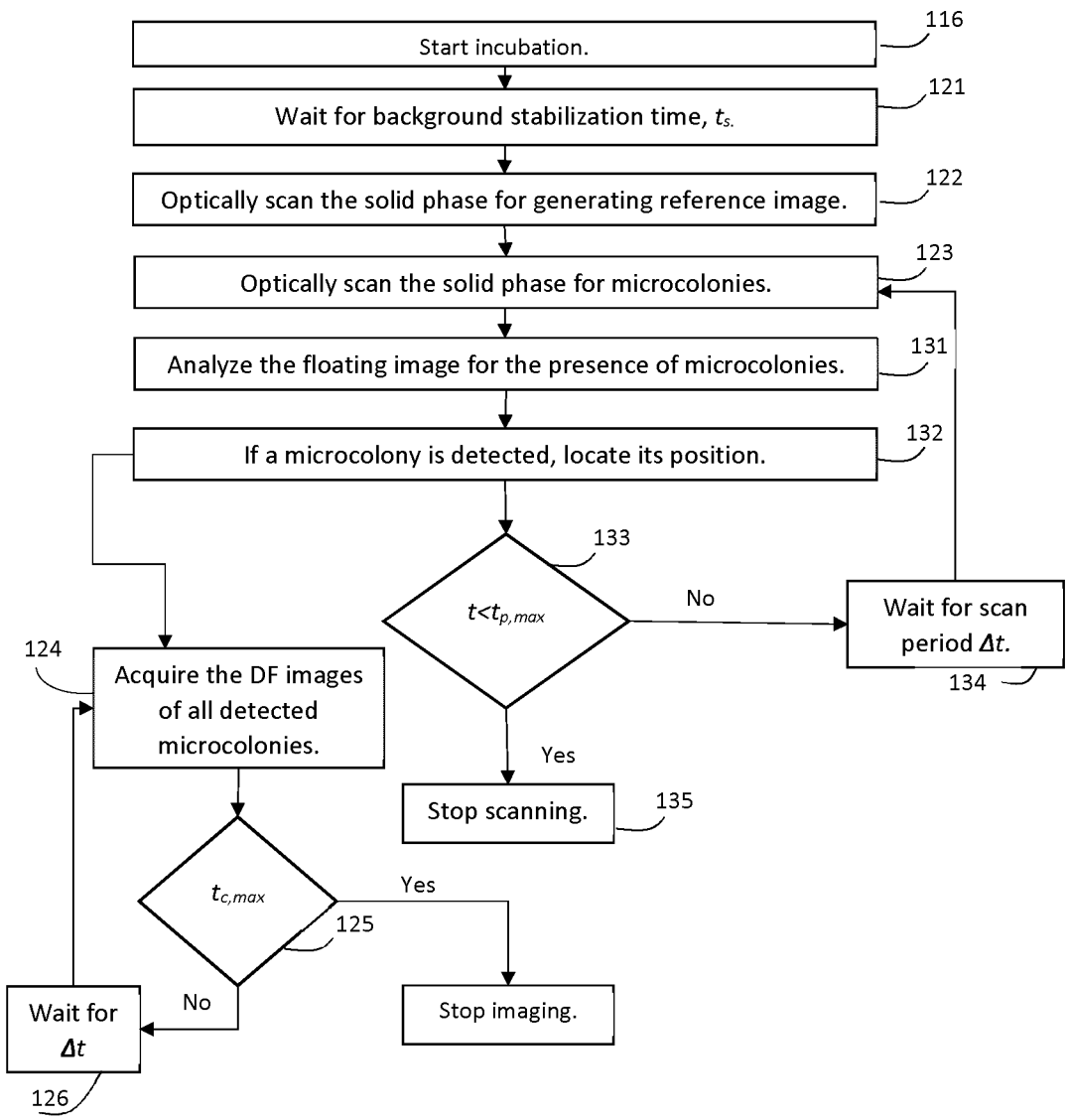

FIG. 9B is a flowchart representing the steps for classifying the microbial content of a biological sample (FIG. 9A steps 120-140).

FIG. 10 is a table presenting the number of positive microcolonies at a given incubation time of the selected ATCC strains of Gram-positive and Gram-negative bacteria, recovered from spiked treated whole blood sample.

Figure 11A:
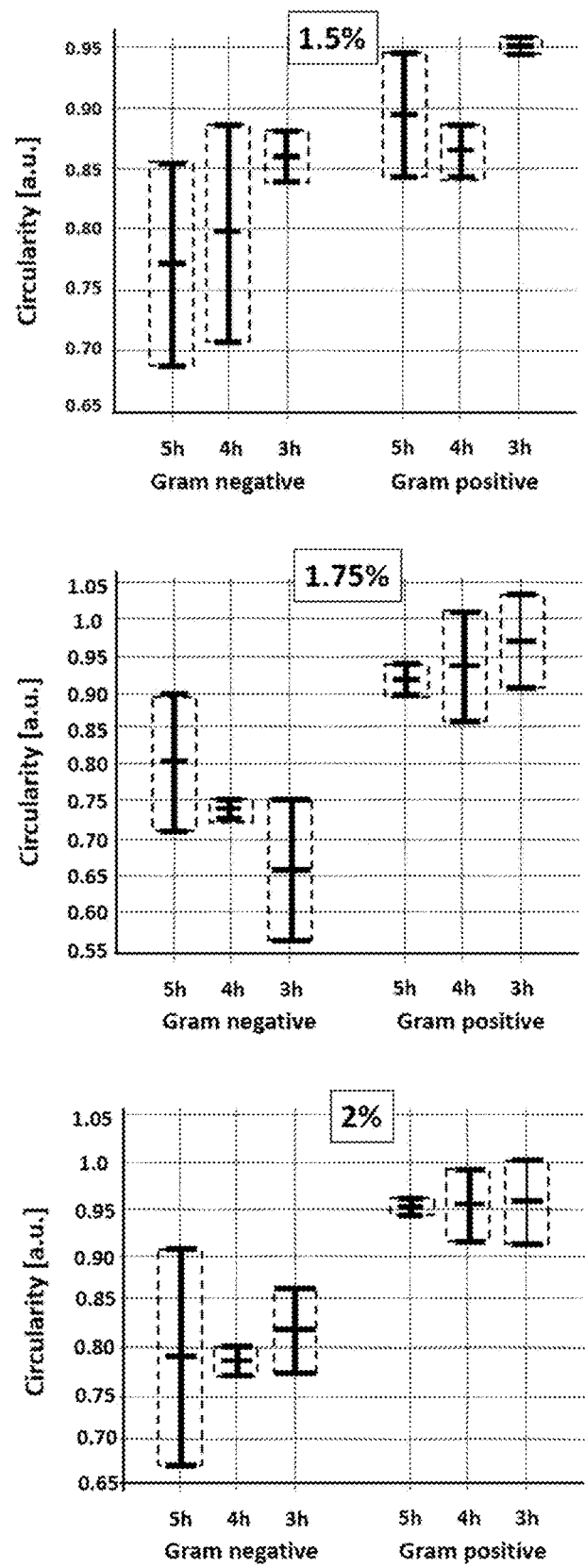

FIG. 11A presents a quantitative comparison of the circularity of the Gram-positive and Gram-negative microcolonies grown on solid-phase growth media with the respective agar concentrations of 1.5% w/v, 1.75% w/v, and 2% w/v. The graphs are presenting the measured circularity of the microcolonies from the dataset with the most typical from the dataset shown in FIGS. 5B-5D.

Figure 11B:
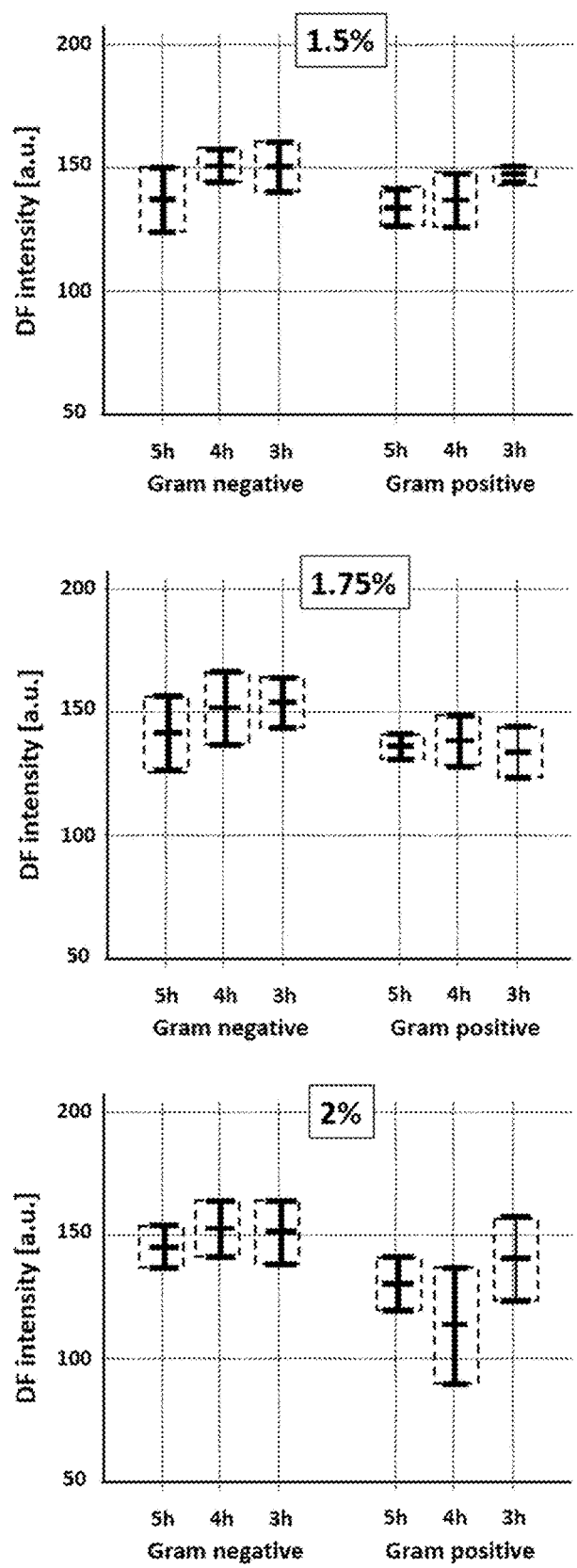

FIG. 11B presents a quantitative comparison of the dark-field (DF) intensity of the Gram-positive and Gram-negative microcolonies grown on solid-phase growth media with the respective agar concentrations of 1.5% w/v, 1.75% w/v, and 2% w/v. The graphs are presenting the measured dark-field (DF) intensity of the microcolonies from the dataset with the most typical from the dataset shown in FIGS. 5B-5D.

FIG. 11C presents biplots of the characteristic features of the microcolonies grown on solid-phase growth media with the respective agar concentrations of 1.5% w/v, 1.75% w/v, and 2% w/v after 4 hours of incubation at 37° C.

Figure 12A:
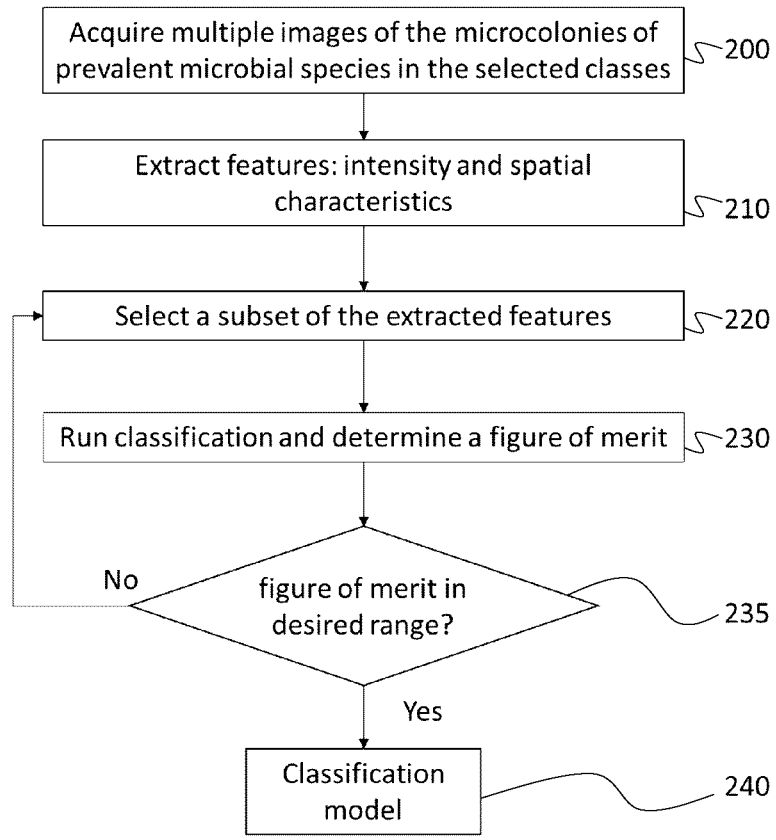

FIG. 12A is a flowchart representing the steps for preparing "classification model".

Figure 12B:
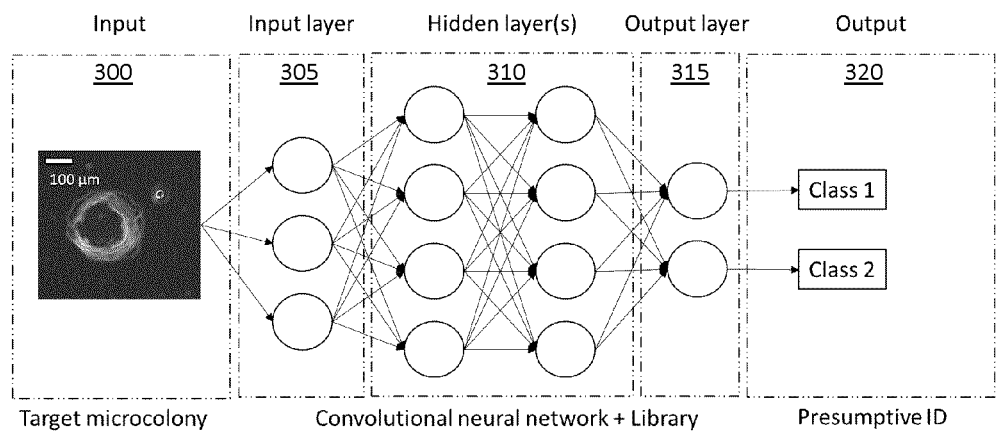

FIG. 12B is a flowchart representing a basic structure of convolutional neural network (CNN) as an example implementation of the "classification model" of FIG. 12A.

Figure 12C:
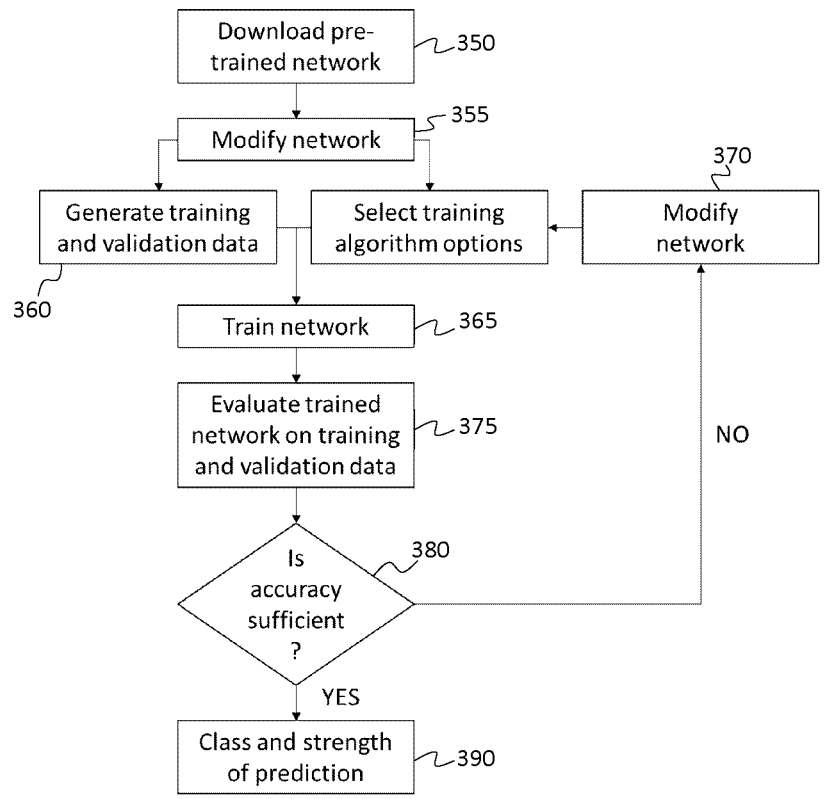

FIG. 12C is a flowchart representing a basic workflow for building "classification model" of FIG. 12A based on pre-trained convolutional neural network (CNN).

Figure 13:
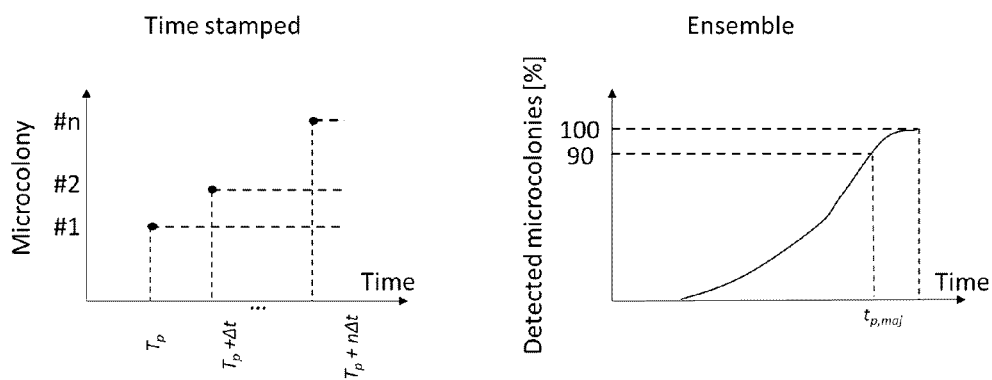

FIG. 13 schematically represents the appearance (detection/positivity) of microcolonies from a population of similar microbial cells seeded on a solid-phase growth media. On the left image entitled 'Time stamped' approach, the time-lapse DF images of each microcolony are recorded individually during the time interval between its emergence and a preselected maximum time. The right image entitled 'Ensemble' approach represents a case when the number of the detected microcolonies reach to a level close to the expected level (e.g., 90%) and then the dark-field image of each microcolony is recorded.

Figure 14A:
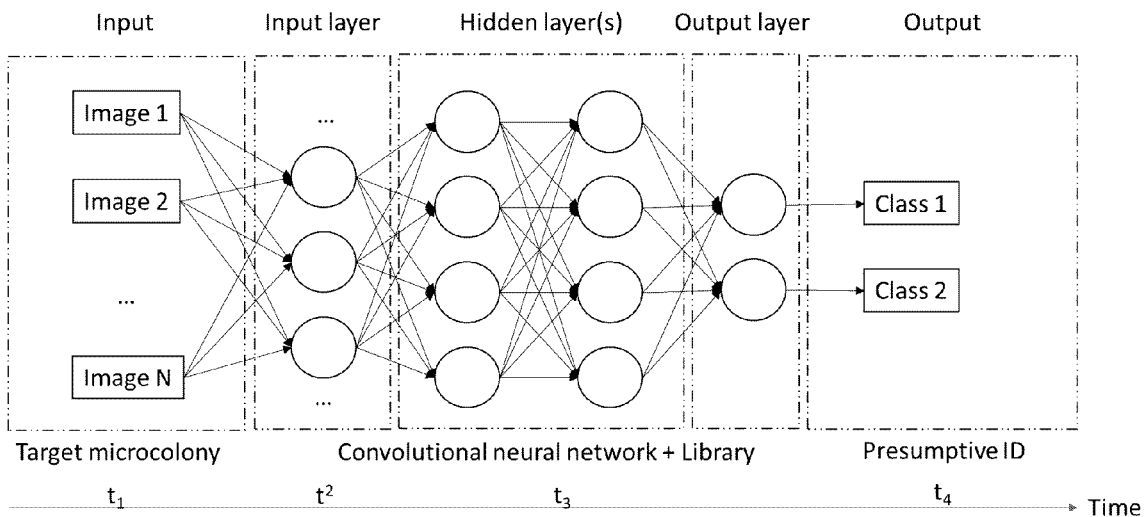

FIG. 14A is a flowchart representing a basic CNN structure for time series analysis as an example implementation of the "classification model" of FIG. 12A.

Figure 14B:
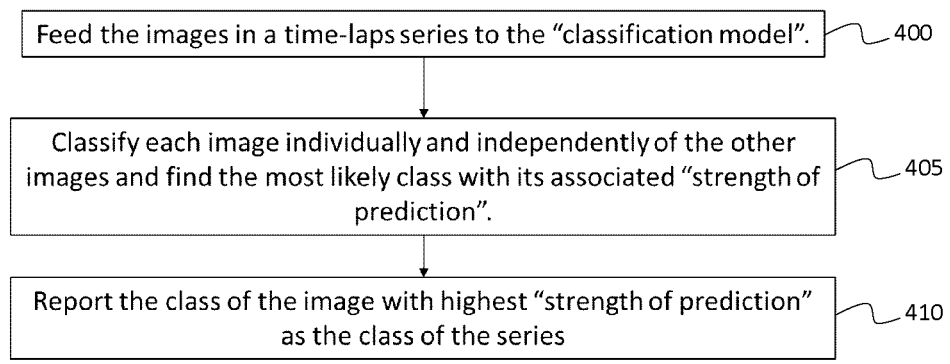

FIG. 14B presents a basic workflow for the bacterial classification: based on "single frame" analysis method.

Figure 14C:
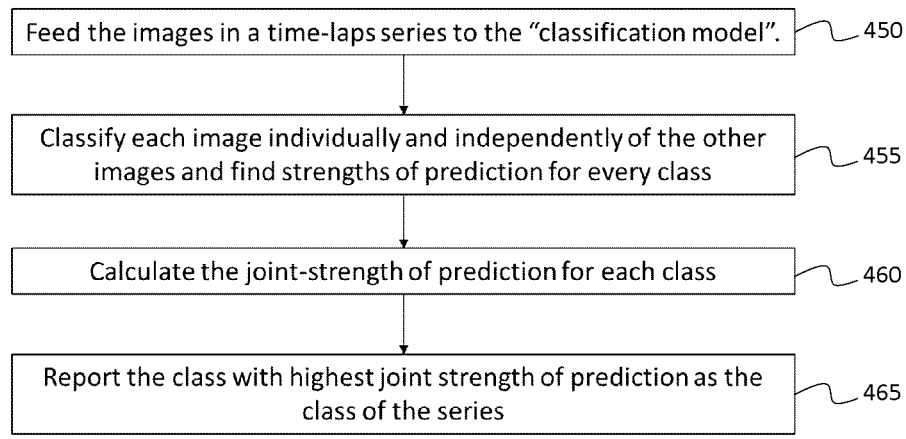

FIG. 14C presents a basic workflow for the bacterial classification: based on "joint probability" method.

Figure 14D:
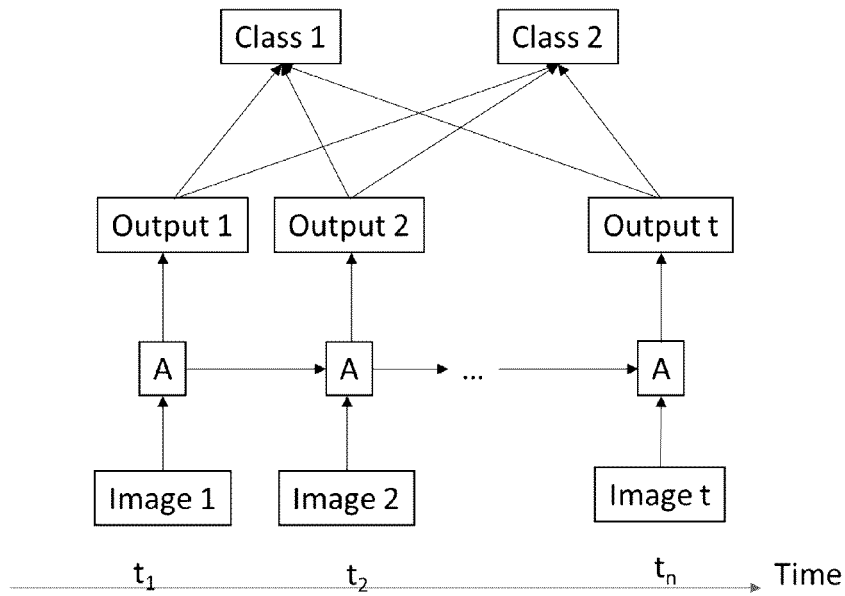

FIG. 14D is a flowchart representing a basic structure of RNN for time series analysis as an example implementation of the "classification model" of FIG. 12A.

Figure 14E:
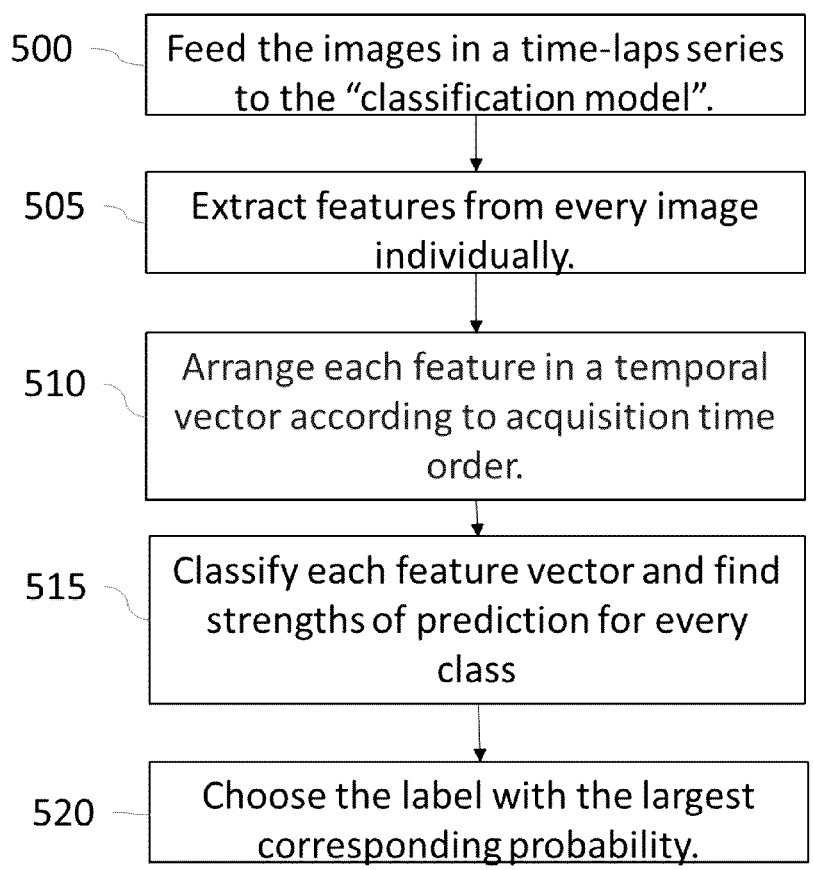

FIG. 14E presents a basic workflow for the bacterial classification: based on Recurrent Neural Network method.

Figure 14F:
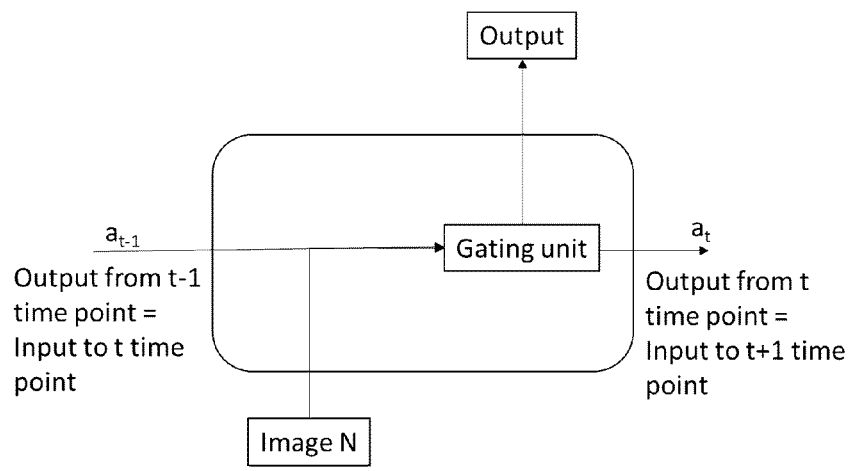

FIG. 14F is a flowchart representing a basic structure of LSTM for time series analysis as an example implementation of the "classification model" of FIG. 12A.

Figure 14G:
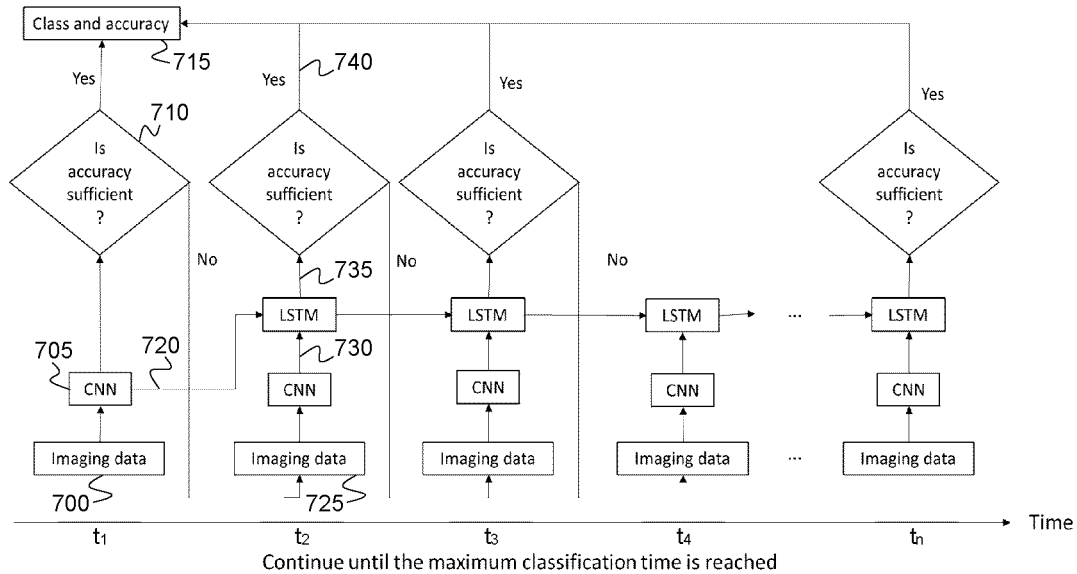

FIG. 14G presents a basic workflow for the bacterial classification: based on CNN-LSTM method.

Figures 15A, 15B:
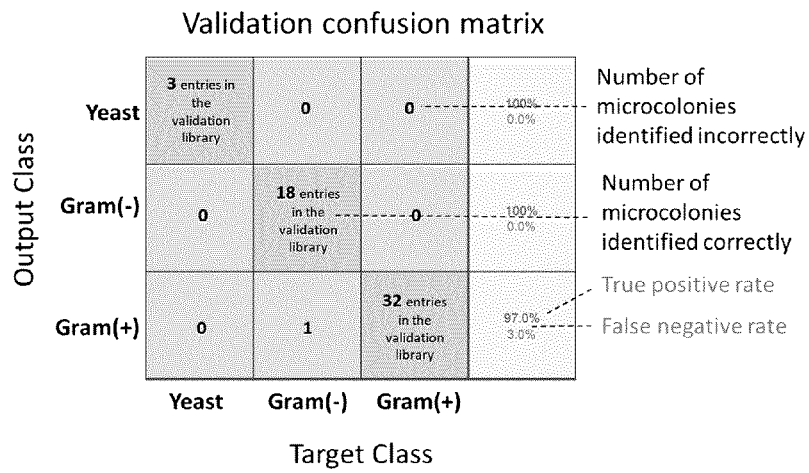

FIG. 15A presents a confusion matrix for the CNN-LSTM classification down to Gram stain level.

FIG. 15B is a list of Gram-positive organisms included into classification library.

FIG. 15B is a list of Gram-negative organisms included into classification library.

FIG. 15C is a list of Yeast organisms included into classification library.

Figure 16:
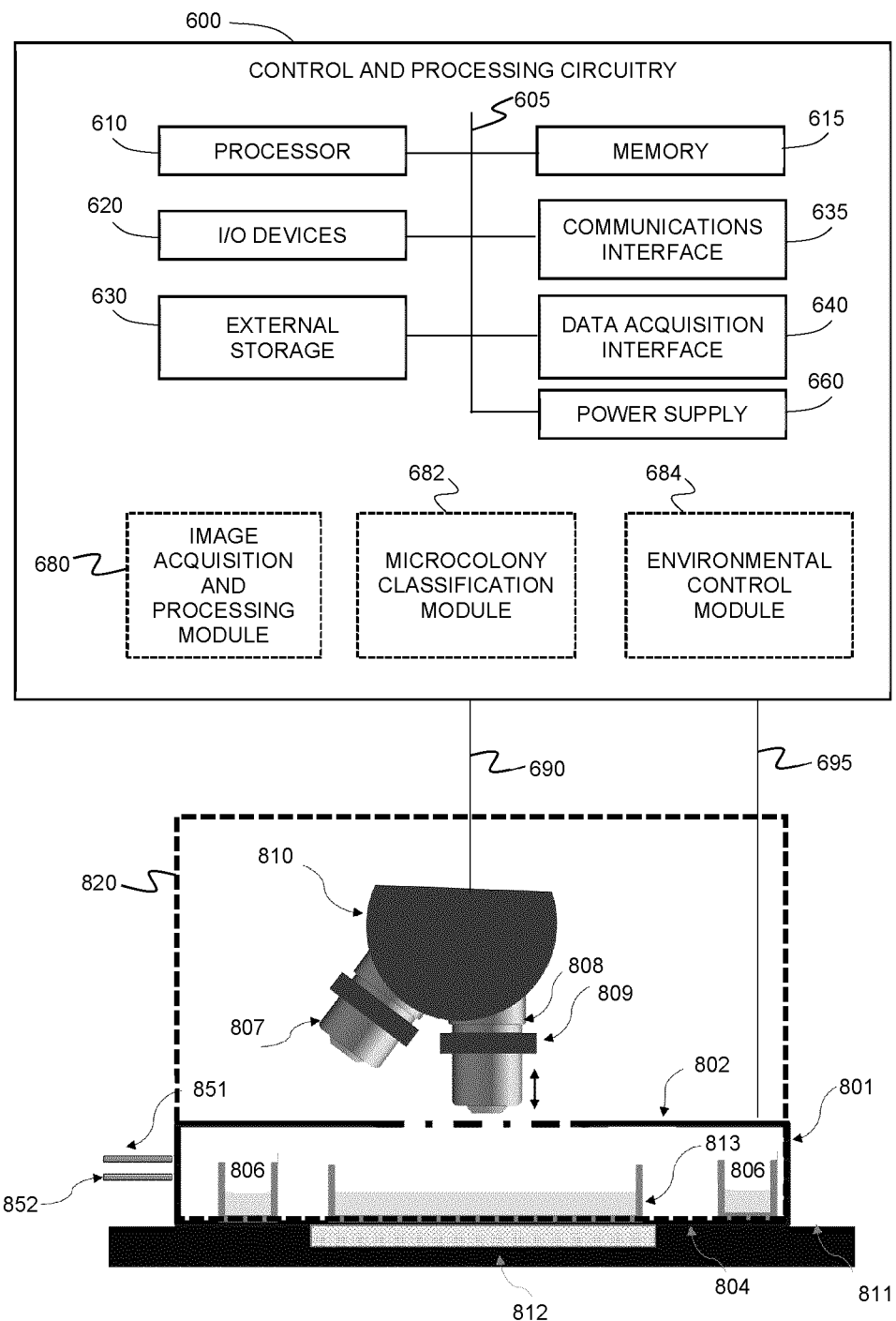

FIG. 16 schematically illustrates an example system for monitoring the growth of microbial cells on a solid-phase growth medium, detecting presence of viable microbial microcolonies and classifying the cells as belonging to a given microbial cell class.

Figure 17:
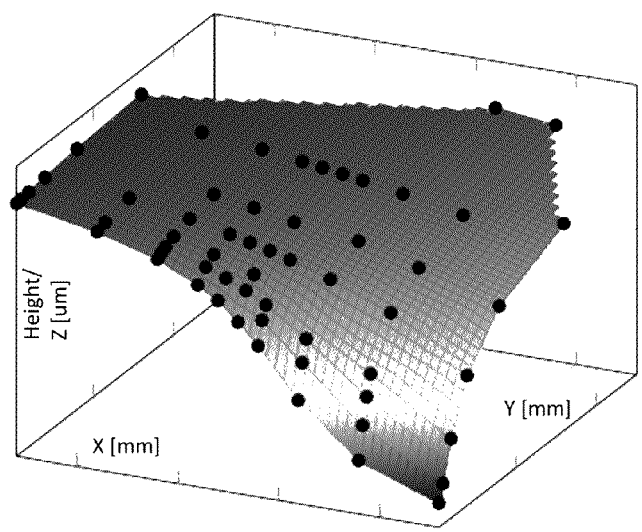

FIG. 17 schematically illustrates the surface profiling method before launching the actual image acquisition procedure, with selected points on the solid-phase growth medium surface being imaged with employing autofocusing, and fitting a mathematical function to the determined points the surface profile of solid-phase growth medium is generated.

Figure 18A:
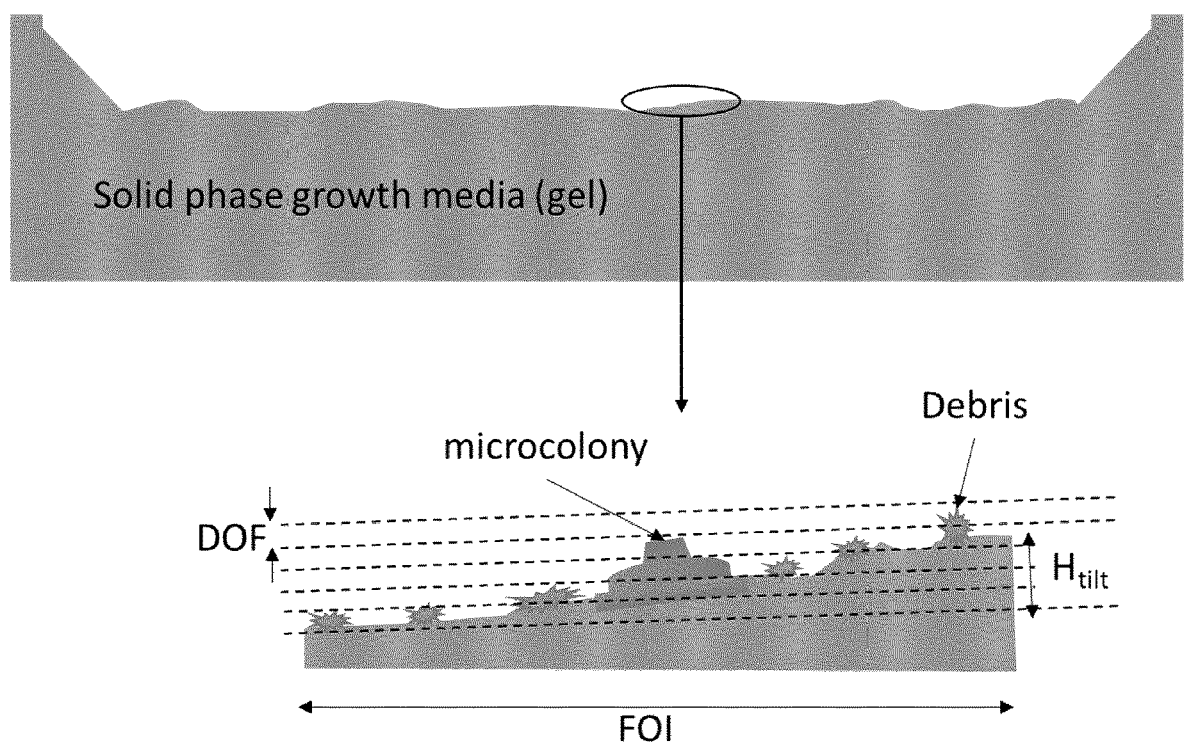

FIG. 18A schematically illustrates the complex topology of the solid-phase growth media (top) with zoom-in part (down) showing microcolony alongside blood debris on a non-flat surface of a solid-phase growth medium.

Figure 18B:
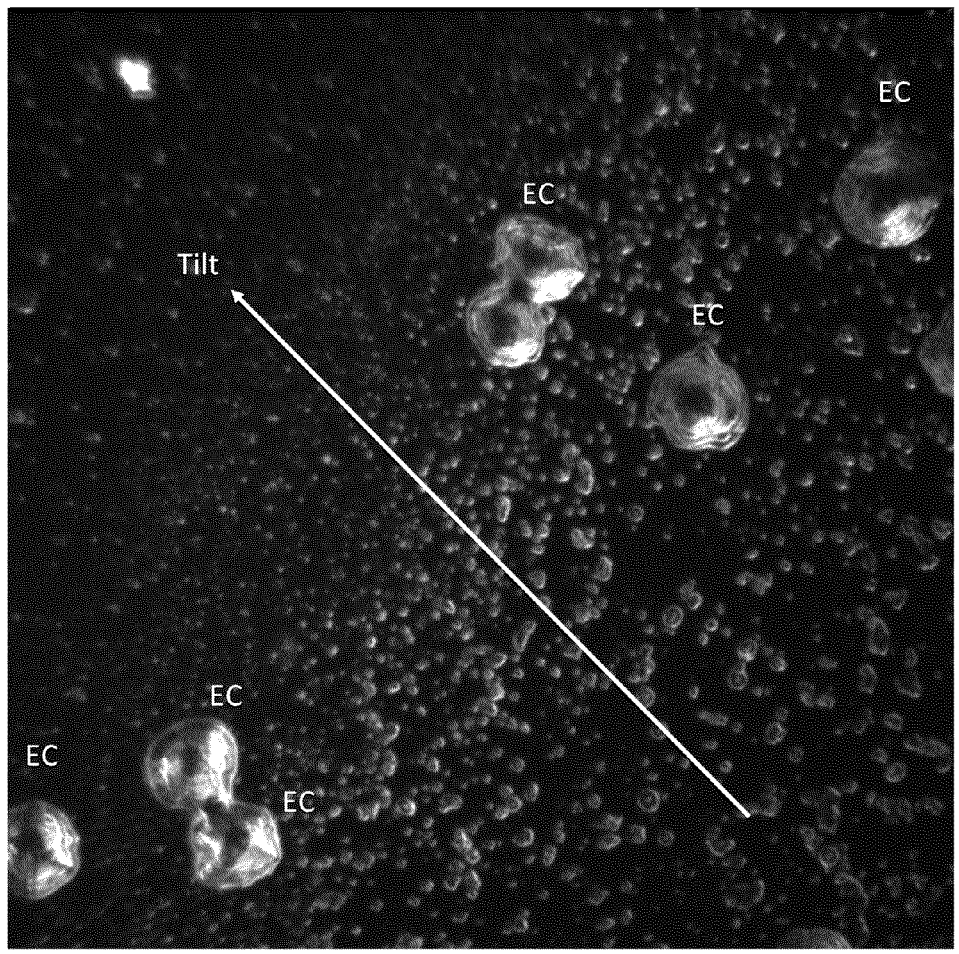

FIG. 18B shows dark-field image of *Escherichia coli* ATTC 35218 microcolonies formed on a solid-phase growth medium with 1.75% agar concentration, grown from a treated whole blood sample, and imaged by an upright reflected-illumination dark-field (DF) microscope with 10× objective after 3 hours of incubation at 35° C. Field-of-image (FOI)=0.42 mm. The label EC indicates microcolonies and the surface has a tilt along the diagonal indicated by the arrow.

Figure 18C:
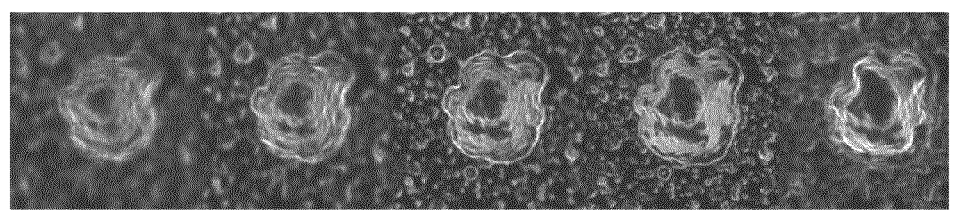

FIG. 18C shows a zoomed part of a dark-field image of *Escherichia coli* microcolony formed on a solid-phase growth medium with 1.75% agar concentration, grown from a treated whole blood sample, and imaged by an upright reflected-illumination dark-field microscope with 7.5× objective after 2 hours of incubation at 35° C. and relative humidity (RH) of 42%. The image sequence from left to right are taken at progressively higher distance from the solid-phase growth medium surface by an amount of 20 um.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprise" and "comprising" are to be construed as being inclusive and open ended, and not exclusive. Specifically, when used in the specification and claims, the terms "comprise" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25% or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art.

As used herein, the phrase "intact cell" refers to a microbial cell containing nucleic acids, proteins or intracellular contents of interest, where the microbial cell is separable via a separation method such as, but not limited to, centrifugal separation, filtration, microfluidic separation, or immunomagnetic separation.

As used herein, the phrase "sample" refers to a liquid or suspension that contains, may contain, or is suspected of containing one or more microbial cells. Non-limiting examples of samples include body fluids such as urine, lymph fluid, cerebrospinal fluid, blood (e.g., whole blood, blood culture, and plasma), sputum and saliva. Other examples of samples include homogenized tissue suspensions, including, but not limited to, stool, homogenized suspensions of muscle tissue, brain tissue and liver tissue. A sample may be processed or unprocessed and may optionally include one or more reagents or growth media. In the case of a blood culture sample (a sample containing growth media and whole blood), the blood culture sample may be a blood culture sample having been deemed positive for the presence of microbial cells via a detection modality (e.g. via an automated blood culture system), a mid-culture blood culture sample for which the presence of microbial cells is suspected based on measurements made via one or more mid-culture detection modalities, or mid-culture blood culture sample for which no initial detection results are available.

As used herein, the phrase "blood cells" refers to mammalian cells present in blood, including, but not limited to, red blood cells (erythrocytes), white blood cells (leukocytes) and blood platelets (thrombocytes).

As used herein, the phrase "blood sample" refers to any sample comprising one or more blood cells. Non-limiting examples of blood samples include whole blood samples, blood culture samples, buffy coat samples and platelet samples.

As used herein, the phrase "whole blood" or "whole blood sample" refers to mammalian blood comprising blood plasma and blood cells. "Whole blood" or "a whole blood sample" may include one or more reagents, such as anticoagulation reagents. For example, whole blood may be collected in a sample bottle that may include one or more reagents such as, but not limited to, anticoagulants including SPS (sodium polyanethole sulfonate), EDTA (ethylenediaminetetraacetic acid), sodium citrate and heparin.

As used herein, the phrase "selective lysis" refers to a blood lysis reagent or lysis process whereby the fraction of microbial cells that remain viable following lysis exceeds the fraction of eukaryotic cells that remain viable following lysis, where the eukaryotic cells are associated with the subject from which the sample was collected.

As used herein, the phrase "blood debris" refers to particles which are transferred to the final cell suspension after treating a blood sample.

As used herein, the phrases "microbial cell" and "microorganism" comprises bacteria (e.g., Gram-positive and Gram-negative bacteria, as well as bacterial spores) and unicellular fungi (such as yeast and molds).

As used herein, the phrase "eukaryotic cell" refers to cells originating from a eukaryotic organism excluding fungi, such as animals, in particular animals containing blood, comprising invertebrate animals such as crustaceans and vertebrates. As used herein, "vertebrates" comprise both cold-blooded animals (fish, reptiles, amphibians) and warm-blooded animals (birds and mammals).

As used herein, the phrase "effective buffer concentration", when used with reference to a mixture formed by mixing a volume of a sample with a volume of a blood lysis reagent, where the blood lysis reagent includes a buffer system, refers to the product of the buffer concentration of the blood lysis reagent and a ratio formed by dividing the volume of the blood lysis reagent by the sum of the volume of the blood lysis reagent and the volume of the sample. The effective buffer concentration represents the contribution of the blood lysis reagent to the buffer system in the final mixture (i.e., the dilution factor applied to the buffer concentration of the blood lysis reagent) and may be different than the actual buffer concentration in the final mixture due to buffering components present in the sample.

As used herein, the phrase "separation process" refers to a process suitable for separating and optionally concentrating microbial cells. Non-limiting examples of separation processes include centrifugation, filtration, immunomagnetic separation and microfluidic separation.

As used herein, the phrase "cell suspension" refers to an aqueous medium that contains microbial cells.

As used herein, the terms "colony" and "microcolony" refer to a multiplicity or population of microorganisms that lie in close proximity to each other, that lie on a surface, and that are the clonal descendants, by in situ replication, of a single ancestral microorganism. In general, a "colony" is visible to the human eye and is typically greater than about 50 µm, 60 µm, 80 µm, 100 µm, or 200 µm in diameter. However, as used herein, unless otherwise stated, the term "colony" is meant to include both colonies having a diameter of 200 µm or more, and the term "microcolony" is meant to refer to a colony having a diameter less than 200 µm.

A significant shortcoming of convention approaches to performing antimicrobial susceptibility testing is long delay before results are available. This long delay typically leads to results that have epidemiological value as opposed to direct clinical value, with most antimicrobial treatment decisions been made empirically prior to the availability of results. While many have attempts have been made to provide rapid molecular solutions, antimicrobial susceptibility testing is an inherently phenotypic process. Accordingly, the present inventors have sought methods that facilitate rapid and clinically actionable antimicrobial susceptibility testing based on microcolony growth, detection and monitoring, and antimicrobial testing of harvested colonies.

Such methods are described in co-pending International Patent Application No. PCT/CA2019/051895, titled "SYSTEMS AND METHODS FOR MICROCOLONY GROWTH AND MICROBIAL CELL CHARACTERIZATION" and filed on Dec. 20, 2019, which is incorporated herein by reference in its entirety. International Patent Application No. PCT/CA2019/051895 describes a phenotypic workflow in which microcolonies are grown on a solid-phase growth medium, optically detected, and optically monitored. After a given microcolony has reached a sufficient size (or after a sufficient time duration of growth and incubation), a microcolony is harvested and employed for antimicrobial susceptibility testing.

Enhanced Microcolony Morphology in Dark-Field Microscopy Images

While the preceding methods described in International Patent Application No. PCT/CA2019/051895 provided various example means for performing presumptive classification of microcolonies, the present inventors sought to further extend these methods in order to provide improved rapid morphology- and morphodynamic-based classification of microcolonies. Experiments were performed involving the use of both bright-field and dark-field time-lapse and single-frame microscopy images for microcolony detection, monitoring and classification. *Enterobacter cloacae* complex ECC ATCC 13047, *Enterococcus faecalis* EF ATCC 51299 and *Staphylococcus haemolyticus* SH ATCC 29970 microcolonies were formed on solid-phase growth media residing on a plate. The solid-phase growth media contained 1.35% w/v of agar and growth components (pancreatic digest of casein, peptic digest of soy bean meal, NaCl, and defibrinated sheep blood) and was prepared according to the method of Example 2.

One µL of microbial cell suspension, obtained by processing whole blood according to the method of Example 1, was dispensed on the solid-phase growth media and allowed to air dry before obtaining the microscopic image. The plate was incubated at 35° C. for 4.5 hours after seeding and the area was scanned with bright-field objective and a dark-field objectives having different magnifications. Imaging was performed using a metallurgical/reflected microscope with epi-illumination by a halogen lamp and coupled to a monochrome camera having a pixel size of 2.4×2.4 µm. The acquired imaging data was registered with respect to 20×: 10× was resized two times and 5× was resized four times.

When the present inventors performed experiments to evaluate images of microcolonies grown from different types of pathogens, they encountered a surprising and unexpected result. Initially biased by the conventional belief that a high-magnification and high-numerical (NA) aperture objective would provide optimal images, the inventors first attempted to perform microscopic bright-field and dark-field imaging with a dark-field objective having a magnification of 20× and numerical aperture of 0.4. The resulting images are shown in the right-most panel of FIGS. 1A, 1C, and 1E.

While microcolonies were readily discernable in the bright-field images, albeit without significant morphological structure, the dark-field images obtained using the 20× objective (NA of 0.4) were dark within the regions corresponding to the microcolonies. In other words, an objective that provided clear microcolony images for bright-field imaging failed to provide clear microcolony dark-field images.

The present inventors, having failed to obtain clear dark-field microcolony images with a high magnification and high numerical aperture dark-field objective, turned to a lower, 5× magnification, with lower numerical aperture of 0.12. The resulting images are shown in the left-most panel of FIGS. 1A, 1C, and 1E.

Again, while the microcolonies were readily discernable in the bright-field images, again without significant morphological structure, the dark-field images obtained using the 5× objective appeared to be washed out and devoid of significant morphological structure. In other words, both of the objectives that provided clear microcolony images for bright-field imaging failed to provide clear microcolony dark-field images.

Figure 1A:
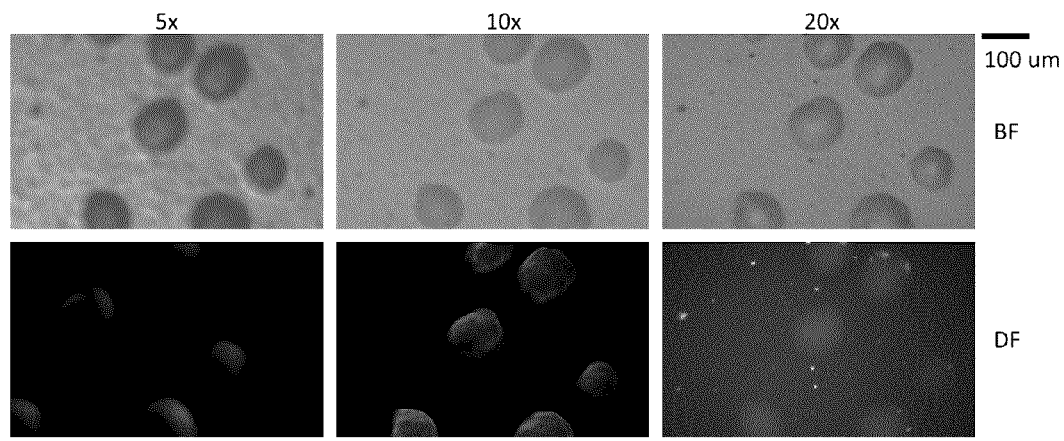
FIG. 1A shows bright-field (BF, top) and dark-field (DF, bottom) images of *Enterobacter Cloacae* Complex ECC ATTC 13047 microcolonies formed on a solid-phase growth medium, grown from a treated whole blood sample, and imaged by an upright reflected-illumination bright-field (BF) & dark-field (DF) microscope with 5×, 10× and 20× objectives after 4.5 hours of incubation at 37° C. Imaging data was resized with respect to 20×-10× was resized two times and 5× was resized four times.
Figure 1B:
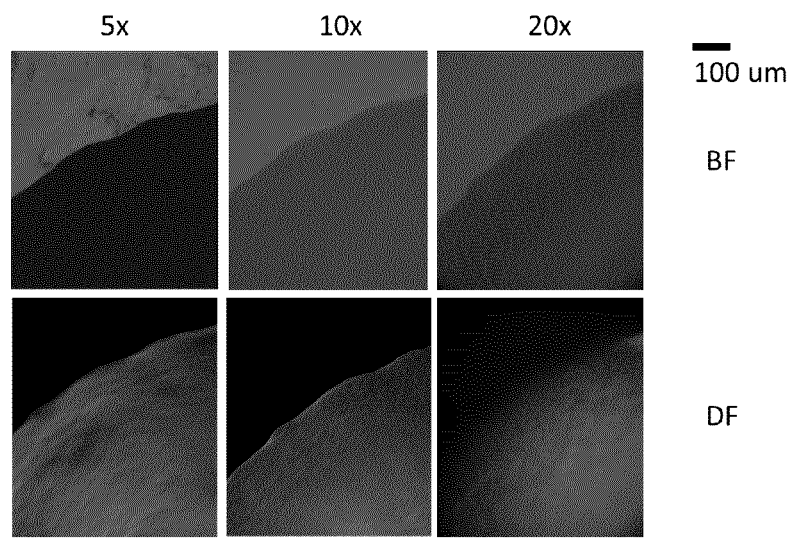
FIG. 1B shows bright-field (top) and dark-field (bottom) field images of *Enterobacter Cloacae* Complex ECC ATTC 13047 colonies formed on a solid-phase growth medium, after dispensing clean sample, and imaged by an upright reflected-illumination bright-field (BF) & dark-field (DF) microscope with 5×, 10× and 20× objectives after 24 hours of incubation at 37° C. Imaging data was resized with respect to 20×-10× was resized two times and 5× was resized four times.
Figure 1C:
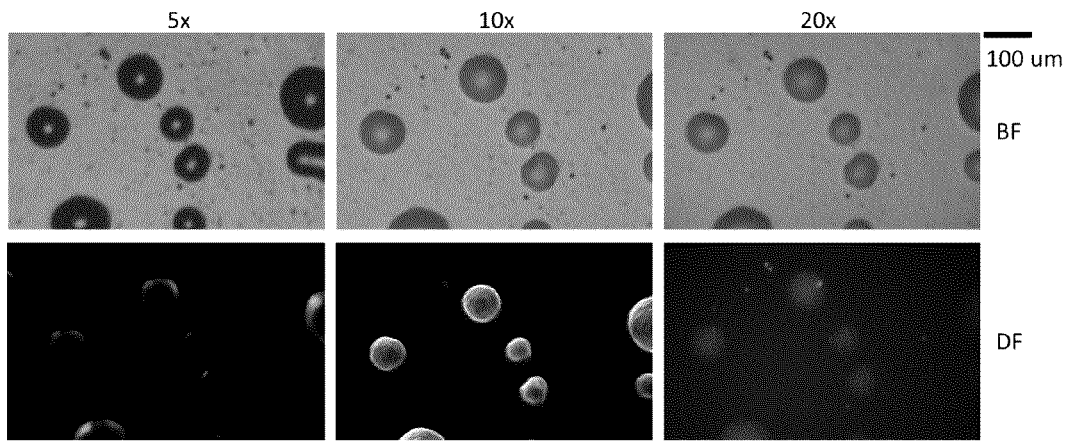
FIG. 1C shows bright-field (top) and dark-field (bottom) field images of *Enterococcus Faecalis* EF ATTC 51299 microcolonies formed on a solid-phase growth medium, grown from a treated whole blood sample, and imaged by an upright reflected-illumination bright-field (BF) & dark-field (DF) microscope with 5×, 10× and 20× objectives after 4.5 hours of incubation at 37° C. Imaging data was resized with respect to 20×-10× was resized two times and 5× was resized four times.
Figure 1D:
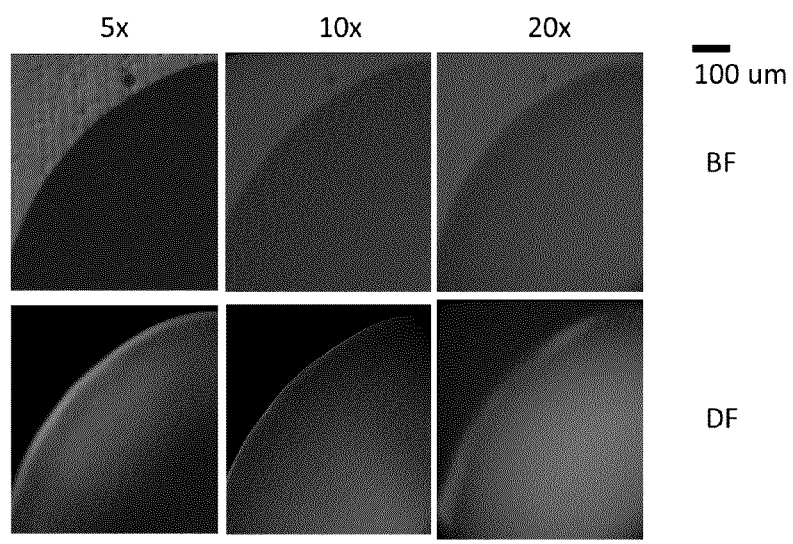
FIG. 1D shows bright-field (top) and dark-field (bottom) field images of *Enterococcus Faecalis* EF ATTC 51299 colonies formed on a solid-phase growth medium, after dispensing clean sample, and imaged by an upright reflected-illumination bright-field (BF) & dark-field (DF) microscope with 5×, 10× and 20× objectives after 24 hours of incubation at 37° C. Imaging data was resized with respect to 20×-10× was resized two times and 5× was resized four times.
Figure 1E:
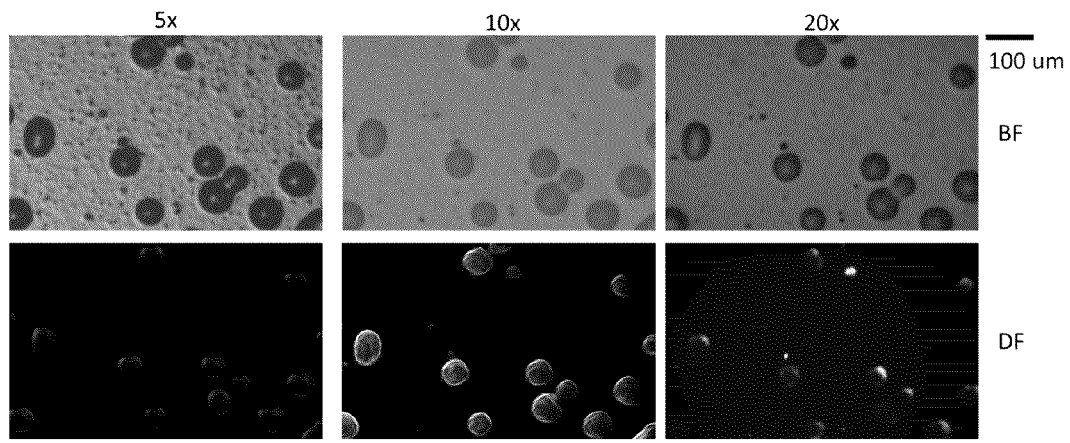
FIG. 1E shows bright-field (top) and dark-field (bottom) field images of *Staphylococcus Haemolyticus* SH ATTC 29970 microcolonies formed on a solid-phase growth medium, grown from a treated whole blood sample, and imaged by an upright reflected-illumination bright-field (BF) & dark-field (DF) microscope with 5×, 10× and 20× objectives after 4.5 hours of incubation at 37° C. Imaging data was resized with respect to 20×-10× was resized two times and 5× was resized four times.

Surprisingly, however, when the inventors employed an objective with an intermediate magnification of 10×, and an intermediate numerical aperture of 0.25, the dark-field microcolony images exhibited both a higher intensity and rich morphological features, often characterized by a complex, multi-ring pattern, as shown in the central panel of FIGS. 1A, 1C, and 1E. The present inventors thus realized that by selecting a dark-field objective having an appropriate intermediate numerical aperture, microcolony images with detailed morphological features could be obtained.

Without intending to be limited by theory, the present inventors believe that the observed dependence of the intensity and morphological complexity of the dark-field microcolony images on numerical aperture (or equivalently, acceptance angle of the dark-field objective), is due to the angular dependence of the higher-order light that is scattered from the microcolonies.

The scattering of light from a microcolony is believed to occur due to various mechanisms. A bacterial microcolony grown on a solid-phase growth media is a complex structure consisting of microbial cells, with or without single or multiple flagella or pili surrounded by the extracellular matrix and/or cellulose which might contain protein fibers that might form a scaffold, curli fibers, exopolysaccharides, extracellular proteins and appendages (such as cell-wall-anchored proteins). Within the microcolony, cells may be undergoing different stages of development. For instance, in the case of an *Escherichia coli* microcolony, which is schematically shown in FIG. 2, the main components are: (i) about 2 µm long and about 0.5 µm in diameter *Escherichia coli* cells, (ii) approximately κ-12 nm wide curli fibers, and (iii) approximately 20 nm wide and 5-10 µm long flagella and its filaments. When starting with a single bacteria/CFU (h=0.5-2 µm), a growing *Escherichia coli* (micro)colony can reach up 100 µm in height. Microcolonies of other bacterial species may have higher or lower level of elevation, as well as different type of elevation profiles (e.g., raised, flat, convex, or umbonate). While microbial cells are relatively large (e.g. *Staphylococcus* is 0.6-1×0.6-1 µm, *Streptococcus* 0.5-1.25×0.5-1.25 µm, *Enterococcus* 0.6-2×0.6-2.5 µm, *Escherichia* 0.5-1×2-3 µm), other intra- and extra-cellular components of the microcolony and the solid-phase growth media are significantly smaller (e.g. in the nm range). In addition, the solid phase growth media is a complex porous network. For instance, at 35° C., when the concentration of agar in solid-phase growth media is varied from 0.5% w/v to 3% w/v, the pore size varies from 1200 nm to less than 100 nm. This rate of this variation is for agar concentrations exceeding 1% w/v. For example, for agar concentrations within the range of 1-3% w/v, the pore size monotonically decreases from approximately 250 nm to approximately 70 nm.

In view of the complex presence of microbial cells, extracellular matrix, blood debris and solid-phase growth media in the case of dark-field microcolony imaging, the present inventors understood these various scattering components as each contributing to the overall dark-field microcolony image, with each scattering source having a different angular bandwidth.

Figure 3:
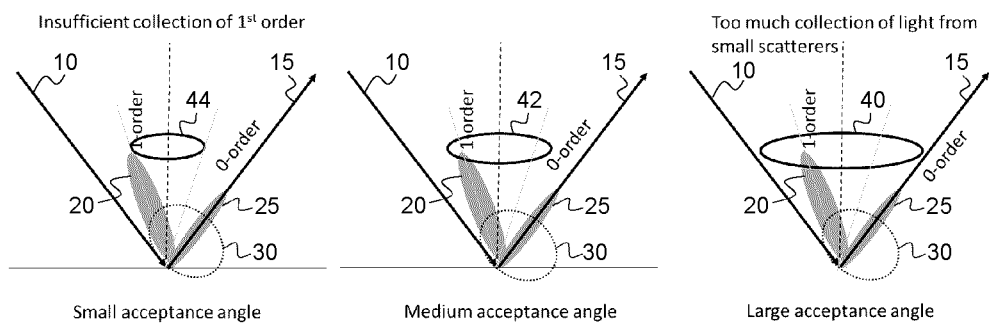
FIG. 3 schematically illustrates the contribution of background signal coming from small scatterers (indicated by dotted patterns) to the DF image of a large particle whose scattering pattern is schematically represented by filed lobes. The 0-order outgoing field is eliminated by the objective and the $1^{st}$ order field is collected. The left image shows the insufficient $1^{st}$ order field collection with small acceptance angle, the middle image shows the $1^{st}$ order field collection with medium acceptance angle and the right image shows too much collection of light from small scatterers with the large acceptance angle.

This concept is schematically illustrated in FIG. 3, which shows the indicted and scattered light in dark-filed imaging. The direction of the incident light is shown at 10, with the primary 0-order direction being shown at 15. Here the backscattered and forward scattered light for the case of large and small particles is presented respectively by filled (20 and 25) and dashed lobes 30, respectively, where "large" and "small" refer to in comparison with the illumination wavelength A and used the normalized scatterer size $x=2*\pi*r/\lambda$, where r is the radius of a spherical scattering particle. When x is small (x<<1), as shown by the dashed lobe, the scattering is predominantly isotropic, with zero order and higher-order scattering being substantially indistinguishable, as shown by the dashed lobe 30. Thus, for the inherently porous solid-phase growth medium, having a high density of small scatterers (pores), a significant background signal of scattered light is collected by an objective lens having a wide acceptance angle.

As shown in the figure, scattering from larger particles (x>>1), shown by the solid lobes 20 and 25, is more directionally confined and zero-order scattering 20 is separated from the higher order scattering (e.g. first-order scattering 25). A desired optical system for dark-field imaging is expected to reduce the collection of light from zero-order scattering. In the case of microbial colonies residing on a solid-phase growth medium, in which large target particles (e.g., cells) are surrounded by many small scatterers, such as pores in the solid-phase growth medium or features of the extra-cellular matrix, scattering from the small scatterers appears as a background in the dark-field image and obscures the finer features on the morphology of the microcolony. Due to the isotropic characteristic of this scattering, the background increases with acceptance angle.

The rightmost figure of the panel in FIG. 3 schematically illustrates the case of a high numerical aperture objective, such as the 0.4 NA 20× objective. In such a case, the first order light that is scattered by the pathogens of the microcolony (represented by the solid ellipse) is collected by the objective, as shown at 40, but is overwhelmed by the high background intensity generated by other scatterers, such as extracellular matrix and growth media, that are expected to generate a predominantly isotropic angular scattering dependence. This effect is evidenced by the high background signal observed in each of the dark-field images obtained using the 0.4 NA objective.

The leftmost figure in FIG. 3 illustrates the case of a low NA objective, in which angular bandwidth of the objective, shown at 44, is too small to collect a significant amount of the first-order (and higher order) light that is scattered by the microbial cells of the microcolony. Only a weak signal is collected that arises from the predominantly isotropic background scattering.

The central figure in FIG. 3, however, demonstrates that if a suitable dark-field objective with an intermediate numerical aperture is employed, a significant amount of the scattered intensity of the microcolony can be collected, since the first order component of the scattered light falls within the acceptance angle range of the dark-field objective, as shown at 42. Moreover, since less of the predominantly isotropic background scattering single is collected, relative to the first order scattering signal from the microcolony pathogens, a higher signal-to-noise ratio is achieved, and the complex, multi-ring morphology of the microcolony is captured.

Figure 1F:
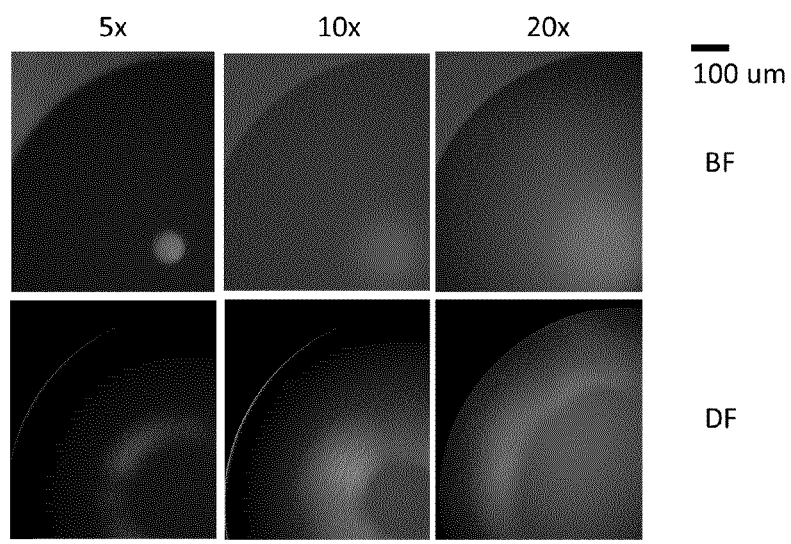
FIG. 1F shows bright-field (top) and dark-field (bottom) field images of *Staphylococcus Haemolyticus* SH ATTC 29970 colonies formed on a solid-phase growth medium, after dispensing clean sample, and imaged by an upright reflected-illumination bright-field (BF) & dark-field (DF) microscope with 5×, 10× and 20× objectives after 24 hours of incubation at 37° C. Imaging data was resized with respect to 20×-10× was resized two times and 5× was resized four times.

The present inventors conducted further experiments to determine whether or not the numerical aperture sensitivity to detection of microcolony morphological morphology in dark-field imaging was particular to the microcolony growth phase, or was a characteristic of both growing microcolonies and mature colonies. *Enterobacter cloacae* complex ECC ATCC 13047, *Enterococcus faecalis* EF ATCC 51299 and *Staphylococcus haemolyticus* SH ATCC 29970 colonies were formed on the solid-phase growth media containing 1.35% w/v of agar (prepared according to the method of Example 2), after dispensing clean sample, and imaged by an upright reflected-illumination bright-field (BF) & dark-field (DF) microscope with 5×, 10× and 20× objectives after 24 hours of incubation at 37° C. FIGS. 1B, 1D and 1F show bright-field and dark-field images collected from these mature colonies using objectives having numerical apertures of 0.12 (5× magnification), 0.25 (10× magnification) and 0.4 (20× magnification). Unlike the microcolony images shown in FIGS. 1A, 1C and 1E, the intensity of the dark-field images did not vary significantly between the images collected with different numerical apertures. Moreover, none of the dark-field images of the mature colonies exhibited the rich morphological structure observed in the dark-field microcolony images obtained with the intermediate numerical aperture.

This observation is suggestive that the complex morphology observed for intermediate numerical apertures is particular to the microcolony phase, i.e., colonies having a diameter of less than 200 μm in which the colony is in a high state of growth and dynamic morphology variation.

Accordingly, in some example embodiments of the present disclosure, microcolony images with complex morphology are collected during the microcolony growth phase. that occurs while the microcolony evolves into a mature colony, for example, when the microcolony has a spatial extent (diameter) of less than 200 μm.

In some example implementations, dark-field images of such microcolonies are obtained using an objective characterized by an intermediate numerical aperture residing between 0.16 and 0.28, or for example, between 0.2 and 0.3, or for example between 0.18 and 0.32, or for example between 0.15 and 0.35. Typical magnification values for these ranges, which may depend on the optical design of the objective, are between approximately 7× and 15×, or, for example, between 6× and 18×.

Effect of Agar Concentration on Dark-Field Microcolony Morphological Complexity

The present inventors found, through experimentation, that the composition of the solid-phase growth medium, such as, but not limited to, the concentration of agar in the solid-phase growth medium, can have a significant effect on microcolony growth and morphology. In order to quantity this aspect of microcolony growth, an experimental study was conducted to investigate the effect of agar concentration in the solid-phase growth medium on the complexity of the morphology of dark-field images. In a first aspect of the study, solid-phase growth media was prepared according to Example 2 and the effect of its composition on the cell growth/proliferation rate was investigated.

For the experimental study, 0.2 μl from a stock solution of *Klebsiella Pneumoniae* cells, which had been prepared according to the method of Example 6, was seeded onto solid-phase growth media containing 1.5% w/v, 1.75% w/v, and 2% w/v of agar, and then cultured in an incubator for 3 and 4 hours, respectively. After incubation, the newformed microcolonies were washed out, seeded into the new solid-phase growth media containing 1.35% w/v of agar prepared according to the method of Example 2, and counted after overnight incubation. The results are presented in the summary box plot of FIG. 4, which present the median value and quartile of growth rate in the time period between 3 and 4 hours after incubation. Here, "growth rate" is intended to mean the number of times the cell content of the microcolony has doubled during the specified time range. As it is observed, some cellular proliferation of the solid-phase growth media containing 1.75% w/v and 2% w/v of agar is approximately 3 times lower when compared to the cell proliferation on the solid-phase growth media containing 1.5% w/v of agar.

In another experiment, dark-field images were obtained of microcolonies of American Type Culture Collection (ATCC) strains and hospital clinical isolates (MSH) of Gram-positive (*Staphylococcus Aureus* SA ATTC 25923, *Enterococcus Faecalis EF ATTC* 51299, *Staphylococcus Epidermidis* SE ATTC 12228) and Gram-negative (*Escherichia coli* EC ATTC 35218, *Klebsiella Pneumoniae* KP CRE MSH 1705, *Proteus Mirabilis* PM ATTC 12453) bacteria, which had been prepared according to the method of Example 4. For every strain, 1 μL of the sample was dispensed on a solid-phase growth medium, which had been prepared according to the method of Example 2, with an agar concentration of 2%. The resulting plates were placed into the incubator and imaged at various regular time intervals.

The images were acquired with dark-field reflected microscope using 10× objective and illumination light from an LED light sources (royal blue 445 nm), The numerical aperture of the objective was 0.25 and was found to be suitable for generating dark-field images with high microcolony morphology, as described above. Images were acquired after 2.5, 3.5, and 4.5 hours of incubation. In each case, the images presented pertain to the most typical morphological shapes observed at the given acquisition time.

As shown in FIG. 5A, each of the 6 species of bacterial cells have characteristic morphology. Three of these species (including PM, SA, and SE) were substantially monodisperse in morphological terms, meaning that different microcolonies across the plate had similar shapes. In contrast, the other three species (including EC, EF, and KP) were polydisperse, meaning that there was obvious variation in the morphology of different microcolonies that had formed across the plate. For these polydisperse bacterial cells, characteristic images have been provided and the most likely morphology has been indicated with an arrow.

FIGS. 5B-5D are images of microcolonies generated by seeding several different sepsis-causing pathogens onto solid-phase growth media having concentrations of agar ranging from 1%-2%, with respective agar concentrations of 1% w/v, 1.35% w/v, 1.5% w/v, 1.75% w/v, 2% w/v, and one commercial blood agar plate (A10, Hardy Diagnostics). The incubation times of the microcolonies prior to imaging were 2.5 hours (FIG. 5B), 3.5 hours (FIG. 5C), and 4.5 hours (FIG. 5D). The figures illustrate how microcolonies undergo noticeable, and in some cases dramatic, change in their morphology over time. For instance, considering the case of PM microcolony on 1% agar, the microcolony was in the form of a hollow ring at t=2.5 hours and by 4.5 hours it had developed into 4 concentric rings.

In addition, the images demonstrate that the agar concentration in the solid-phase growth media can impact the formation of the characteristic ring patterns. When compared to the commercial blood agar plates (A10), the solid-phase growth media that had been prepared according to the method of Example 2 was found to produce microcolonies with more prominent patterns when both were inoculated and incubated under identical conditions. It is believed that the low performance of the commercial plate compared to its in-house counterpart (1.5% w/v) is due to its storage condition which allows condensation on the solid-phase surface, thus reducing the solid character of the surface.

Figure 4:
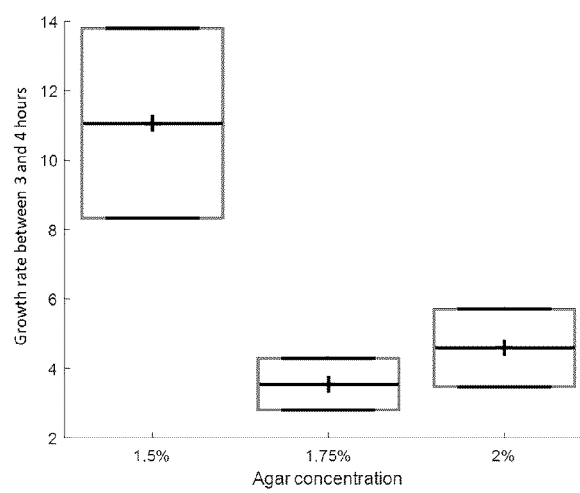
FIG. 4 plots the effect of agar concentration in the solid-phase growth medium on the proliferation rate of *Klebsiella Pneumoniae* between 3 and 4 hours of incubation at 37° C. The x-axis presents percentage of the agar in the solid-phase growth media: 1.5% w/v, 1.75% w/v and 2% w/v.

The results from FIGS. 5B-5D also indicated that agar concentrations in the range of 1.35-2% w/v appear to enhance certain morphological features relative to the morphological features observed at an agar concentration of 1.%. Thus, higher agar concentration (1.5-2.0% w/v) appears to be more desirable for classification purpose for the example solid-phase growth medium composition presently studied. However, as shown in FIG. 4 and described above, for at least some microbial cell species, and for the example solid-phase growth medium composition presently studied higher agar concentrations (e.g. concentrations above 1.5% w/v in the example case of KP) may result in lower microbial growth rates for the example solid-phase growth medium composition presently studied.

Accordingly, the skilled artisan may determine a suitable and/or optimal concentration of agar, for given type of solid-phase growth medium, and for a given set of microbial cell types (e.g. a selected set of pathogen species or other taxonomic classes), by performing experimental studies in which microcolonies are grown on solid-phase growth media having different agar concentrations, and growth rate and/or microcolony morphology is assessed, in order to determine an agar concentration, or range of agar concentrations, that provides a desired microcolony growth rate and/or microcolony morphology.

In order to investigate the possible dependence of the microcolony morphology observed on dark-field images on illumination spectrum, dark-field images of microcolonies of Gram-positive bacteria *Enterococcus Faecalis* (EF ATTC 51299) and Gram-negative bacteria *Escherichia coli* (EC ATTC 35218) were obtained and compared. These microcolonies had been prepared according to the method of Example 4, grown on the selected solid-phase growth media with the respective agar concentrations of 1.5%, 1.75%, and 2% w/v, which had been prepared according to the method of Example 2. The images which are presented in FIG. 5E were taken by a dark-field microscope with 10× objective and 2 LED light sources (royal blue B 445 nm and red R 623 nm). As it is shown in FIG. 5E, for all acquisition times, namely after 3, 4 and 5 hours of incubation, average scattering intensity is higher for the example Gram-positive bacteria (EF) with respect to the example Gram-negative bacteria (EC) for both illumination channels under identical settings in terms of exposure time and sensor gain.

Accordingly, in some example embodiments of the present disclosure, microcolony images with complex morphology are collected during the microcolony growth phase, between the time of detection of the microcolony and the evolution of the microcolony into a mature colony, for example, when the microcolony has a spatial extent (diameter) of less than 200 µm, where the microcolonies are grown on an agar-based solid-phase growth media that includes an agar concentration ranging between 1-2.5% w/v, 1.25-2.3% w/v, 1.5-2% w/v, 1.5-2.25% w/v, 1.5-2.5% w/v, 1.25-2.5% w/v, 1.75-2.5% w/v, and 2-2.5% w/v. In some preferred embodiments, microcolonies grown on any one of the preceding ranges of agar concentrations are imaged, during the microcolony growth phase, using a dark-field objective having a numerical aperture (or collection angle) within the preceding example ranges.

Effect of Humidity on Dark-Field Microcolony Morphological Complexity

The present inventors have found that different pathogen species can exhibit microcolony morphology complexity (i.e. a high degree of spatial complexity in dark field images) under different environmental conditions. For example, the temperature (T) and relative humidity (RH) suitable for generating the most complex dark-filed microcolony morphology images may be different than the optimal temperature and humidity for another pathogen species.

The present inventors undertook a detailed experimental study of the effect of humidity (during incubation) on the complexity of the microcolony morphology of dark-field images. In a first portion of the study, commercial solid-phase growth media with 1.5% agar concentration (A10 Blood Agar Plate, Hardy Diagnostics) was used.

FIG. 6A shows dark-field images of *Staphylococcus epidermidis* SE ATTC 12228, *Enterococcus faecalis* EF ATTC 35667, *Escherichia coli* EC ATTC 35218, *Pseudomonas aeruginosa* PA ATTC 35554, *Staphylococcus aureus* SA ATTC 25923, *Klebsiella pneumoniae* KP ATTC 700603 microcolonies, prepared according to the method of Example 4, imaged by an upright reflected-illumination dark-field microscope with 7.5× objective after 3 hours of incubation at 35° C. and 3 selected relative humidity settings (19%, 35-65% and 99%). For every organism 1 µL of the sample was dispensed on a solid-phase growth medium. The results indicate that in the present example case, the average radius of microcolonies incubated in a low humidity environment is approximately 2-3 times lower than the average radius of microcolonies incubated in 99% RH, suggesting a decrease in the growth rate and/or increase of the lag phase. Moreover, the images suggest that decreasing the relative humidity from saturated conditions appears to result in more distinct ring patterns. While similar ring patterns are formed in a higher humidity as well, they appeared blurred. In contrast, it appears that spatial patterns with higher contrast are formed for lower humidity than fully saturated conditions.

As it was previously discussed, for the solid-phase growth media employed in the present examples, agar concentrations of approximately 1.35-2% w/v appear to promote the formation of characteristic ring patterns in the acquired dark-field images. FIG. 6B shows dark-field images of *Staphylococcus epidermidis* SE ATTC 12228, *Enterococcus faecalis* EF ATTC 35667, *Escherichia coli* EC ATTC 35218, *Pseudomonas aeruginosa* PA ATTC 35554, *Staphylococcus aureus* SA ATTC 25923, *Klebsiella pneumoniae* KP ATTC 700603 microcolonies formed on a solid-phase growth medium with 1.75% agar concentration and imaged by an upright reflected-illumination dark-field microscope with 7.5× objective after 3.5 hours of incubation at 35° C. for three selected relative humidity settings (15%, 65-93% and 99%). The results illustrate that, in the case of the present example solid-phase growth media and the present example pathogens, microcolony morphology complexity appears to be higher for relative humidity values in excess of 10%.

In conclusion, solid-phase growth media, which had been prepared according to the method of Example 2, with an agar concentration (1.5-2.0% w/v) combined with relative humidity within the range 30-70% appears to generate microcolonies with distinct morphological complexity.

Temporal Dependence of Observed Pathogen-Specific Dark-Field Morphology During Microcolony Phase The present inventors, having discovered the aforementioned numerical aperture sensitivity of dark-field microcolony image intensity and complexity of morphology, set out to employ the discovered appropriate numerical aperture range to obtain images of the time-dependence of morphology changes during the microcolony growth phase for different pathogen species.

An example of this time-dependent morphology can be seen in FIG. 8C, which shows F-stacked joined images of *Escherichia coli* (EC) and *Staphylococcus aureus* (SA) microcolonies as a function of time over a time duration spanning four hours. This time-lapse series of F-stacked microcolony images illustrates the temporal evolution of a typical Gram-negative (EC) microcolony and a typical Gram-positive (SA) microcolony.

As it is seen from the figure, EC, which is a typical Gram-negative microcolony, starts with a low overall scattering (as evidenced by the low dark-field signal), while as the incubation time increases, the microcolony becomes more compact, particularly in central area, and scattering increases. In contrast, SA, a typical Gram-positive microcolony, has the tendency to exhibit a more compact profile during its microcolony evolution from seeding, hence having higher scattering power earlier during microcolony evolution. Moreover, while SA, a typical Gram-positive microcolony, is small and round, EC, a typical Gram-negative microcolony, is observed to generate a microcolony with a comparably larger size and irregularly shaped perimeter. These significant differences in time-dependent microcolony size, shape and morphology demonstrate the potential for employing one or more of these time-dependent features as a means for the rapid detection and classification of pathogens.

The temporal development of EC and SA microcolonies is observed in the figure to include the following phases: (i) an early development phase when the microcolony is initially detectable and does not yet exhibit clear characteristic features, (ii) an intermediate development phase during which the microcolony grows in size and the characteristic morphological features are developed (this phase may include two or more subphases), and (iii) a mature phase characterized by transition to a substantially stationary morphology (likely due to spatial compaction).

FIG. 7A illustrates such a growth model, in which the microcolony stage is characterized by significant colony growth and the development and time-varying expression of different morphological features, and in which the colony stage involves the continued growth of a mature colony without significant changes in colony morphology.

Without being bond to the theory, the spatiotemporal dynamics during the establishment of microcolonies appears to be correlated with a degree of spherical symmetry, motility and composition of the extracellular matrix. On the later stages of the early development, when the critical cellular mass is reached and cells are surrounded by the extracellular matrix, characteristic patterning is taking place due to the trade-off between 'verticalization' and horizontal spread. Here the verticalization means formation of new layers on top on the existing layer. The observed ring structure of the microcolonies is partially due to the occurrence of this phenomenon. Horizontal spread is the inhabitation of already occupied areas outside of the microcolony boundaries.

During the later stages of microcolony growth, a transition from monolayer to multilayer growth may take place with a (semi)multi-layer in the center and monolayer in the outer ring. In the case of dark field imaging, this may partially explain the observed increased scattering from the microcolonys center.

However, not all observed ring patterns appear to be directly related to the multilayer nature of the microcolony. During monolayer expansion, due to volumetric pressure from cell growth, as schematically shown in FIG. 7B, bacteria can detach from neighboring cells causing wrinkles in the microcolony which might appear as more or less well-defined ring structure under dark field microscope. This phenomenon appears to happen for the microcolonies of rod- and oval-shaped bacteria. The spherical asymmetry induces mechanical tension, and drives daughter cell (re) arrangement as neighboring cells tend to align.

Bacterial motility may also play a role in the formatting of the characteristic ring patterns. Based on the bacterial motility, different cell density of different bacterial subtypes (phenotypes) might be present at different distances from the microcolony center. In case of *Escherichia coli*, flagellum might play a major role in the development of the colony ring structure. Similar to the architecture of the macrocolony (mature colony), schematic microcolony in FIG. 7C contains a series of concentric rings. For example, a microcolony could be divided into 3 zones: well defined outer and inner zones, and partially visible middle zone. Under dark field microscopy, zone I will appear brighter than zone 2, most likely not because of having higher cellular density but because of lacking extracellular matrix and sudden drop in density. Without being bound to theory, it appears that dividing, flagellated cells are found within the narrow outer edge in zone I. Middle and inner zones (zone II and zone III) might be different in the proportion of mature cells in a mesh of flagella filaments and stationary phase cells.

In contrast, the microcolonies of non-motile bacterial species might not present zonal variation. For example, *Staphylococcus aureus* has a colonization mechanism relying upon polysaccharide intercellular adhesion production. Strong cell-to-cell interaction occurs and facilitates verticalization. This results in more packed microcolonies. Similar behavior was present for other non-motile *Staphylococcus* species tested during the present study (*S. aureus, S. epidermidis, S haemolyticus.*

Motile species have a tendency of forming flower-like/mushroom/dendritic patterns during early stages of development characterized by a decreased circularity (c). A shape factor (S) was employed, defined as the logo of circularity (c), to quantify the colony shape, where $c=(P^2)/(4*\pi*A)$ is dimensionless circularity, P is the microcolony perimeter in pixels, A is the area of the microcolony in pixels$^2$. $S=\log_{10}$ (c), where S is dimensionless shape factor. This shape factor has a high value when the colony is round (e.g. Gram-positive) and a low value when the colony is branched (e.g. Gram-negative).

Without being bound to theory, many of the factors causing variation of the microcolony patterning on different solid-phase growth media are associated with motility and motility dependence on the growth environment. For example, motility is strongly dependent on agar concentration in the solid-phase growth media, nutrients level and growth temperature. The most important types of motility in the context of ring formation appear to be swimming and swarming. For example, *Escherichia* has a tendency for swimming motion via peritrichous flagella. Similar behavior is also observed in *Proteus* and *Pseudomonas*. On the same time, *Proteus* is more prone to swarming (swimming in groups) in temporal cycles.

The ring characteristics for *Proteus* microcolonies appear to be at least partially related to the differences in swimming vs. swarming behavior (swarming cycles of *Proteus*). Moreover, the rate of surface colonization via swarming is equal or exceeds the rate of swimming, leading to the increased surface area of swarming species vs. swimming spices. As swimming predominates at low agar concentration (0.2-0.35% w/v) and swarming predominates on higher agar concentration (1-2% w/v), swarming behavior might be the dominating parameter in the ring structure of the microcolony morphology. Solid-phase growth medium with agar concentrations above 2.5% w/v, typically do not support swarming motility. Other factors governing the level and type of motility are temperature and humidity. Swimming, swarming and sliding motilities are inhibited at elevated or decreased.

The colony appears to need to reach a minimum threshold CFU, beyond which the cells begin moving collectively, so called lag period prior to swarming migration. This number is estimated to be around $10^3$.

Other important types of motility in the context of ring formation are twitching and gliding. Twitching/gliding is a unidirectional motion via pili. *Acinetobacter* and *Pseudomonas* have a tendency for twitching/gliding. Like *Proteus, P. aeruginosa* has a tendency for social gliding (gliding in groups) which we believe might be associated with concentric rings too. Twitching can work under drier conditions such as 1.5% w/v agar and is not observed in many organisms on nutrient-poor medium. However, for bacteria that glide without pili nutrient-poor conditions favor motility.

*Acinetobacter* and *Escherichia* have a tendency for sliding without motion organelles. There is no general rule for sliding/gliding moisture dependency: some strains show motility on medium with less agar (1% w/v) and some others on medium with more agar (2% w/v).

*Pseudomonas aeruginosa* exhibits three types of motilities: (i) swimming, (ii) swarming, and (iii) twitching with could be interchanged based on the environmental conditions. Thus, it is expected that it can be more easily differentiated from other bacterial species employing the features on its microcolony.

The present inventors discovered that dark-field imaging of a microcolony during the initial development phases of the microcolony, in particular employing the aforementioned ranges of numerical aperture of the dark-field objective that are suitable for generating microcolony images with high morphological complexity, can yield microcolony images with complex ring-shaped features that vary with time and which can serve as highly differentiated data for microcolony classification at the Gram-stain level, and potentially at the species specific level too. Example methods of classification of microcolonies by processing of such images are described below.

The preceding examples have demonstrated, through the use of dark-field imaging of microcolonies, using a suitable intermediate numerical aperture, and a suitable solid-phase growth medium and environment, that microcolony morphology can vary dynamically during the microcolony growth phase, in contrast to larger, mature colonies, as explained, for example via FIG. 7A. The present inventors expected that when to microcolonies of the same type (i.e., same species) grew from a common seeding event, they would undergo growth an evolution through the phases of microcolony development and microcolony morphology in a substantially sequential manner. Surprisingly, further experiments performed by the present inventors suggested that this is not the case for some microbial species, and that some microcolonies growing from a common seeding event can pass through different phases of development, and thereby exhibit different morphologies in dark-field images, at different times.

This difference in phase evolution was observed in experiments that were performed to investigate the effect of solid-phase composition on the microcolony patterning during early stages of microcolony development. Clean samples were employed that had been prepared according to the method of Example 4, containing the seeded American Type Culture Collection (ATCC) strains and hospital clinical isolates (MSH) of Gram-positive (*Staphylococcus Aureus* SA ATTC 25923, *Enterococcus Faecalis* EF ATTC 51299, *Staphylococcus Epidermidis* SE ATTC 12228) and Gram-negative (*Escherichia coli* EC ATTC 35218, *Klebsiella Pneumoniae* KP CRE MSH 1705, *Proteus Mirabilis* PM ATTC 12453) bacteria, which had been prepared according to the method of Example 5. 1 μL of the sample was dispensed on a solid-phase growth medium. The plate was placed into the incubator and regularly imaged by taking dark-field and bright-field images across the solid-phase growth medium surface by metallurgical/reflected microscope with epi-illumination by a blue LED light source.

For this study, in the imaging region of interest (ROI) there are typically approximately 25-30 microcolonies. The FIG. 8A shows typical shapes and dark-field patterns of microcolonies of the selected species as observed respectively at 3 and 4 hours of incubation after seeding into the solid-phase growth medium, which had been prepared according to the method of Example 2, with 2% w/v agar concentration.

As it is shown in FIG. 8A, for some species, such as EC, KP, and PM, morphological variation is relatively high for a common time since seeding. For example, four EC microcolonies were observed in different morphological growth phases simultaneously present within one field of imaging (FOI defined as the lateral spatial region imaged by the objective) during the same acquisition: (i) this microcolony morphology is the most likely case for 2 hours of incubation and it likely has a monolayer of cells with the boundary between zones II and I has not yet well developed; (ii) this microcolony is the most likely case for 3 hours of incubation and it likely is in monolayer-to-multilayer transition with development of the boundary between zones II and I; (iii) this microcolony is the most likely case for 3.5 hours of incubation and it is likely at the end of monolayer-to-multilayer transition with developed boundary between zones II and I; (iv) this microcolony is the most likely case for 5 hours of incubation and it is likely a multilayer of cells with multiple rings. In this case the most typical shape for the given acquisition time is highlighted with white arrow. For two of the species presented in the FIG. 8A, i.e., SA and SE, the temporal variation in microcolony morphology is less pronounced and the main time-dependent parameter is size of the microcolony. In this case shape present during the earlier acquisition time is a scaled version of the shape present during the later acquisition time. Thus, in the case of this type of species, for the qualitative analysis the most typical shape was selected.

Some of the observed morphological variation could be explained by the fact that microbial cells seeded on the solid-phase growth medium might have been at different growth stages. Moreover, they may have endured stresses to different levels during cell separation from biological sample. Therefore, imaging at sufficiently short intervals is required for classification with high confidence level. Intervals of approximately $\Delta t=30$ minutes intervals are satisfactory in this respect, while shorter intervals, for example approximately 15-minute intervals, might be preferable. However, such short time intervals may decrease the system performance if perturbation to the growth dynamic from the proximity of the objective occurs.

In view of these observations, the present inventors believe that since a given microbial cell can be at different stages of growth or it could be subjected to a different level of stresses, the morphological shape of its colony may not be predictable solely by determining the time elapsed since seeding of the sample or incubation, at least for some microbial species.

The present inventors thus observed that in a statistically large population of microbial cells separated from biological samples such as blood and seeded on a solid-phase growth media, each viable cell will form its own microcolony passing through stages of specific spatial patterns, and at a given time, only a fraction of microcolonies in the population may have substantially similar shapes. However, if observation is performed over long periods, e.g., 2-3 hours, most or all of the microcolonies appear to pass through similar morphology phases. Thus, characteristic features extracted from the characteristic morphology phases could be used for the microcolony presumptive identification.

Example Method of Performing Detection, Monitoring and Classification of Microcolonies Using Dark-Field Imaging The present inventors realized that despite the observed lack of a deterministic time-dependent evolution of the dark-field morphological structure of microcolonies, the observed consistent stages of morphological changes during the microcolony growth phase could nonetheless be employed to facilitate microcolony classification. Accordingly, as described in further detail below, in some example embodiments, microcolony classification may involve the processing of a set of images obtained at different times during the growth of the microcolony, in order to perform classification based on multiple time-ordered phases of microcolony morphology in dark-field images.

Referring now to the flowchart of FIG. 9A, an example method is provided for performing microcolony classification based on a time series of dark-field microcolony images. At step 100, solid-phase growth media is selected that is suitable for supporting the growth of microcolonies that exhibit complex morphologies when dark-field images are obtained. For example, a solid-phase growth medium may be selected to have an agar concentration as per the ranges described previously and growth environment with appropriate relative humidity and temperature.

Non-limiting examples of solid-phase growth media include agar, gelatin, guar gum, Xanthan gum, having suitable growth nutrients. Since House et al. in 1965, solid and solidified growth media in microbiology is mainly agar based. An example of preparation of the agar-based solid-phase growth media with a composition appropriate for supporting microcolonies with enhanced characteristics is described in Example 2. While a wide range of solidifying agents could be used, solid-phase growth media should contain essential nutrients for bacterial growth and proliferation, and facilitate bacterial collective motion.

In some implementations of the method, the solid-phase growth medium is an agar-containing medium, which had been prepared according to the method of Example 2. The percentage of agar in the solid-phase growth medium may range between 1.2% and 3%, or may vary between the agar concentration ranges provided above, more preferably between 1.5% and 2%, or other example ranges described above.

The cell suspension that is seeded onto the solid-phase growth medium may be any liquid microbial cell suspension, in which the desired viable microbial pathogens are suspended in a liquid medium, and may be derived, for example, directly from the sample without growth. For example, the cell suspension could be prepared via separating microbial cells from sample matrix and resuspending them in an aqueous medium. Alternatively, the cell suspension may be obtained after performing an initial growth step, such as via conventional culture or subculture. Furthermore, the cell suspension may originate from a single sample or from multiple samples. Non-limiting examples of sample types include blood, urine, mucus/sputum, cerebral spinal fluid, homogenized tissue samples, and other sample types described above.

The non-limiting example workflow of FIG. 9A includes an optional separation step, shown at 105, in which the microbial cells are separated from sample matrix. This step may be performed when the microbial cells reside in a complex sample, such as blood. However, it will be understood that in other implementations, such as those involving urine samples or cerebral spinal fluid samples, the separation step may be omitted. As used herein, the phrase "separation process" refers to a process suitable for separating and optionally concentrating microbial cells. Non-limiting examples of separation processes include centrifugation, filtration, immunomagnetic separation and microfluidic separation. In some implementations of the method, the sample is a whole blood sample and the microbial cells are separated from the sample by mixing the whole blood sample and a blood lysis reagent according to the method of Example 2.

If included, the separation step may be performed according to a wide range of methods, which may depend on the nature of the sample. For example, in some example implementations, separation may be achieved by centrifugal force or filtering, and may optionally employ a lysis step for digesting mammalian cells which may be present in the sample and would otherwise impede the intended microbial cell separation by co-sedimenting with them or fouling the filter (such as a hemolysis step). This digestion may be performed in a selective manner, such that the microbial cells do not lose their viability and the fraction of debris, which are inevitably transferred along the separated cells to the growth chamber, do not interfere with cell growth on the solid-phase growth medium and the subsequent image analysis. Accordingly, for some samples, selective mammalian cell (e.g., blood cell) lysis with appropriate reagents is performed in step 105. The separated cells may be resuspended in a clean aqueous media, such as saline solution or growth media.

At step 110, the cell suspension is contacted with the solid-phase growth medium. This may be performed simply by adding sample onto the surface and allowing it to spread over the surface by gently agitating the chamber. Alternatively, centrifugal sample seeding can be done as described in International Patent Application No. PCT/CA2019/051895. In some implementation of the method, the surface contacting the microbial cell suspension might be partitioned into sections with varying composition and the microbial cell suspension might be contacting multiple surfaces. In some implementations, a liquid-absorbing solid-phase growth media (a solid-phase growth media that is not fully hydrated and has a capacity for further absorption) may be employed to facilitate the controlled absorption of microbial cells from a cell suspension onto a surface for colony growth.

In step 115, the solid-phase growth medium with the seeded microbial cells is incubated under the conditions promoting cellular growth and proliferation. Non-limiting example conditions include a temperature range of 35±2° C. and a relative humidity range of 30-70%. Alternatively, relative humidity may be selected to be within the range 40-60%. It is noted that a suitable environment should be provided that permits the microcolonies to remain viable while preventing substantial evaporation of liquid from the surface of the solid growth medium, as such evaporation can lead to shrinkage, which can in turn lead to time-dependent displacement of features (debris features and microcolonies) and cause, for example, loss of image registration. The active control of the temperature and humidity may be beneficial in preventing such problems.

In step 120, an imaging system is employed for the detection of microcolonies and for the collection of dark-field microcolony images. As described below, the imaging system may be autofocused on the surface of the solid-phase growth medium using debris particles residing on the surface of the solid-phase growth medium, or using extrinsic particles added to provide fiducial reference features of the surface of the solid-phase growth medium. The imaging system may be employed to acquire single microcolony images, or, for example, composite images (e.g. F-stacked composite images) for subsequent image processing and classification.

FIG. 9B illustrates an example workflow for performing the imaging step 120 of FIG. 9A. The time at which the solid-phase growth medium, on which the cell suspension is seeded, is placed into an environment supporting colony growth is taking as the reference for subsequent steps.

As shown at step 121 of FIG. 9B, a stabilization time $t_s$ may elapses prior to collecting the reference image of the solid-phase growth medium, thereby allowing shrinkages and settling of the sample debris to occur, at least in part, prior to image acquisition. This time period may range, for example, between 0.1 to 4 hours. In some example implementations, this delay period may be approximately 30 minutes.

At step 122, the surface of the solid-phase growth medium is optically scanned for acquiring the image of debris or other surface imperfections to be later used as a reference for removing background and/or object detection.

In some example implementations, a reference image to of the solid-phase growth medium (e.g., approximately 30 min-1 hour after seeding) may be initially acquired and floating images $t_n$ (modified during image registration, e.g. translating or rotating) of the solid-phase growth medium may be subsequently obtained, where the floating images are obtained after incubation for a given periods of time (approximately 30 min intervals or preferably less than 15 minutes).

Image subtraction may be performed after optional registration of the reference and floating images to remove surface artefacts such as blood debris from the floating image, thereby obtaining a subtracted image that permits the detection of a microcolony via an image processing detection method.

As explained below, in some example embodiments, extrinsic particles can be added either to the solid-phase growth medium or the sample for generating spatial features on the background. Such an implementation may be useful when the cell suspension does not include sufficient number of intrinsic particles to provide fiducial reference points across the solid-phase growth medium within the selected field of view during imaging. The scanning may be repeated one or more times for ensuring the establishment of background stabilization. In some example implementations, instead of the aforementioned passive delay method of avoiding shrinkage and settling, an active method may be employed. In this case, a series of initial images may be acquired and processed and a reference measure based on the spatial separation between two or more reference (fiducial) points (which provided naturally by sample debris or added to the sample) may be determined. The first image for microcolony analysis may be obtained after the reference measure satisfies pre-selected criteria, such as being less than a prescribe threshold value.

At least a subset of the surface artefacts used for the image registration and intensity normalization may be inhomogeneities in the surface of the solid-phase growth medium, and/or at least a subset of the surface artefacts may be extrinsic particles with varying reflectivity (40%-70% of the dynamic range). The sample processing may be configured such that a fraction of coverage of the solid-phase growth medium by particles and debris is less than 20%, 50% or 90%. Moreover, the sample processing may be configured such that on average, at least 1, at least two, or at least three extrinsic particles are present within each imaging FOI.

The extrinsic particles above could be used for the intensity calibration and shading correction as the acquired intensities might be influenced by a variety of sample- and instrument-related parameters. In one embodiment the intensity correction could be performed via flat-field correction method. In this case the corrected image C is obtained via operation $C=(R-D)/(F-D) \cdot m = (R-D) \cdot G$, where R is raw image that was originally acquired, F is flat-field image that was acquired at to with light source ON, D is dark-field image that was acquired at $t_0$ with light source OFF, m is image-averaged value, G is gain which is defined as the ratio between the current intensity of the particles to the their reference intensity. Reference intensity could be provided via a factory calibration or barcoded on the growth module. In order to avoid intensity saturation or strong background, the intensity of the extrinsic particles may be selected to be within 40-70% of the dynamic range of the average intensity across the field of view.

After acquiring the background image, the same optical module may be engaged for optically scanning for the emergence of microcolonies, as shown at step 123. The present inventors have found (as shown, for example, in FIG. 8C) that for some species of pathogenic bacterial cells, microcolonies can be detected after only 1 hour, as imaged by an upright reflected-illumination microscope with 10× objective. Moreover, since the number of microbial cells in the sample is generally not known, a priori for the fast-growing microbial cells, a longer time (e.g., approximately 2, 2.5 or 3 hours) may be required for the detection of the majority of microcolonies even in the case of the fast-growing bacteria. In some example implementations, the scanning for the presence of microcolonies may be started one hour after seeding at step 116.

At step 131, the images of the surface, taken at step 123, are compared with the background reference image and following the procedures that will be described below, the emergence of one or more microcolonies is detected. At step 132, the location(s) of this(these) microcolony(ies) will be determined by referencing to set points on the solid-phase growth medium or the optical system.

For example, algorithms such as those employed by the ImageJ/Fiji program, may be employed to facilitate microcolony detection. In one example method, after converting an image into a greyscale image, the greyscale image may be binarized by applying local adaptive image thresholding according to Phansalkar method, based on histogram analysis of intensity levels. Adaptive image segmentation may then be employed according to Phansalkar method, with dimension constrains that partition an image into segments for microcolony identification. Optional further analysis of the identified segments may then be employed to determine metrics of interest associated with a microcolony (e.g. circularity, area, major axis, and minor axis). There are many different example algorithms that can be used to calculate the threshold in a bias-free manner. The Phansalkar thresholding method is a modification of Sauvola's thresholding method optimized for low contrast images [Phansalskar, N; More, S & Sabale, A et al. (2011), "Adaptive local thresholding for detection of nuclei in diversity stained cytology images.", International Conference on Communications and Signal Processing (ICCSP): 218-220, doi:10.1109/ICCSP.2011.5739305]. Other example methods include the Bernsen, Contrast, Mean, Median, MidGrey, Niblack, Otsu and Sauvola methods.

Alternatively, the presence of microcolonies can be based on convolutional neural network (CNN) method. One example is YOLO (You Only Look Once), which is a detection algorithm based on the "microcolony emergence episodes" which are prepared a priory by observing the early-stage growth evolution of prevalent microbial cells across many cases. Once the network is trained, it can interrogate a single image (the difference between the floating and reference image) for the presence of microcolonies. The training may be performed employing sample type, sample treatment method, solid phase growth media, cell-suspension-growth media contact procedure, and incubation condition similar to what is employed during actual testing. The present inventors have observed that under these conditions, the microcolonies emerge in a more or less repeatable manner for a given microbial species.

Steps 123, 131, and 132 may be repeated with scan period of $\Delta t$, for example, up to a pre-established maximum positivity time of $t_{p,max}$. The time $t_{p,max}$ may be selected to represent the case of common pathogenic bacteria. For example, as it is seen FIG. 10, this time can be as high as five hours for some example bacterial species. In order to achieve a sufficiently high confidence level regarding a determination of positivity, the time $t_{p,max}$ may be selected depending on the pathogenic species that are to be detected, and in some example cases, may be at least 3 hours, 4 hours, 5 hours, 6 hours, 7 hours, 8 hours, 9 hours, or 10 hours. In some example implementations, the time interval $\Delta t$ can be at least 15 minutes, at least 30 minutes, at least 45 minutes, and at least 60 minutes.

Steps 122-132 of FIG. 9B may be performed using any one or more optical imaging modalities that facilitate the detection of a microcolony, including, but not limited to, bright-field imaging, dark-field imaging, and phase-contrast imaging. After having detected and located a given microcolony, dark-field imaging is employed using an objective having an appropriate numerical aperture to facilitate the detection of complex, pathogen-specific morphological features.

In some example implementations, the initial scanning for the presence of microcolonies at step 123 may be performed with a low-resolution bright-field and/or dark-field mode in order to accelerate the scan time and/or reduce the amount of imaging data that is acquired. In such an example case, the dark-field images during step 124, after having identified a microcolony, are collected after changing to a dark-field objective having a suitable magnification and numerical aperture that facilitates the detection of complex, pathogen-specific morphological features.

In some example implementations, for each microcolony, a set of dark-field images are collected by repeating step 124, thereby generating a time-series of dark-field microcolony images that characterize the temporal evolution of the imaged complex microcolony dark-field morphological features. The dark field image acquisition of a given microcolony may continue, for example, until a time $t_{c,max}$ that is selected to be longer than the maximum positivity time $t_{p,max}$. In some example implementations, when a microcolony is detected at $t_{p,max}$, then $t_{c,max}$ will preferably be selected to be longer then $t_{p,max}$ by at least 1 cycle (e.g. one time cycle $\Delta t$) to allow the classification of the latest-detected microcolony (as multiple dark-field images will have already been obtained for earlier-detected microcolonies).

In some example implementations, different microcolonies detected at different times may be separately classified at different times, provided that for each microcolony, a sufficient number of time-lapse dark-field microcolony images are acquired for performing classification. Alternatively, image acquisition for classification may continue for all microcolonies until the time $t_{c,max}$. In such a case, the microcolonies detected earlier, which may have gone through more phases during imaging, may be classified with higher accuracy. In some example implementations, it may be beneficial to acquire the same number of dark-field image for each microcolony regardless of its detection time. For example, this approach may be beneficial in situations in which an early determination of positivity of the sample is desired.

As explained above, the present example classification methods employ one or more microcolony images obtained during the dynamic phase of microcolony growth, in contrast to obtaining and processing colony images when the colony morphology is static. The difference between these two modes could be understood by referring to FIG. 7A which presents the evolution of a microbial colony grown on the solid-phase growth medium. At the early stage of the growth, which is labelled as microcolony stage, often the microcolony undergoes substantial morphological or structural changes such that its image at a given acquisition time of $t_p + j\Delta t$ is not a scaled version of its image at the earlier acquisition time of $t_p + (j-1)\Delta t$ in terms of spatial and/or scattering intensity. Here $t_p$ is the time when microcolony was detected. After transition to the colony stage, the colony size keeps increasing while it does not undergo substantial morphological or structural changes. For the typical bacterial species this transition occurs around the colony size of 150-200 µm.

Referring again to FIG. 9A, dark-field images of detected microcolony images are processed to determine a classification of the microcolony, as shown at 140. Underlying mechanisms for differentiating between classes of pathogenic microbial cells are related to their characteristic attributes and include, but not limited to, cell wall composition, cell shape, cell motility, and composition of the extracellular matrix.

The determination of a class may be referred to as a "presumptive identification" or "presumptive classification" when a subsequent classification modality, having either a higher confidence/accuracy or a larger set of classes, is subsequently performed. It will be understood that the class of the cells may be determined based on colony morphology or other techniques. As noted above, the present presumptive identification or presumptive classification step may result in the classification of the microbial cells, prior to cell harvesting, into a cell class such as Gram-positive bacteria, Gram-negative bacteria, fungi and optionally a subclass encompassing one or more species. The commonplace Gram stain test is an example of presumptive identification.

As described below, characteristic (engineered) features, such as spatial, temporal and intensity features, may be optionally extracted and employed for classification, as shown at 130.

The present inventors performed experiments to study the potential of employing engineered features extracted from time-dependent microcolony images for the classification of microbial pathogens. An example set of Gram-positive and Gram-negative bacteria, which had been prepared according to the method of Example 4, were grown on the selected solid-phase growth media with the respective agar concentrations of 1.5%, 1.75%, and 2% w/v, which had been prepared according to the method of Example 2. The example Gram-positive and Gram-negative pathogens included American Type Culture Collection (ATCC) strains and hospital clinical isolates (MSH) of Gram-negative species (*Escherichia coli* EC ATCC 35218, *Klebsiella Pneumoniae* KP MSH CRE 1705) were each having approximately 10 microcolonies under field of view, and 3 American Type Culture Collection (ATCC) strains of Gram-positive species (*Staphylococcus Aureus* SA ATCC 25923, *Enterococcus Faecalis* EF ATCC 51299, *Staphylococcus Epidermidis* SE ATCC 12228).

For every strain 1 μL of the sample was dispensed on the solid-phase growth media residing on plates. The plates were placed into the incubator and regularly imaged via reflective dark field imaging with a 10× objective and NA 0.25. The imaging and analysis were performed at 3, 4, and 5 hours after seeding. Multiple images were collected (multiple FOIs) to obtain a net field of view (FOV) containing approximately 10 microcolonies.

The collected image data was processed to identify microcolonies and to estimate set of example characteristic (engineered) features that may be suitable for the classification of the microbial cells within the microcolony. After converting an image into a greyscale image, flat- and dark-field correction was performed and the greyscale image was binarized by applying local adaptive image thresholding according to Phansalkar method, based on histogram analysis of intensity levels.

In general, a non-limiting list of example extracted parameters (e.g. engineered features) may include any one or more of the following example features:

microcolony perimeter, calculated, for example, as the distance around the boundary of the region associated with microcolony;

microcolony effective diameter, calculated, for example, as the of a circle with the same area as the spatial region associated with microcolony (e.g. calculated as $\sqrt{4 \cdot Area/\pi}$);

microcolony fractal dimension (or fractal measure), calculated, for example, as the longest diameter of spatial region associated with microcolony;

microcolony area, calculated, for example, based on the number of pixels within a segmented region associated with microcolony, or an equivalent areal measure;

microcolony bounding box, calculated, for example, as the position and size of the smallest box containing the region associated with microcolony;

microcolony centroid, calculated, for example, as the location of the center of mass of the region associated with microcolony;

microcolony circularity, calculated, for example, as the roundness of the region associated with the microcolony (e.g. $(4 * Area * \pi)/(Perimeter^2)$);

microcolony eccentricity, calculated, for example, as the eccentricity of the ellipse that has the same second-moments as the spatial region associated with the microcolony;

microcolony minor/major axis length, calculated, for example, as the length of the minor/major axis of the ellipse that has the same normalized second central moments as the spatial region associated with microcolony;

microcolony statistical intensity measure(s), calculated, for example, by generating one or more of the maximum, mean, median, and minimum intensity over the region associated with microcolony; and microcolony height, calculated, for example, via collecting and processing images at multiple axial objective locations (e.g. multiple focal planes).

The calculated measures representing circularity and mean dark-field scattering intensity (labelled DF intensity) are presented in FIG. 11A-11B. The stratification via both parameters to the Gram-positive and Gram-positive classes is observed for all incubation times and agar concentrations. As can be seen in the figures, the circularity measure differs significantly among the example Gram-positive and Gram-negative species, while the dark field scattering intensity measure exhibits less of a clear distinction among the different Gram status. It is also observed that the solid-phase growth medium with a 2% agar concentration resulted in the clearest distinction between Gram-positive and Gram-negative species based on these two example features.

In order to explore the suitability of a given engineered feature (parameter) for use in classification, biplots were prepared and employed to qualitatively assess the differences between Gram-positive and Gram-negative classes for the given parameter. Biplots in FIG. 11C show that perimeter, area, radius and fractal are dependent parameters, collectively known as dimension metrics, while circularity and dark-field (DF) scattering intensity are independent features of the microcolonies. Accordingly, in some example implementations, suitable engineered features for use in classification may include: normalized dark-field (DF) intensity with respect to the selected channels; shape-factor/circularity; and a dimension metric.

While the preceding example embodiments pertained to the use of engineered features, it will be understood that machine learning may additionally and/or alternatively be employed to extract suitable parameters for the classification of microcolonies via dark-field images of complex microcolony morphological structure. For example, a machine learning module can be employed to extract features directly from images, such as a model based on a convolutional neural network (CNN).

Moreover, while many of the example embodiments described herein relate to microcolony classification based on the processing of dark-field images obtained of microcolonies growing on one type of solid-phase growth medium, a given microcolony suspension may be dispensed onto two or more different types of solid-phase growth media. Non-limiting examples of different types of solid-phase growth media include chromogenic culture media, which contain chromogenic substrate which is utilized by the microorganisms to give colored colonies that is specific for a class of microorganism. Moreover, the media may have been supplemented with agents for promoting or suppressing the proliferation of specific class. For example, differences in microcolony morphology for microcolonies grown from a common sample, but from grown on different types of solid-phase growth media may be employed to improve the classification accuracy. Additionally or alternatively, a given microcolony suspension may be dispensed onto at least two solid-phase growth media (which may have the same composition) and which are subjected to different environmental conditions (e.g. a different temperature and/or humidity) during microcolony growth. Non-limiting examples of different environmental conditions include incubation temperature between 30-40° C., or, for example, between 33-37° C. The relative humidity may be selected to be more than 30%, or, for example, more than 40%.

In some example embodiments, a set of images obtained at different times during the growth of the microcolony may be classified, using a machine learning algorithm, based on multiple time-ordered phases of microcolony morphology in dark-field images. Such classification may involve comparison with, and/or training by, a reference dataset (e.g., library) based on multiple time-ordered phases of microcolony morphology in dark-field images collected from known (labeled) microbial pathogens.

Accordingly, if many microcolonies, having known classifications, are imaged over a period of time sufficient to capture multiple phases of evolution (e.g. at least 1 hour, preferable at least 2 or 3 hours) at sufficiently short intervals (e.g. less than 45 minutes, less than 30 minutes, or less than 15 minutes), a set of possible morphologies will be available for training the system to perform microcolony classification. Dark field images of an unknown microcolony, recorded at two or more different times during the growth of the microcolony, forming an unknown microcolony dark field image set, may then be processed by the classification algorithm.

Various example methods of performing dynamic classification are described below. In one example embodiment, a machine learning algorithm, trained with a reference image set of labeled dark field images of microcolonies from known microbial cells, such that the reference image set includes dark field images from different phases of microcolony growth for different cell types, can be employed to separately classify, or generate a classification score, for each image of the unknown microcolony dark field image set.

For example, an unknown microcolony dark field image set may include three images of a microcolony at 0.5 h, 1 h and 1.5 h after microcolony detection. Each image may be provided to a convolutional neural network (CNN) trained via the reference image set. The CNN may generate, for each image, a probable classification. The final classification determination may be selected to be the mode of the classifications from the individual images. Alternatively, the CNN may generate a set of probabilities for each image, each probability in the set of probabilities denoting the probability that the particular image is associated with a given class. The per-class probabilities from each image may be combined (e.g. multiplied) to generate a final set of per-class probabilities, and the classification may be determined as the class corresponding to the highest per-class probability of the final set of per-class probabilities. It will be understood that the preceding example implementations are merely illustrative and that other methods of generating a final classification determination from a set of separation classification measures may be employed in the alternative.

It will be understood that various different types of machine learning algorithms may be employed to generate the classification measures. For example, while the previous example refers to a CNN, other example machine learning algorithms suitable for classifying the unknown microcolony dark field image set include, but are not limited to, k-nearest neighbour classifiers, logistic regression classifiers, and support vector classifiers. In some example implementations, engineered feature extraction may be performed prior to classification.

Another example algorithm for performing microcolony classification based on dark field images is a Siamese neural network (e.g. a one-shot neural network). For example, a Siamese neural network may be trained based on a set of labeled reference dark field images. In one example implementation, a triplet loss function may be generated, for example, using reference dark field images from different microbial classes as the negative images, and reference dark field images from the same microbial class, but from adjacent time points, as anchor images.

An example method of generating a machine-learning-based microcolony classification model that employs dark-field microcolony images is presented in FIG. 12A. In step 200, the microcolonies of representative species of the selected classes are prepared and are imaged for a plurality of samples. The selection of species for the study is done according to the final application. For instance, if the final application is the classification of pathogenic microbial cells in the blood according to bacterial/fungal class and, for bacterial pathogens, Gram status class, the example classes are {Gram-positive, Gram-negative, Yeast}, and an example target list may be as follows: Gram-positive training species: *Enterococcus faecalis, Enterococcus faecium, Staphylococcus aureus, Staphylococcus epidermidis, Staphylococcus haemolyticus, Streptococcus agalactiae, Streptococcus pneumoniae, Streptococcus pyogenes*; Gram-negative training species: *Acinetobacter baumannii, Enterobacter cloacae* Complex, *Enterobacter aerogenes, Escherichia coli, Klebsiella oxytoca, Klebsiella pneumoniae, Pseudomonas aeruginosa, Serratia marcescens, Proteus mirabilis*, Yeast training species: *Candida albicans, Candida glabrata, Candida parapsilosis, Candida tropicalis, Candida krusei*. The number of microcolony images obtained within each class necessary for reliable classification may be over 100, or higher, such as over 1000.

In step 210, features of the microcolonies are extracted. In some example implementations, one or more features can be obtained by applying one or more filters to the images.

In step 220, at least a subset of the features may be selected (e.g. manually selected), through the hidden layers of CNN, or randomly with the goal of avoiding issues such as overfitting due to excessive number of parameters. The selected features are compared across the classification classes and a figure of merit, typically in the form of prediction strength or probability, is determined in stage 230 for assessing the suitability of the feature subset. If the figure of merit is in the desired range, the feature subset, along with the associated weight and their extraction procedures, are taken as the "classification model". Alternatively, a new feature subset may be selected and the steps 210-235 are repeated.

As explained above, in one example implementation, a classification model may be prepared using a convolutional neural network (CNN), as shown in FIG. 12B. In such an example case, the characteristic features are extracted from the imaging data directly and automatically by applying appropriate image processing operations (within input and hidden layers) and subset of these features is retained and grouped for each target class (within output layers). Accordingly, feature extraction and selection of the flowchart in FIG. 12A is performed within the network automatically and directly from the imaging data 300. Typically, input 305 and hidden 310 layers form the convolutional base of the network and are composed of convolutional and pooling layers. The output layers 315, which generate classified output 320, forming the classifier and are composed of fully connected layers. The network is trained on the training dataset (library of labeled images). When attempting to classify an unknown microcolony using the classification model, the dark-field images of the microcolony are employed at a pre-determined time point and after extracting features via transfer functions belonging to the classification model, the classification is performed by comparing these features to the reference features within the model. In this procedure, a classification and its figure of merit C is generated. It is noted that the example method illustrated in FIG. 12B does not incorporate time-dependent changes in microcolony morphology, and examples of such time-dependent models are provided below.

An example implementation of the method shown in FIG. 12A is illustrated in FIG. 12C. In this example implementation, an existing (pre-trained) CNN is employed, non-limiting examples of which include, Xception, VGG16, ResNet152V2, InceptionV3, MobileNetV2, DenseNet201, NASNetLarge, EfficientNetB7. Once the CNN is selected, it is modified, commonly by replacing the original classifier (e.g. Gram-positive, Gram-negative and Yeast), and either the entire model or only individual layers are re-trained on the new training data. During re-training weights of the layers under the training will be re-adjusted and classification model is created.

FIG. 12C is a flowchart representing a basic workflow for building the classification model of FIG. 12A based on pre-trained convolutional neural network (CNN). In step 350, the pretrained network is downloaded from a library. In step 355 the network is modified to conform with the typical images obtained throughout the experiments with microcolonies. In addition, the output layer is modified to include the desired classes. In step 360 the validation and training data set are generated by performing tests on samples containing microbial cells with known identifications. These sample may be selected from spiked samples or real patient samples which undergo extra tests for identifying its microbial content. In step 362, the training algorithm is selected. In step 365, the network is trained by loading the training data. In step 375 the validation data are loaded to the trained network and the network's classification is assessed. In step 380, a determination is made as to whether or not the performance level is sufficient, and if the classification accuracy satisfies selected criteria, the model is employed for classification of unknown microcolonies, shown at step 390.

FIG. 13 illustrates two example methods for obtaining appropriate reference images for training a machine learning algorithm that utilizes a temporal-ordering of dark-field microcolony images for microcolony classification.

According to a first example approach, which is labeled as "ensemble" in FIG. 13, a sufficiently large number of microbial cells are spiked into the biological sample and a cell suspension is obtained following the relevant sample treatment method. The cell suspension is seeded on the solid-phase growth medium and is incubated. The solid-phase growth medium is scanned until microcolonies are detected, for example, in an amount that represents a significant fraction (e.g. at least 70%, 80% or 90%) of the expected microcolonies, at time $t_{p,maj}$. Here, the term "expected number" is intended to refer to the number of colonies when the colonies are counted after overnight incubation. Evidently, this number is not known during actual testing and the plates will be read until a pre-set $t_{negative}$ when based on experimental observations the emergence of a microcolony is not expected to a selected confidence level for the given sample type. For instance, the present inventors have observed that for whole blood samples spiked with the relevant blood stream pathogenic bacterial and fungal cells the likelihood of detecting a microcolony before $t_{negative}=6$ hours is less than 5%. Alternatively, multiple experiments may be performed and a time at which a majority of the microcolonies are detectable positive may be determined experimentally. During the acquisition of dark-field images for the library, the dark-field images of detected colonies are acquired and included in the ensemble, which is fed to the library as the representative of the target microbial cell. Each of these example approaches are expected to be suitable for generating a set of labeled microcolony dark-field images that are inclusive of different phases of microcolony growth.

In a second approach, which is labeled as "Time stamped", microbial cells are spiked into a biological sample and a cell suspension is obtained, e.g. following a suitable sample treatment method. The cell suspension is then seeded on the solid-phase growth medium and is incubated. The number of microbial cells may be, for example, in the range of 20-200, for the case of a growth media having a surface area of about 10 cm$^2$ (which can be scaled for other growth media area values) such that while avoiding the microcolony overlap, the number of images is sufficiently high enough for statistical significance. The solid-phase growth medium surface is then scanned for microcolonies as described above, for example, as in step 123 of FIG. 9B. The first colony is detected at $t_p$, following which, at time $T_p$ (which can be immediately after determining positivity), an initial dark-field image of the microcolony is acquired for the library, with successive dark-field images of this microcolony being acquired at regular times separated by an interval Δt. A similar process is repeated for all microcolonies which emerge, until the last microcolony is detected at a time less than $t_{p,max}$. A final round of dark-field images may then be recorded and provide to the library for training. The library thus includes time-ordered dark field images that represent the possible morphologies of a typical microcolony during its temporal evolution.

The preceding example discussions pertain to models that employ a single microcolony image. However, the present inventors have found that improved results can be obtained using dynamic classification methods, described in detail below, for which a time-ordered series of dark-field images of microcolony, obtained during the microcolony growth phase, are processed to perform classification. Such dynamic approaches may be beneficial in providing a higher level of discrimination due to increased specificity and may provide classification results in shorter time scale. Some of the present example dynamic classification methods are based on a model of microcolony growth whereby a microcolony of a given microbial strain proceeds via substantially deterministic morphological and structural phases (stages) independent of its positivity time, for example, provided that the method of separation of the bacterial cell from the sample matrix and/or seeding process and the composition of the solid-phase growth medium and ambient incubation conditions are controlled. Various example methods of performing dynamic classification are described below.

In order to employ a machine learning model that utilizes multiple dark-field microcolony images, obtained during microcolony growth, for microcolony classification, the reference dark-field image library may include, for different microbial cell types of interest, dark-field images representing a set of different characteristic phases of microcolony development. Such images may be manually determined, for example, by selecting, from a set of images obtained at different time points after microcolony detection, a set of representative images that characterize the phases of microcolony development and the different characteristic microcolony morphologies in dark-field images.

In one example implementation, an unknown microcolony dark-field image set may include at least two (or, for example, at least three, up to N) dark-field microcolony images (labelled Image 1, Image 2, Image N on FIG. 14A) obtained at different time points during the microcolony growth phase (e.g., 0.5 h, 1 h and 1.5 h) after initial microcolony detection. In this case classification is performed on time series and is called time series analysis. As it is shown on FIG. 14A, each dark-field microcolony image may be provided to a CNN trained or re-trained via a reference/validation image dataset that includes microcolony images obtained at different times during incubation, but without temporal labels. The CNN may generate, for each image, a probable classification and strength of prediction in the form of figure of merit.

One example implementation of such an embodiment, represented in FIG. 14B, is based on "single frame" analysis method. In this example implementation, images from a time-lapse series are separately interrogated by the classification model, as shown in step 400. For each image in the time series, a corresponding initial per-image class is determined as the class having the highest associated strength of prediction classification score (e.g. in the form of figure of merit), as shown at step 405. The initial per-image class and associated classification scores of the images are processed to determine a final class determination for the imaged microcolony. For example, the among the initial per-image classes determined for the images, class with the highest associated strength of prediction score measure may be reported as the final class corresponding to the imaged microcolony.

Another example implementation of this embodiment is represented in FIG. 14C and is based on joint strength of prediction. In this case, the classification model may generate, for each image, a set of per-class "strength of prediction" classification scores, with each per-class classification score denoting the probability that the particular image is associated with a given class, as shown in steps 450 and 455. The sets of per-class classification scores for the images may be combined (e.g., multiplied, averaged) to generate a final class determination for the imaged microcolony, as shown at step 460. For example, a final set of per-class "strength of predictions" classification scores maybe determined for the image set, and the final class may be determined as the class corresponding to the highest per-class strength of prediction classification score of the final set of per-class strength of predictions classification scores, as shown at step 465.

It will be understood that the example methods illustrated in FIGS. 14B and 14C are intended to be non-limiting examples in which a machine learning model is trained based on temporally-unlabeled microcolony time series dark-field image data having pathogen-class labels, and employed to perform classification of a time series of dark-field images of microcolonies having an unknown pathogen class.

While some example classification methods only retain the microbial class as a label when generating the reference data set (and when training the algorithm), other example embodiments may employ the temporal ordering of the dark field images in the reference image dataset. This ordering can be important in providing additional specificity when performing classification. For example, two different microbial cell types may generate dark field microcolony images with similar morphology at two different phases of their respective evolution, which may result in reduced specificity when the temporal ordering of the reference dark field images is discarded. However, if temporally adjacent dark field images of both the reference image data and the unknown microcolony dark field image set are employed during classification, the specificity can be increased, since it will be less likely that differing cell types have similar morphologies in temporally adjacent images.

In one example embodiment, a Siamese neural network may be employed to generate improved specificity. When an unknown microcolony dark field image set is processed, the temporally ordered set of sequential unknown images may be compared with a respective temporally ordered set of reference images. This may be repeated using different temporally ordered set of reference images for different cell types. For example, when an unknown microcolony dark field image set includes three dark field images, namely unknown images 1, 2 and 3, these images may be respectively compared with temporally ordered reference images 1, 2 and 3 for an *E. coli* cell, thereby generating a first set of classification measures. Unknown images 1, 2 and 3 may then be respectively compared with temporally ordered reference images 2, 3 and 4 for the *E. coli* cell, thereby generating a second set of classification measures. This process may be repeated for temporally ordered combinations of reference images from other cell types, and the resulting sets of classification measures may be processed to determine a probable class of the unknown microcolony. For example, each set of classification measures may be combined (e.g. added, multiplied, or combined according to a weighted function), and resulting in a net classification measure, and the net classification measure with the highest score may be employed to determine the class of the unknown microcolony.

In order to employ a machine learning model that utilizes a temporal-ordering of dark-field microcolony images for microcolony classification, the reference image library should include, for different microbial cell types of interest, temporally-labeled dark-field images representing a set of different characteristic phases of microcolony development. Such images may be manually determined, for example, by selecting, from a set of images obtained at different time points after microcolony detection, a set of representative and temporally-labeled images that characterize the phases of microcolony development and the different characteristic microcolony morphologies in dark-field images.

While some example classification methods disclosed herein only retain the microbial class as a label when generating the reference data set (and when training the algorithm), for example, as illustrated above in FIGS. 14B and 14C, other example embodiments may employ the temporal ordering of the dark-field images in the reference image dataset wherein training the model and performing classification. This temporal ordering can be beneficial in providing additional specificity when performing classification. For example, two different microbial cell types may generate dark-field microcolony images with similar morphology at two different phases of their respective evolution, which may result in reduced specificity when the temporal ordering of the reference dark-field images is discarded. However, if temporally adjacent dark-field images of both the reference image data and the unknown microcolony dark-field image set are employed during classification, the specificity can be increased, since it will be less likely that differing cell types have similar morphologies in temporally adjacent images.

Accordingly, a temporally recurrent machine learning algorithm, such as a recurrent neural network (RNN), may be employed to process temporally-ordered image sets, instead of individual images, such that the ordering of the unknown microcolony dark-field image set is employed during classification (see FIG. 14D). When an unknown, yet temporally ordered, microcolony dark-field image set is processed, the temporally ordered set of sequential unknown images may be compared with a respective temporally ordered set of reference images covering microcolony phases with large granularity. For instance, the test image set might have only three time points (Image 1 acquired at $t_1$, Image 2 acquired at $t_2$ and Image t acquired at $t_n$). In contrast to classical feedforward CNN, shown on FIG. 12B, or passing multiple time points to CNN, shown on FIG. 14A, which has only connections from input to output. The RNN shown on FIG. 14D has connection from output to input. The RNN the feedback connection to store information and pass information over time. Referring now to FIG. 14D, an example machine learning network architecture is shown that employs a recurrent neural network (RNN) for processing temporally-ordered sequences of dark-field images. Unlike a standard CNN, the RNN incudes feedback connections and can process entire sequences of images to capture and correlate features among multiple microcolony images in a time series.

FIG. 14E illustrates a method of processing temporally-ordered sequences of dark-field images using the example RNN shown in FIG. 14C. As shown in step 500, acquired time-lapse images are fed to the classification model. The images could be fed either in one-by-one (as the data is acquired) or all together as a video file after microcolony has reached the colony stage. During step 505, convolutional layers of a CNN extract features from each image.

In step 510, the video sequence is converted to feature vectors, for example, using a convolutional neural network (CNN). The CNN may or may not be pre-trained. an example of pre-trained networks include, but not limited to, Inceptionv3, Nosnetlarge, GoogLeNet, and Darknet53. The extracted features from individual images are combined together in image the sequence unfolding layer. Then, flattening may optionally be performed, with the data being converted into a 1-dimensional array for inputting it to the next (temporal) layers in step 510.

In step 510, which occurs in a recurrent neural network (RNN), the features are arranged in vectors, whose components are ordered according to the acquisition time.

In step 520, the RNN classification model performs classification based on feature vectors and generates strengths of prediction for every class.

In step 520 the class with the largest corresponding probability is chosen.

In one example embodiment, as a new image (acquired at time point $t_n$) is added to the image set (containing images taken up to the time point $t_n+1$), the set is compared with the reference set. If the returned classification accuracy, indicated by the "strength of prediction" in the form of figure of merit, is deemed sufficient the imaging may no longer proceed with data acquisition at further time points.

In some example implementations, the recurrent neural network may include or employ a long short-term memory (LSTM) network. LSTM is a type of RNN that is efficient in storing information over extend time intervals. Each LSTM block, see FIG. 14F, consists of a forget gate, input gate and an output gate.

One example implementation of a recurrent neural network method that includes an CNN and afterwards RNN (LSTM+CNN) is illustrated in FIG. 14G. As shown in the figure, the example network architecture includes a CNN as a feature extractor and a long short-term memory (LSTM) network for recurrent processing. In this example implementation, a CNN is provided as a feature extractor for the LSTM network. As shown in the figure, the classification procedure begins with providing a first microcolony image, shown at 700 and acquired at $t_1$, to the CNN, as shown at 705. The CNN 705 performs single image classification, generates a feature vector, and determines the class along with strength of prediction.

As shown at 710, if the strength of prediction satisfies the accuracy criteria, there is no need to continue with processing the next images in time series.

However, if the strength of prediction is below the required accuracy, as shown at 715, the feature vector is transferred to the LSTM network, as shown at 720. As shown at 725, the second image, taken at $t_2$, is fed to the CNN, which from now only performs feature extraction of this second image and does not perform classification. After extracting the feature vector from the second image, the feature vector is sent to the LSTM network, as shown at 730.

As shown in the figure, when processing the second image, the LSTM receives two feature vectors as shown at 720 and 730, namely one corresponding to the image acquired at $t_1$ and the other corresponding to the image acquired at $t_2$. The LSTM performs classification based on these feature vectors (which by now has two temporally ordered components, one fort, and the next for $t_2$).

As shown at 735, the LSTM outputs classes and corresponding strengths of prediction. If the strength of prediction satisfies the accuracy criteria, as shown at 740, there is no need to continue with processing the next images in time series.

However, if the strength of prediction is below the required accuracy, as shown at 745, the next image, taken at $t_3$, is fed to the CNN, as shown at 750, and its feature vector output is fed to LSTM, as shown at 755. This step adds a new component to the previous feature vectors and the classification is again performed. This process is contained in recurrent fashion until either the desired classification accuracy is reached or the image acquisition is aborted.

The time-lapse imaging dataset of a microcolony growth contains all imaging data for the given microcolony acquired since its detection in a time-stamped sequentially manner. In the example CNN-LSTM implementation described above, a pretrained CNN (or convolutional layers of inceptionv3) may be employed to convert video sequence to the feature vectors/tensors via extracting features from each image. A sequence folding layer and unfolding layer may be used before and after convolutional layers to re-introduce vectoral sequences. To restore the sequence structure to vector sequences, an unfolding layer and a flatten layer may be used. In this implementation, the actual classification is performed by long short-term memory (LSTM) on vector sequences.

1. In some example implementations, the example LSTM-based network architecture described above and shown in FIG. 14G could be trained as follows. Download the selected pretrained network. Disable all layers of the network, except the input and convolutional layers, thus transform it to a feature extractor.
2. Treat patient samples and/or samples spiked with microbial cells typically encountered in patient samples employing protocols similar to what will be employed during actual test testing. Dispense the resulting cell suspension on the appropriate solid phase and acquire bright field (optional for earlier detection) and time lapsed microscopic image of the surface wile incubating the solid phase in appropriate temperature and relative humidity Perform multiple tests, preferably over 20, for each microbial target.
3. Divide the acquired images for every large into two groupings of "training" and "validation".
4. Feed the images belonging to "training set" to the modified neural network, which acts as feature extractor.
5. Inspect the extracted feature vectors and select those features, which are different at least for two microbial species of interest. This operation can be performed by referring to biplots obtained through component analysis. In this way only a set of features will be retained as the relevant set.
6. Allow the network to train itself by re-analyzing the images employing only the relevant features to adjust the weights assigned to each layer parameter.
7. Prepare temporal vector for each relevant feature and for each class.
8. Download the selected pre-trained recurrent network (e.g. LSTM), adjust the input parameters in terms of vector dimension etc. and feed the feature vectors of the previous step into it for training the network for classification.

FIG. 15A demonstrates performance of the example CNN-LSTM architecture for the dynamic classification presenting the confusion matrix for classing the selected ATCC strains and clinical isolates (MSH) of Gram-positive bacteria, tabulated in FIG. 15B, Gram-negative bacteria, tabulated in FIG. 15C, and Yeast, tabulated in FIG. 15D, down to Gram-stain level {Gram-positive, Gram-negative, Yeast}. For the experiment, 8 ATCC stains and 8 clinical isolates (MSH) of Gram-positive organism, 9 ATCC stains and 9 clinical isolates (MSH) of Gram-positive organism, and one ATCC stain and one clinical isolate (MSH) of Yeast, prepared according to the method Example 5, were seeded into the 2% w/v agar-based solid-phase growth medium, which had been prepared following the method of Example 2. 1 µl of every cell suspension was dispensed on individual plate with solid-phase growth medium and allowed to be absorbed on the surface The plate was placed in into the incubator and imaged every 30 minutes (0, 1.5, 2, 2.5, 3, 3.5, 4, 4.5 hours after seeding) by taking 4×6 images across the gel surface. Dark-field images were aligned and registered, and microcolonies were detected according to the method of Example 3. All parts of FOIs belonging to the same microcolony were rescheduled to 350×350 pixels (small part of FOI containing only this microcolony) and arranged in a time-stamped sequential format (video fragment) containing 8 dark-field images.

With the network (pretrained GoogLeNet model), video was converted into the feature vector using convolutional layers as a feature extractor (feature vectors are the output of the activations function on the last pooling). Feature sequences that were much longer than typical sequences associated with the data were removed. Following sequence folding and flatten layers, feature vectors were classified by the LSTM. The training options that were implemented were as following: mini batch size=16, initial learning rate=et Gradient threshold=2, Shuffle=1 (on every iteration).

Example System for Microcolony Detection and Performing Presumptive Identification An example microbial incubation and monitoring system for incubating and detecting microcolonies and performing presumptive identification is schematically presented in FIG. 16. The system includes an imaging subsystem 810 and an open or closed incubation chamber 801 capable of housing and incubating solid phase growth medium 803 for microcolony growth thereon.

The optical subsystem includes at least one dark-field objective having a numerical aperture capable of collecting complex morphological microcolony features, as described above. For example, the numerical aperture of the dark-field objective may be within the range of 0.16 and 0.28, or for example, between 0.2 and 0.3, or for example between 0.18 and 0.32, or for example between 0.15 and 0.35, and the magnification of the dark-field objective may be in the range of 5× to 20×. The optical subsystem, and/or the incubation chamber, includes at least one translation stage or other scanning mechanism for moving the dark-field objective 808 relative to the solid phase growth medium 803.

As shown in the figure, the imaging subsystem 810 and optionally one or more environmental control devices of the incubation chamber are operatively coupled to control and processing circuitry 600, as shown at 690 and 692, respectively. The control and processing circuitry 600 may include a processor 610, a memory 615, a system bus 605, one or more input/output devices 620, and a plurality of optional additional devices such as communications interface 635, external storage 630, data acquisition interface 640 and a power supply 660. The example methods described above can be implemented via processor 610 and/or memory 615.

The imaging system 810 may be include an autofocus mechanism, such as, but not limited to, a linear motor that is driven according to optimal focus measure-based close-loop or open-loop feedback associated with one or more images. The autofocus mechanism can include a translational stage 811 that moves the solid-phase growth medium relative to the objective in the vertical (z) direction in addition to moving the solid-growth medium relative to the objective in at least one lateral scanning direction (x and y directions; horizontal). Although the example figure shows the solid-phase growth medium as residing on a movable support that moves in relation to the objective, it will be understood that the objective may be controlled to move in relation to the solid-phase growth medium.

The imaging system may include 801 or more illumination sources, such as tungsten-halogen bulbs, arc lamps, laser light sources or light-emitting diodes (LED). Wavelength and other properties selection might be guided by scattering and absorption properties of light by irregular particles and periodic arrangement of irregular particles (multi-sphere clusters)—(i) maximization of distance between dominant wavelengths; (ii) visible light spectrum (415 nm-740 nm); (iii) maximization of the collimated power output (iv) narrow band/monochromatic (bandwidth FWHM<30 nm). The present example system, or variations thereof, may be employed for hyperspectral imaging. An example monitoring system might be equipped with two LED illumination sources to produce narrow-band illumination centered around wavelength of 445 nm and 623 nm, with a spread of approximately ±23/2 nm and 17/2 nm, respectively, at the full-width-half-max level. Alternatively, a royal blue 445 nm LED might be employed as light with a shorter wavelength is expected to be scattered by the microcolony more strongly than that with longer wavelength. Alternatively, one or more halogen light sources may be used.

As shown in FIG. 16, executable instructions represented as image acquisition and processing module 680, microcolony classification module 682, and environmental control module 684 are processed by control and processing circuitry 600 to execute instructions for performing one or more of the methods described in the present disclosure, or variations thereof. Such executable instructions may be stored, for example, in the memory 615 and/or other internal storage. For example, image acquisition and processing module 680 may include executable instructions for controlling the scanning, autofocusing, image acquisition, image registration, focusing stacking, image subtraction, and/or microcolony detection, the microcolony classification module 682 may include executable instructions for implementing any of the example classification algorithms described herein, and the environmental control module 682 may include executable instructions for controlling one or more of temperature, humidity, flow rate of gases, or other environmental control measures, optionally based on feedback signals received from one or more environmental sensors, such as, but not limited to, temperature and humidity sensors.

The methods described herein can be partially implemented via hardware logic in processor 610 and partially using the instructions stored in memory 615. Some embodiments may be implemented using processor 610 without additional instructions stored in memory 615. Some embodiments are implemented using the instructions stored in memory 615 for execution by one or more microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing circuitry 600 may be provided as an external component that is interfaced to a processing device. Furthermore, although the bus 605 is depicted as a single connection between all of the components, it will be appreciated that the bus 605 may represent one or more circuits, devices or communication channels which link two or more of the components. For example, the bus 605 may include a motherboard. The control and processing circuitry 600 may include many more or less components than those shown. In some example implementations, some aspects of the example methods described herein, such as the classification of microcolony images, may be performed via one or more additional computing devices or systems, such as a mobile computing device connected via a local wireless network (such as Wi-Fi or Bluetooth), and/or a remote server connected over a wide area network.

Some aspects of the present disclosure can be embodied, at least in part, in software, which, when executed on a computing system, transforms an otherwise generic computing system into a specialty-purpose computing system that is capable of performing the methods disclosed herein, or variations thereof. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine-readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable storage medium can be used to store software and data which when executed by a data processing system causes the system to perform various methods. The executable software and data may be stored in various places including for example ROM, volatile RAM, nonvolatile memory and/or cache. Portions of this software and/or data may be stored in any one of these storage devices. As used herein, the phrases "computer readable material" and "computer readable storage medium" refers to all computer-readable media, except for a transitory propagating signal per se.

FIG. 16 illustrates a non-limiting example incubator 801. The incubator 801 may be closed by a removeable, sliding or permanent lid 802, and which houses one or more growth modules 803 placed on the heated base 804 directly or via an intermediate thermally conductive layer (e.g., water bath 812 to incubate growth module in water at a highly uniform constant temperature over a long period of time). The lid 802 may be transparent and sufficiently optically flat to avoid image distortion for imaging through the lid. The lid 802 may be heated to prevent condensation on the lid and may have an anti-condensation coating. The chamber may include one or more retention devices (e.g., clips or clamps) for firmly holding the growth modules. A heater, temperature sensor and associated control circuitry (not shown in the figure) may be employed to maintain temperature within an acceptable range (e.g., 35±2° C.), for example, via control by the control and processing circuitry 600. The gas composition and ambient humidity may also be regulated by connecting gas inlet and outlet ports 851 & 852 to one or more suitable external modules (e.g., gas mixture to control $CO_2/O_2$ to provide appropriate aerobic or anaerobic atmosphere; or a reservoir for water or other solution to control humidity 806).

In one example implementation of the system, upper and lower walls of the incubator may be supplied with a conductive coating and is heated by passing a current.

In some example embodiments, the example system may include two objectives that have different respective field of view. The first objective 807 has a first field-of-image (FOI) and associated magnification and the second objective 808 had a second FOI and associated magnification, with the second imaging module being a dark-field objective having a smaller field-of-image and a higher magnification than the first imaging module and a numerical aperture configured for imaging complex microcolony morphology. For example, the first and second imaging modules may be provided with optical magnifications of 5× and 10×, respectively. The first objective is scanned relative to the solid phase growth medium during a first microcolony detection phase in which microcolonies are detected and located, while the second objective is employed for dark-field microcolony morphology imaging after initial microcolony detection. The first objective may employ any suitable imaging modality that facilitates the detection of a microcolony, including, but not limited to, bright-field imaging, dark-field imaging, and phase-contrast imaging. In one example implementation, the first objective 807 may include a 5× bright-field objective that facilitates rapid scanning the surface of the solid-phase growth medium for detecting emergence of microcolonies.

In some example implementations, after placing the growth module 803 inside the chamber, the first imaging module 807 ('detection module') is moved by the control and processing circuitry 600 such that at least a portion of the surface of the solid-phase growth medium is within the field of view. In cases in which the field of view is smaller than the full surface of the solid-phase growth medium, the imaging module may be mechanically scanned during imaging (objective is moved with respect to the surface or surface is moved with respect to the objective) and the images may be combined using the control and processing circuitry 600 (e.g. mosaic stitching). For example, this task may be accomplished by stitching overlapping image parts (10%-30% overlap) from multiple fields of view. Due to a potential inaccuracy, misaligned individual fields of view might create misaligned final mosaic.

The control and processing circuitry may be programmed to compensate for the mechanical imprecision (linear motor backlash, and stage repeatability) and minimize stitching errors by optimizing the translations within a specified area via pairwise registration with a specified transformation constrains (e.g. translation only or translation+rotation). For example, the intensity-based or feature-based algorithm could transform every further image so that it is spatially registered with the previous image. In this context, the stage trajectory function provides a default configuration that can only be considered as a starting point.

The second imaging module 808 ('characterization module'), with a higher magnification than the first imaging module 807, is equipped with epi-illumination for supplementary dark field (DF) imaging with a single or multiple illumination sources. After the focus adjustment, higher resolution images (i.e. with a higher resolution than images obtained using the first imaging module) are acquired for presumptive identification based on or more properties of the acquired images (e.g. one or more spatial, morphological, and/or diffractive/scattering parameters of the imaged microcolony, optionally based further on time-dependent changes in such parameters). The present example system, or variations thereof, may be employed for imaging microorganisms tagged with fluorescent labels and/or unlabeled microorganisms.

In one example implementation, the example optical subsystem 10 system may include a single imaging module that is capable of being configured for both bright-field and dark-field modes of imaging. For example, such a reconfigurable bright/dark-field objective may be include a dual-pass illuminator such that by changing the path through known mechanisms one of the two modes is selected. Alternatively, the imaging system may be supplied by two illuminators and at any given time only one of the illuminators will be switched on. In one example implementation an objective with magnification of 7.5× is used and at each scanning position bright-field and dark-field images are acquired sequentially and the image analysis is performed later.

In another example embodiment, the bright-field images of the whole surface are acquired and evaluated for the presence of microcolonies. Then, the objective is brought to the location of the detected microcolony and dark-field image is acquired for identification purpose. The present example dual-mode imaging method (bright-field+dark field) is advantageous for benefiting the more rapid detection capability of the bright-field imaging, which amounts to about 1.5 hours. Whenever this feature is not deemed important the imaging may be performed in dark-field mode only.

While many of the preceding example implementations employ dark-field imaging of microcolony morphology for classification, it will be understood that in other example implementations, other one or more optical modalities, additionally or alternatively, may be employed to obtain a set of images during the microcolony growth phase, with classification being performed based on processing of such images. In some example implementations, bright-field imaging may be employed to collect such images, which while being expected to achieve poorer classification accuracy than approaches based on dark-field imaging, may nonetheless facilitate classification in some cases. In other example implementations, microcolony images may be collected, during the microcolony growth phase, according to a plurality of imaging modalities, and the multi-modality images may be employed for classification.

In some example implementations, at least one objective may be an immersion objective, that is, an objective that extends inside the incubator during the imaging. In such a case, the lid may include an opening for insertion of the immersion nosepiece. Furthermore, an objective heater 809 may be provided for an immersion objective. However, it is noted that an immersion objective, or without an objective heater, can act as a heat sink or source introducing a thermal gradient to the system.

While the previous example implementations pertain to systems in which the one or more objectives reside outside of the thermal incubator, or are insertable into the thermal incubator, in other example implementations, both the one or more objectives and the solid-phase growth module(s) may be provided with a common environmental enclosure, as illustrated, for example, by dashed line 820 in FIG. 16. In such a case, the temperature, gas composition and humidity may be controlled via recirculation.

Autofocusing Methods for Achieving Focus on Surface of Solid Phase Growth Medium As noted above, the optical subsystem 810 may include an autofocus mechanism. The present inventors have found that the optical properties of the typical solid-phase growth media surfaces can present challenges for implementing laser-based autofocus, and that image-based autofocusing mechanisms and associated algorithms may provide better results. Image-based autofocus algorithms seek a well-focused image that contains more contrast and/or finer details when compared to the images that are out of focus. In this case quality of focus could be estimated based on the optimal focus measure extracted from the imaging data.

The objective may be employed to acquire Z-stack images of a region of interest by axially scanning the microscope objective among a range of heights relative to the solid-phase growth medium surface (vertical offsets along the Z-axis) while acquiring a set of images at different heights. In some example implementations, the resulting Z-stack can be processed to determine one or more focus measures (e.g., image contrast, entropy, or spatial frequency content) associated with a quality of focus. The system can be acquiring images while calculating the focus measure, and choosing the image corresponding to the peak of the focus measure.

While there are various categories of autofocusing techniques, real-time image-based autofocusing is particularly promising approach considering the reflective properties of the solid-phase growth media. In one example implementation of the autofocusing, after acquiring the imaging data over various focusing steps (acquiring a Z-stack of images) and calculating a metric indicating focusing quality for every image of the Z-stack (e.g., absolute gradient, absolute variance, energy Laplace, Laplacian, Nettens filter, normalized absolute variance, normalized variance, square gradient, Tenegrads function, variance), an optimal focus position may be calculated via function fitting and optimization. As the choice of curve fitting model directly affects the number of images needed, empirical model requiring 3 images could be used. By repeating this focus searching process for a plurality of FOIs of the solid-phase growth media, well-focused images over large regions of the solid-phase growth medium can be obtained.

An example autofocusing method is provided below: (i) acquire Z-stack consisting of k images; (ii) determine focus measure for every image of Z-stack; and identify Z-stack image which is deemed to be in optimal focus.

In some example implementations, the search for an optimal focus may be performed in a stepwise manner involving a coarse initial search (e.g. 3 steps for 0.5 mm), subsequent fine searching with a smaller search stride (e.g. 3 steps for 0.25 mm), and optionally ultra-fine searching with a smaller search stride (e.g. 3 steps for 30 urn), and optionally extreme fine searching with a smaller stride (e.g. 3 steps for 10 urn). By repeating the present example Z-stack autofocusing process for multiple FOIs, a high-resolution, well-focused image of the solid-phase growth media can be obtained. In some cases, such methods can be employed to generate a composite focused image of the entire surface of the solid-phase growth medium.

In some example implementations, the autofocusing method may be performed to focus on the surface of the solid-phase growth medium by focusing on one or more of (i) residual debris particles (e.g. blood debris in the example case of processing a blood-derived sample) and (ii) localized features of the solid phase growth medium itself.

In some example implementations, as noted above, in order to facilitate autofocusing on the surface of the solid-phase growth medium, extrinsic particles may be introduced onto the surface of the solid-phase growth media. For example, algorithm that involves the focusing on extrinsic particles may provide superior results due to the increased contrast between the high intensity structures and background when compared to the focusing on a low contrast debris retained on or introduced to the solid-phase growth media.

The extrinsic particles may be configured to exhibit a high contrast relative to the surface of the solid-phase growth medium. Non-limiting examples of extrinsic particles include microspheres manufactured from various natural and synthetic materials, such as glass, polymers, metal microspheres, and ceramic. These extrinsic particles can be deposited on the solid phase during preparation or can be added to sample or cell suspension. In some example implementations, a mean particle diameter of the extrinsic particle may be in the range of 2 µm-50 µm, or, for example, in the range of 5 µm-20 µm.

Accordingly, in some example implementations, at least a subset of the surface features/artefacts employed for autofocusing may include any one or more of (i) inhomogeneities in the surface of the solid-phase growth medium, (ii) residual debris particles (e.g. residual debris from a lysis procedure in which endogenous cells in the sample are selectively lysed and microbial cells are preserved) arising from the sample processing, and (iii) extrinsic particles residing on the surface of the solid-phase growth medium.

In order to reduce the scanning time, in one implementation the solid-phase growth medium surface profile is prepared prior to actual imaging. This approach is schematically presented in FIG. 17. In this case, selected points on the solid-phase growth medium surface are imaged with employing autofocusing and acquiring a Z-stack of images for every point. The number of these points may be selected to be less than 10% of the total number of FOIs for imaging the whole surface. Then, fitting a mathematical function to the determined points the surface profile is generated.

Methods for Achieving High-Contrast Images of Microcolony Morphology

As noted above, autofocusing may be employed to locate, within a given FOI, a focal region associated with the solid-phase growth medium surface. However, as explained below, due to changes in the height of the microcolony during its growth, it may be beneficial to employ additional imaging processing methods to obtain microcolony images with high contrast across the spatial extent of the imaged microcolony surface. As it was presented above, the numerical aperture (NA) is a relevant parameter determining the suitability of an objective for recording the morphological features of microcolonies in dark-field microscopy. The numerical aperture of the objective is also a relevant parameter for selecting a suitable imaging procedure for imaging the morphological structure the solid-phase growth medium surface because of its relation to the depth of field (DOF), i.e. the distance between the nearest and the farthest objects that are in acceptably sharp focus in the image plane.

The DOF is related to the objective's numerical aperture NA through $$DOF = \frac{\lambda \cdot n}{NA^2} + \frac{n}{M \cdot NA} \cdot e,$$

where A is the wavelength of illuminating light (e.g., 550 nm), n is the refractive index of the medium (n=1 for air), e is the smallest distance that can be resolved by a detector/camera (e.g., pixel pitch of the microscope camera), and M is the lateral magnification of the objective. The diffraction-limited depth of field $$\left(\frac{\lambda \cdot n}{NA^2}\right)$$

is inverse proportional to the square of the NA, while the lateral limit resolution $$\left(\frac{n}{M \cdot NA} \cdot e\right)$$

is inversely proportional to the first power of the NA.

A suitable microcolony imaging method may thus be determined according to one or more parameters that include, but are not limited to, the depth of field (DOF), a statistical measure indicative of a typical size of the debris ($H_{debris}$), a statistical measure indicative of a typical height of microcolony ($H_{colony}$), the deviation of the solid-phase growth medium surface with respect to a plane normal to the optical axis of the objective ($H_{tilt}$), and the objective's field of imaging (FOI, which may be defined, for example, as the area of the objective's field of view which is recorded by the camera).

In some example implementations, having determined the location of the surface of the solid-phase growth medium, for example, using one of the autofocusing methods described above, a single in-focus image of a microcolony can be employed to capture the characteristic features of a microcolony provided that the DOF of the objective is larger than the quantity $H_{max}=K_{tilt}+\max(H_{debris}+H_{colony})$ within the FOI. However, when the DOF of the objective is less than the quantity $H_{max}=H_{tilt}+\max(H_{debris}+H_{colony})$ within the FOI, a single image will be insufficient to capture, in focus, the full set of morphological features that reside at different heights on the microcolony.

Indeed, as schematically shown in FIG. 18A, the solid phase growth medium surface is a two-dimensional manifold with a complex topology. The deviation of this surface from a plane can be substantial, for example, the present inventors have observed deviations exceeding 500 μm over the whole area of the solid-phase growth medium and a deviation of ~$H_{tilt}$=50 μm across the FOI. These variations can easily exceed the DOF of an imaging objective.

This aspect was experimentally investigated by spiking a whole blood sample with *Escherichia coli* EC ATTC 35218 microbial cells, according to the procedure of Example 1, and spreading the final cell suspension on an agar-based solid phase growth medium that been prepared according to the methods of Example 2. Imaging was performed employing a 10×DF objective with NA=0.25.

A typical image taken after 3 hours of incubation is presented in FIG. 18B. In this case, the imaging conditions and imaged properties were characterized as follows: FOI=0.42×0.42 mm, DOF=9.76 μm, $H_{debris}$~15 μm, with fluctuating changes in height along the diagonal indicated with an arrow (the direction of maximal changes in local tilt of the surface). As a result of the height variation, only the central region (along the diagonal perpendicular to the arrow) is in a sharp focus, with the profile of the microcolony at the upper-left corner being clearly out of focus. As can be seen from the image, it was only possible to obtain a focused image of a subset of the FOI using the example objective, and this objective would need to be translated vertically (in the height direction, along be optical axis of the objective) with at least 5 steps of 10 μm in order to image the entire FOI with sufficient accuracy.

In some example implementations, image processing methods may be employed to generate a composite image from a plurality of images acquired at different heights in order to improve the spatial and intensity characteristics (characteristic features) of the imaged microcolony. One example implementation of such an approach is to employ F-stacking (alternatively known as data-stacking, focus-stacking, Z-stacking, focal plane merging, zedification and image fusion), which is an image post-processing technique that combines image data acquired at different heights (thereby obtaining a set of distinct images, each corresponding to a different height/axial offset, referred to herein as a "Z-stack" of images) into a composite image using the 'sharpest' portions of each image. While in each image, only a small height would be in focus, the F-stacked composite (joined) image, generated from the Z-stack of images, contains the data equivalent to represent multiple image parts in focus.

The F-staking procedure is typically based on one of the following methods or their combination: methods based on spatial frequency (these methods are based on maximizing spatial frequency as an optimal focus measure); methods based on image pyramids (these methods are based on the multi-scale decomposition); methods based on defocus modeling (these methods are based on estimation of the parameters of the point spread function (PSF) of the imaging system); and methods based on wavelet transforms (these methods are based on the wavelet decomposition of Z-stack). In any of the previous example F-stacking methods, the following procedure is typically employed: (i) acquire Z-stack set of k images at different z locations, where preferably k>$H_{max}$/DOF; (ii) ensure that all images in the Z-stack image set are aligned (have the same coordinate system down to pixel level) and magnification change is negligible or has compensated; (iii) divide each image into a preselected number of sections/parts and through selected focus measure identify those section(s) which are deemed to be in focus; (iv) generated index map such that each position (x, y) keeps the index k of the image which had the sharpest section at the neighborhood; and (v) generate the "F-stack joined image" by combining the sharpest image sections according to the index map to the previous step.

In order to illustrate the potential benefits of the F-stacking method described above, we performed an experiment as the following. A 100 uL cell suspension, obtained by treating 4 mL of whole blood sample spiked with *E. coli* cells according to the procedure of Example 1, was spread on a 1.75% agar-based solid-phase growth medium prepared according to the procedure of Example 2. The solid-phase growth medium was incubated at 35° C. and 42% relative humidity. Dark-field imaging was performed employing a 7.5×0.21 NA objective with DOF of 14 μm and FOI of 1.1×1.7 mm.

A zoomed portion of an FOI at the incubation time of 2 hours is presented in FIG. 18C. The image sequence from left to right are taken at progressively higher distances relative to the solid-phase growth medium surface by increments of 20 um. Using nine different example autofocus algorithms mentioned in Example 9, it was observed that the blood debris subjectively went out of sharp focus for the objective displacement of ~20 μm. Thus, the upper limit of $H_{debris}$ was determined to be approximately 20 μm, as these small features were not easily digested by the blood lysis reagent that was employed to treat the blood sample. In addition, a qualitative examination of the images indicated that while moving from ~20 μm to 40 μm, in 20 μm increments, a subset of the microcolony was in sharp focus for each image. This range translated to $H_{colony}$~60 μm.

Accordingly, in some example implementations, after having detected and located a microcolony, the microcolony can be imaged by employing autofocusing methods to position the objective at an initial axial location, relative to the solid-phase growth medium, for achieving a focused image of the solid-phase growth medium surface that is proximal to the microcolony (e.g. focusing being achieved based on features of the debris field from sample processing, surface features of the solid-phase growth medium, or extrinsic fiducial particles introduced and adsorbed onto the surface of the solid-phase growth medium), and employing this initial axial location as a reference location for performing subsequent dark-field imaging of the microcolony.

In some example implementations, a single dark-field microcolony image can be acquired with the objective at the initial location corresponding to the focused surface of the solid-phase growth medium. Alternatively, a single dark-field microcolony image can be acquired at a location that is spatially offset, in the axial direction, from the initial axial location, such as, for example, by a pre-selected amount that is less than the expected maximum microcolony height during the incubation and imaging phase, such as, for example, an offset of 10, 20, 30, 40 or 50 microns.

In other example implementations, a Z-stack of dark-field microcolony images can be acquired with the objective at the initial location corresponding to the focused surface of the solid-phase growth medium. Alternatively, a Z-stack of dark-field microcolony images can be acquired at a location that is spatially offset, in the axial direction, from the initial axial location, such as, for example, by a pre-selected amount that is less than the expected maximum microcolony height during the incubation and imaging phase, such as, for example, an offset of 10, 20, 30, 40 or 50 microns.

The present inventors, having discovered the aforementioned DOF sensitivity of dark-field microcolony image, set out to employ the present example methods involving the scanning over multiple focusing planes to obtain images characterizing microcolony morphology during the microcolony growth phase for different pathogen species.

An 100 μL suspension including *Escherichia coli* and *Staphylococcus aureus* cells was seeded to the solid-phase growth medium containing 1.75% w/v of agar prepared according to the method of Example 2. The sample was incubated at 35° C. and 43% relative humidity and imaged at multiple time points during incubation and microcolony growth.

Dark-field images were obtained using a dark-field 7.5× objective with numerical aperture of 0.21. A small FOI containing one *Escherichia coli* (EC) microcolony and one *Staphylococcus aureus* (SA) microcolony, taken at t=3 hours of incubation following seeding, is presented in FIG. 8A. The microcolonies are identified and labeled (EC and SA) based on knowledge on the morphology of microcolonies grown on monocultures. As can be seen figure, none of the images provide a clearly focused view across each microcolony, with different subregions of each microcolony being brought into focus at different focus heights.

The imaging data shown in FIG. 8A was post-processed via F-stacking by combining 3, 5, 7, or 8 images taken at 3, 5, 7, or 8 respective different focus distances, with a step of 10 μm. The F-stacking process generated a single composite (joined) image. The results, which are shown in FIG. 8B, demonstrate the ability of F-stacking to generate microcolony images with much higher detail that any of the single images shown in FIG. 8A. As can be seen in FIG. 8B, the stacked image based on only two 10 μm focus steps appears to show focused morphological detail across the microcolony, with the F-stacked image quality not improving with the inclusion of additional stacked images. This suggests that in this present example case, images collected across the 20 μm height range (two 10 μm steps) plus the 14 μm DOF of the object are sufficient for F-stacking.

The F-stacking configuration in which two images were employed at ±10 μm was employed to generate F-stacked images at various time points during microcolony growth. The results, which are shown in FIG. 8C, demonstrate that this height range for image acquisition was suitable for tracking SA and EC microcolony evolution during the first four hours of growth while providing F-stacked images with clearly morphological details across each imaged microcolony.

It will be understood that the determination of a suitable number of F-stacked images (and the associated height range) will vary in practice, as noted above, and will depend, at least in part, on the microbial species, the time duration of growth, and the local shape of the solid-phase growth medium surface, for example, as characterized by $H_{tilt}$, $H_{debris}$, and $H_{colony}$, as described above, as well as by the temporal dependence of $H_{colony}$. The present inventors found that during the microcolony growth phase, with the microcolony diameter being less than 200 μm, the microcolony height varies within the range of 5-50 μm for most bacterial species, and that microcolonies undergo evolution through the phases of development from smaller (a typical height of microcolony be within the range 5-15 μm) to bigger (a typical height of microcolony be within the range 20-50 μm).

Accordingly, in applications involving the detection of microcolonies from pathogens having an unknown species, it may be beneficial to collect a set of images (e.g. for F-stacking) that span a range of approximately 100 μm in order to resolve the 3D morphology with acceptable sharpness. Accordingly, in some example implementations, dark-field images of such microcolonies are obtained using a system with a combined DOF (e.g. depth of field plus z-range of image acquisition) of more than $H_{tilt}+\max(H_{microcolony}; H_{debris})$. For example, between 20 and 300 μm, or for example between 10 and 100 um, or for example between 10 and 56 um.

EXAMPLES

The following examples are presented to enable those skilled in the art to understand and to practice embodiments of the present disclosure. They should not be considered as a limitation on the scope of the disclosure, but merely as being illustrative and representative thereof.

Example 1: Example Method of Sample Treatment of Spiked Whole Blood Samples

Sample treatment for a whole blood sample may be performed using a selective blood lysis reagent, which while digesting blood cells, does not substantially impact the viability of pathogenic bacterial cells. The blood lysis reagent used in this example for lysing 4 mL of whole blood had a volume of 4 mL and consisted of 35 mg/mL of purified saponin, 20 mg/mL of sodium polyanethole sulfonate (SPS), %0.2 w/v of Triton X-100, and 25 mM of sodium bicarbonate buffer pH 10, and 0.02% of antifoam SE-15 (MilliporeSigma). Sample preparation was performed for spiked whole blood samples as follows:

1. In a 15 mL centrifuge tube, 4 ml of the aforementioned blood lysis reagent was added to 4 ml of spiked whole blood sample.
2. The contents of the centrifuge tube were mixed by vortexing for 1 minute at maximum speed of the vortexer.
3. The centrifuge tube was centrifuged at 4000 rpm for 8 minutes.
4. A supernatant of 7.9 ml was removed.
5. The first wash cycle was performed by adding 2.9 mL of wash buffer to the residue, mixing the solution by gently vortexing, centrifugation at 4000 rpm for 3 min, withdrawing and discarding 2.9 mL of supernatant such that 100 µl of residual liquid was retained.
6. The second wash cycle was performed by adding 2.9 mL of wash buffer to the residue, mixing the solution by gently vortexing, centrifugation at 4000 rpm for 3 min, and withdrawing and discarding 2.9 mL of supernatant such that 100 µl of residual liquid was retained.
7. The third wash cycle was performed by adding 1.9 mL of wash buffer to the residue, mixing the solution by gently vortexing, centrifugation at 4000 rpm for 3 min, and withdrawing and discarding 1.9 mL of supernatant such that 100 µl of residual liquid was retained.

Example 2: Example Method of Preparation of Agar-Based Solid-Phase Growth Media Plates Agar-based solid-phase growth media plates were prepared with final agar concentrations within the range of 1.35-5% w/v.

To prepare the growth media with 1.35% gel three components are needed:
1. 3.85 g of TSAB (purchased from Hardy Diagnostics, containing 1.5 g of Pancreatic Digest of Casein, 0.5 g of Peptic Digest of Soy bean meal, 0.5 of NaCl, and 1.35 g of Agar).
2. 95 mL of distilled water,
3. 5 mL of sterile defibrinated sheep blood.

For media with higher agar concentration (e.g., 1.75% w/v) extra agar (0.4 g) is added to the TSAB. For the media with 1.0% w/v of agar, rather than using ready-made TSAB, the individual components (1.5 g of Pancreatic Digest of Casein, 0.5 g of Peptic Digest of Soy bean meal, 0.5 of NaCl) are added to 1 g of agar.

The preparation steps were as follows:
1. Add the extra agar to the TSAB if agar with higher percentage of agar is needed. TSAB powder with agar extra powder in molecular biology grade water on a hot plate at 100° C. inside a water bath for 10 mins.
2. Add TSAB to water,
3. Heat to boiling point and stir well.
4. Autoclave the solution (120° C. for 15 minutes)
5. Cool down to 55° C., add blood, and stir well.
6. Pre-warm pipette with warm water.
7. Dispense onto plates and let solidify for 5 mins.

Example 3: Microcolony Detection and Time-to-Positivity (TTP)

4 mL of whole blood, spiked with about 20 CFU of the cells, which had been prepared according to the method of Example 5, was processed according to the method of Example 1. An 1.35% w/v agar-based solid-phase growth medium, which had been prepared following the method of Example 2, was then centrifuged for 8 minutes and 100 µl of cell suspension were dispensed on it and allowed to be absorbed on the surface.

The plate was placed in into the incubator and imaged every 30 minutes (1, 1.5, 2, 2.5, 3, 3.5, 4, 4.5, 5, 5.5, 6, 6.5 hours after seeding) by taking 4×6 images across the solid-phase growth medium. The 10× objective was moved in z direction for autofocusing at each fifth imaging to lower the scanning time. The plate was also incubated for overnight and its image was taken by a conventional camera in addition to the microscopy imaging.

To align imaging data acquired at different time points (1, 1.5, 2, 2.5, 3, 3.5, 4, 4.5, 5, 5.5, 6 and 6.5 hours after seeding), 2D-2D registration (only translation and rotation are permitted) with rigid transformation constrains was performed on each image. Image registration is based on the detection and extraction of the local characteristic features such as corners, borders and/or blobs. We used SURF (Speeded-Up Robust Features) detector and features were extracted from the 2-D gray-scaled input images.

An octave metric was employed to specify the radial size of the blob, with the higher the octave the larger blobs are accepted as registration features. On the next step, the identified and tabulated features were compared between the images taken at $t_0$ and $t_n$ to find corresponding points between two images that might have been rotated and misaligned with respect to each other. The locations of matched points were then retrieved and transformed the $t_n$ image to be spatially referenced to $t_0$ image.

Intensity features present at $t_0$ were classified as background while intensity features appearing on further images were classified as foreground. Objects >100 pixels present in a foreground were classified as microcolonies.

FIG. 14 presents the number of detected microcolonies at the selected time points of incubation after seeding of the selected ATCC strains of Gram-positive (*Enterococcus Faecalis*—EF, *Enterococcus Faecium*—EFm, *Staphylococcus Aureus*—SA, *Staphylococcus Epidermidis*—SE, *Staphylococcus Haemolyticus*—SH, *Streptococcus Pyogenes*—Spyo) and Gram-negative (*Acinetobacter Baumannii*—AB, *Enterobacter Cloacae* Complex—ECC, *Enterobacter Aerogenes*—EA, *Escherichia Coli*—EC, *Klebsiella Pneumoniae*—KP, *Pseudomonas Aeruginosa*—PA, *Serratia Marcescens*—SM, *Proteus mirabilis*—PM) bacteria, recovered from spiked blood sample as described above. Measuring across 6 ATCC strains of Gram-positive bacteria and 8 ATCC strains of Gram-negative bacteria, we found that average time to positivity was 1.5 hours for detection at least one out of approximately 20 microcolonies with approximately 2.5 hours to detect all approximately 20 microcolonies. The time to positivity would be slightly longer if the more preferred case of 5× objective had been used.

Example 4: Seeding of Clean Sample

Phosphate buffer with molarity of 1 mM and volume of 100 µL was spiked with nominally $5 \times 10^4$ CFU of each cell strain. Specified volume of the sample was dispensed on a solid-phase growth medium, which had been prepared according to the method of Example 2.

Example 5: Microbial Cell Culture Preparation

Gram-positive bacteria except *Staphylococcus aureus* (SA) and *Streptococcus pneumoniae* (SP) cell culture was prepared as follows:
1. Thirty µL of respective bacteria species and strain glycerol stock was inoculated in 3 mL of tryptic soy broth (TSB) and incubated at 37° C. for overnight with shaking at 150 rpm.
2. Tenfold diluted culture in TSB was incubated at 37° C. for 1 hour.

*Staphylococcus aureus* (SA) cell culture was prepared as follows:
30 µL of respective strain glycerol stock was inoculated in 3 mL of TSB and incubated at 37° C. for 3 hours with shaking at 150 rpm. *Streptococcus pneumoniae* (SP) cell culture was prepared as follows:
30 µL of respective species or strain glycerol stock was inoculated in 3 mL of TSB and incubated at 37° C. for 3 hours with shaking at 80 rpm in the presence of $CO_2$ generating pouch.

Gram-negative bacteria except *Pseudomonas aeruginosa* (PA) cell culture was prepared as follows:
1. Thirty μL of respective bacteria species and strain glycerol stock was inoculated in 3 mL of TSB and incubated at 37° C. for overnight with shaking at 150 rpm.
2. Tenfold diluted culture in TSB was incubated at 37° C. for 1 hour.

*Pseudomonas aeruginosa* (PA) was prepared as follows:
1. Six μL of PA strain glycerol stock was streaked on tryptic soy agar (TSA) with 5% sheep blood plate and incubated at 37° C. for overnight (P1).
2. Bacteria colony was sub-cultured one more time on agar-based solid-phase growth media plate (P2).
3. One colony from the plate was inoculated in 3 ml.

Based on optical density (OD) measurements, serial dilutions of the respective bacteria were prepared in TSB at a nominal concentration down to $10^3$ CFU/mL.

Example 6: Preparing Cell Suspension from Bioball

Bioball® (Biomerieux) is a bead containing ~550 lyophilized microbial cells. The cell suspension from this bead is prepared through the following steps.
1. Thaw TSB growth media at room temperature for a minimum time of 30 minutes.
2. Dissolve a Bioball in 100 μL of the media.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore, what is claimed is:

1. A method of performing classification of a microcolony, the method comprising:
   employing a dark-field objective having a numerical aperture between 0.15 and 0.35 to acquire a dark-field image of the microcolony, the microcolony residing on a solid-phase growth medium; and
   processing the dark-field image to classify the microcolony among to two or more microbial cell type classes based on morphological features of the microcolony.

2. The method according to claim 1 wherein the dark-field image is acquired during a microcolony growth phase characterized by time-dependent changes in dark-field morphology of the microcolony.

3. The method according to claim 1 wherein the numerical aperture of the dark-field objective is between 0.18 and 0.32.

4. The method according to claim 1 wherein the numerical aperture of the dark-field objective is between 0.16 and 0.28.

5. The method according to claim 1 wherein the dark-field image is acquired prior to the microcolony having an effective diameter of 200 microns.

6. The method according to claim 1 wherein the microcolony is prepared by:
   seeding a microbial cell onto the solid-phase growth medium;
   incubating the solid-phase growth medium under conditions suitable for promoting growth of the microbial cell and the generation of the microcolony.

7. The method according to claim 6 wherein the solid-phase growth medium comprises agar having a concentration between 1 and 2.5% w/v.

8. The method according to claim 6 wherein the solid-phase growth medium comprises agar having a concentration between 1.5 and 2.25% w/v.

9. The method according to claim 6 wherein the solid-phase growth medium comprises agar having a concentration between 1.35 and 2% w/v.

10. The method according to claim 6 wherein the microbial cell is seeded onto the solid-phase growth medium by contacting a suspension with the solid-phase growth medium, the suspension comprising the microbial cell.

11. The method according to claim 10 wherein the suspension is derived from a whole blood sample in the absence of an intervening growth step.

12. The method according to claim 6 wherein the microcolony is a first microcolony, the microbial cell is a first microbial cell, the solid-phase growth medium is a first solid-phase growth medium having a first composition, the dark-field image is a first dark-field image, and wherein the microbial cell is seeded onto the first solid-phase growth medium by contacting a first aliquot of a suspension with the solid-phase growth medium, the first aliquot of the suspension comprising the first microbial cell, the method further comprising:
   contacting a second aliquot of the suspension with a second solid-phase growth medium, the second aliquot of the suspension comprising a second microbial cell, the second solid-phase growth medium having a second composition that differs from the first composition;
   incubating the solid-phase growth medium under conditions suitable for promoting growth of the second microbial cell and the generation of a second microcolony; and
   acquiring a second dark-field image, the second dark-field image characterizing a dark-field morphology of the second microcolony;
   wherein the first dark-field image and the second dark-field image are processed to classify of the microcolony.

13. The method according to claim 6 wherein the dark-field image of the microcolony is obtained within 3 to 5 hours from a time at which the microbial cell was seeded onto the solid-phase growth medium.

14. The method according to claim 6 wherein the solid-phase growth medium is incubated while maintaining a relative humidity between 30% and 70%.

15. The method according to claim 6 wherein the solid-phase growth medium is incubated while maintaining a relative humidity between 30% and 99%.

16. The method according to claim 6 further comprising:
   detecting a presence and a location of the microcolony; and
   employing the location of the microcolony to position the dark-field objective for acquiring the dark-field image.

17. The method according to claim 16 wherein the microcolony is detected by processing bright-field images of the solid-phase growth medium.

18. The method according to claim 17 wherein a separate bright-field objective is employed to acquire the bright-field images.

19. The method according to claim 17 wherein the dark-field objective is a dual-mode objective that is reconfigurable for dark-field and bright-field imaging, and wherein the dual-mode objective is configured for bright-field imaging during collection of the bright-field images.

20. The method according to claim 16 wherein detecting the presence of the microcolony comprises:
- intermittently performing a bright-field colony detection scan by scanning the solid-phase growth medium with a bright-field objective and collecting, for each bright-field colony detection scan, a set of bright-field colony detection images, each bright-field colony detection image corresponding to a different surface region of the solid-phase growth medium;
- during or after each bright-field colony detection scanning step, processing the acquired bright-field colony detection images according to microcolony detection criteria; and
- detecting a microcolony when the microcolony detection criteria is satisfied.

21. The method according to claim 20 further comprising, prior to performing the bright-field colony detection scans, performing at least one bright-field reference scan of the solid-phase growth medium with the bright-field objective to obtain a set of bright-field reference images, each bright-field reference image characterizing one of the surface regions; and
- prior to processing the bright-field colony detection images, applying a corresponding bright-field reference image to each bright field colony detection image to remove or reduce a presence of background noise in the bright-field colony detection images.

22. The method according to claim 21 wherein a plurality of bright-field reference scans are performed prior to performing the bright-field colony detection scans, and wherein the bright-field reference scans are performed until reference criterion associated with a stability of spatial features in the bright-field reference images is satisfied.

23. The method according to claim 21 wherein an initial bright field reference scan is performed after a background stabilization time delay.

24. The method according to claim 23 wherein the background stabilization time delay is at least 30 minutes.

25. The method according to claim 1 wherein the dark-field image is a final dark-field image that is obtained by:
- with the dark-field objective positioned proximal to the microcolony, collecting a plurality of initial dark-field images, each initial dark-field image being acquired at a different axial offset of the dark-field objective relative to the solid-phase growth medium;
- processing the plurality of initial dark-field images to determine a focal location suitable for obtaining a focused dark-field image of surface features residing on a surface of the solid-phase growth medium; and
- employing the focal location when positioning the dark-field objective to obtain the final dark-field image.

26. The method according to claim 25 wherein the dark-field objective is spatially offset from the focal location when acquiring the final dark-field image, thereby accommodating a finite height of the microcolony.

27. The method according to claim 26 wherein the final dark-field image is obtained by acquiring, at a plurality of additional locations that reside proximal to the focal location, a z-stack of secondary dark-field images; and
- processing the z-stack of secondary dark-field images to obtain the dark-field image for classification of the microcolony.

28. The method according to claim 26 wherein the final dark-field image is a composite image generated by focus-stacking two or more of the z-stack of secondary dark-field images.

29. The method according to claim 26 wherein processing the z-stack of secondary dark-field images comprises determining, from the z-stack of secondary dark-field images, a focused dark-field image having a focusing measure exceeding a remainder of the z-stack of secondary dark-field images.

30. The method according to claim 25 wherein the surface features comprise residual debris particles originating from a sample matrix.

31. The method according to claim 25 wherein the surface features comprise inherent surface features of the solid-phase growth medium.

32. The method according to claim 25 wherein the surface features comprise extrinsic particles adsorbed onto the surface of the solid-phase growth medium, the extrinsic particles having been previously contacted with the solid-phase growth medium.

33. The method according to claim 1 wherein the dark-field image is obtained by:
- acquiring a z-stack of initial dark-field images; and
- processing the z-stack of initial dark-field images to obtain the dark-field image employed for classification of the microcolony.

34. The method according to claim 33 wherein processing the z-stack of initial dark-field images comprises generating a composite image by focus-stacking two or more of the z-stack of initial dark-field images.

35. The method according to claim 33 wherein processing the z-stack of initial dark-field images comprises determining, from the z-stack of initial dark-field images, a focused dark-field image having a focusing measure exceeding a remainder of the z-stack of initial dark-field images.

36. The method according to claim 1 wherein the dark-field objective is employed to acquire one or more additional dark-field images of the microcolony, each additional dark-field image being acquired at a different time during growth of the microcolony, the dark-field image and the one or more additional dark-field images forming a set of dark-field images of the microcolony, and wherein the set of dark-field images are processed to classify the microcolony.

37. The method according to claim 36 wherein processing the set of dark-field images to classify the microcolony comprises employing a machine learning algorithm to process the set of dark-field images to classify the microcolony.

38. The method according to claim 37 wherein the machine learning algorithm was trained based on labeled reference image data comprising, for each of a plurality of types of microbial cells, a set of reference dark-field images corresponding to different phases of microcolony growth.

39. The method according to claim 37 wherein the machine learning algorithm is configured to process the set of dark-field images in the absence of employing a temporal ordering of the set of dark-field images.

40. The method according to claim 39 wherein the machine learning algorithm is configured to generate, for each dark-field image of the set of dark-field images, a set of classification measures, each classification measure providing a probability of the microcolony belonging to a respective microbial cell type class, and wherein the classification is determined by selecting the microbial cell type class having the highest associated classification measure among each of the dark-field images of the set of dark-field images.

41. The method according to claim 39 wherein the machine learning algorithm is configured to generate, for each dark-field image of the set of dark-field images, a set of classification measures, each classification measure providing a probability of the microcolony belonging to a respective microbial cell type class, and wherein the classification is determined by processing the classification measures to determine an aggregate classification measure.

42. The method according to claim 37 wherein the machine learning algorithm is employed to process the set of dark-field images according to a temporal ordering of the set of dark-field images.

43. The method according to claim 42 wherein the machine learning algorithm had been trained based on reference image data comprising, for each of a plurality of types of microbial cells, a set of temporally-ordered reference dark-field images corresponding to different phases of microcolony growth.

44. The method according to claim 42 wherein the machine learning algorithm comprises a recurrent neural network.

45. The method according to claim 42 wherein the machine learning algorithm comprises a long short term memory network.

46. The method according to claim 1 wherein the microbial cell type classes comprise Gram-positive and Gram-negative.

47. The method according to claim 1 wherein the microbial cell type classes comprise at least one bacterial species.

* * * * *